(12) United States Patent
Surman et al.

(10) Patent No.: US 8,993,765 B2
(45) Date of Patent: Mar. 31, 2015

(54) TETRAHYDRO-AZACARBOLINE MCH-1 ANTAGONISTS, METHODS OF MAKING, AND USES THEREOF

(75) Inventors: Matthew D. Surman, Albany, NY (US); Peter R. Guzzo, Niskayuna, NY (US); Emily Freeman, Guilderland, NY (US)

(73) Assignee: Albany Molecular Research, Inc., Albany, NY (US)

( * ) Notice: Subject to any disclaimer, the term of this patent is extended or adjusted under 35 U.S.C. 154(b) by 181 days.

(21) Appl. No.: 13/331,814

(22) Filed: Dec. 20, 2011

(65) Prior Publication Data

US 2012/0157460 A1 Jun. 21, 2012

Related U.S. Application Data

(60) Provisional application No. 61/425,602, filed on Dec. 21, 2010.

(51) Int. Cl.

| | | |
|---|---|---|
| *C07D 401/04* | (2006.01) | |
| *C07D 401/14* | (2006.01) | |
| *C07D 471/14* | (2006.01) | |
| *A61K 31/4353* | (2006.01) | |
| *A61K 31/4427* | (2006.01) | |
| *A61P 3/04* | (2006.01) | |
| *C07D 487/04* | (2006.01) | |

(52) U.S. Cl.
CPC ............ *C07D 487/04* (2013.01); *C07D 471/14* (2013.01)
USPC ............................................ 546/82; 514/293

(58) Field of Classification Search
USPC ............................................ 546/82; 514/293
See application file for complete search history.

(56) References Cited

U.S. PATENT DOCUMENTS

| | | | |
|---|---|---|---|
| 3,514,462 A | 5/1970 | Hester | |
| 4,978,669 A | 12/1990 | Barchas et al. | |
| 4,985,422 A | 1/1991 | North et al. | |
| 5,013,733 A | 5/1991 | Coates et al. | |
| 5,162,336 A | 11/1992 | Molino et al. | |
| 5,169,852 A | 12/1992 | Barchas et al. | |
| 5,183,820 A | 2/1993 | Coates et al. | |
| 5,187,180 A | 2/1993 | Gillard | |
| 5,223,625 A | 6/1993 | Van Wijngaarden et al. | |
| 5,225,407 A | 7/1993 | Oakley et al. | |
| 5,424,314 A | 6/1995 | Clemence et al. | |
| 5,466,688 A | 11/1995 | Commons et al. | |
| 5,506,234 A | 4/1996 | Huth et al. | |
| 5,527,794 A | 6/1996 | Commons et al. | |
| 5,563,147 A | 10/1996 | Gilmore et al. | |
| 5,569,661 A | 10/1996 | Haffer et al. | |
| 5,767,131 A | 6/1998 | Gluchowski et al. | |
| 5,811,551 A | 9/1998 | Chen et al. | |
| 5,854,245 A | 12/1998 | Duggan et al. | |
| 5,932,582 A | 8/1999 | Young et al. | |
| 5,972,980 A | 10/1999 | Cornicelli et al. | |
| 6,001,866 A | 12/1999 | Cornicelli et al. | |
| 6,177,440 B1 | 1/2001 | Bach et al. | |
| 6,255,306 B1 | 7/2001 | Macor | |
| 6,407,092 B1 | 6/2002 | Hester et al. | |
| 6,548,493 B1 | 4/2003 | Calvello et al. | |
| 6,552,017 B1 | 4/2003 | Robichaud et al. | |
| 6,605,639 B1 | 8/2003 | Tamura et al. | |
| 6,610,684 B2 | 8/2003 | Zaharevitz et al. | |
| 6,653,304 B2 | 11/2003 | Leftheris et al. | |
| 6,699,852 B2 | 3/2004 | Robichaud et al. | |
| 6,713,471 B1 | 3/2004 | Robichaud et al. | |
| 6,713,645 B1 | 3/2004 | Bach et al. | |
| 6,727,264 B1 | 4/2004 | Marzabadi et al. | |
| 6,838,456 B2 | 1/2005 | Orme et al. | |
| 6,849,619 B2 | 2/2005 | Robichaud et al. | |
| 6,849,640 B2 | 2/2005 | Ennis et al. | |
| 6,872,721 B2 | 3/2005 | Orme et al. | |
| 6,872,743 B2 | 3/2005 | Beight et al. | |

(Continued)

FOREIGN PATENT DOCUMENTS

| | | |
|---|---|---|
| CA | 2597193 A1 | 2/2009 |
| EP | 950661 A1 | 10/1999 |

(Continued)

OTHER PUBLICATIONS

Mendez-Andino et al., Drug Discovery Today, vol. 12( 21/22), 972-979, 2007.*
Kowalski et al. Expert Opin. Investig. Drugs 13(9), 1113-1122, 2004.*
Nahon, C. R. Biologies, 329, 623-638, 2006.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
International Search Report for International Patent Application No. PCT/US10/40800 (Aug. 30, 2010).

(Continued)

*Primary Examiner* — Venkataraman Balasubramanian
(74) *Attorney, Agent, or Firm* — LeClairRyan, a Professional Corporation

(57) ABSTRACT

The present invention relates to tetrahydro-azacarboline derivatives of formula (I):

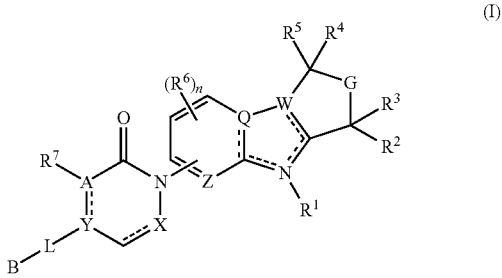

having the substituents as described herein which are melanin-concentrating hormone (MCH-1) receptor antagonists. The present invention also relates to pharmaceutical compositions including these compounds, and methods of preparation and use thereof.

22 Claims, No Drawings

(56) References Cited

U.S. PATENT DOCUMENTS

| | | |
|---|---|---|
| 6,875,762 B2 | 4/2005 | Hester et al. |
| 6,890,933 B1 | 5/2005 | Feng et al. |
| 6,906,095 B2 | 6/2005 | Cole et al. |
| 6,927,222 B2 | 8/2005 | Hansen et al. |
| 6,927,223 B1 | 8/2005 | Meadows et al. |
| 6,943,188 B2 | 9/2005 | Eriksson et al. |
| 6,951,874 B2 | 10/2005 | Hansen et al. |
| 6,951,881 B2 | 10/2005 | Cole et al. |
| 6,992,192 B2 | 1/2006 | Sawyer et al. |
| 7,022,856 B2 | 4/2006 | Orme et al. |
| 7,115,621 B2 | 10/2006 | Sawyer et al. |
| 7,122,554 B2 | 10/2006 | Sawyer et al. |
| 7,193,079 B1 | 3/2007 | Tepe |
| 7,196,103 B2 | 3/2007 | Nazare et al. |
| 7,250,514 B1 | 7/2007 | Xiao |
| 7,332,519 B2 | 2/2008 | Hinze et al. |
| 7,335,769 B2 | 2/2008 | Tepe |
| 7,385,055 B2 | 6/2008 | Tepe |
| 7,482,360 B2 | 1/2009 | Burnett et al. |
| 7,485,634 B2 | 2/2009 | Martin et al. |
| 7,872,017 B2 | 1/2011 | Ji et al. |
| 8,067,590 B2 | 11/2011 | Stenkamp et al. |
| 8,101,632 B2 | 1/2012 | Guzzo et al. |
| 8,158,643 B2 | 4/2012 | Andre-Gil et al. |
| 8,268,868 B2 | 9/2012 | Guzzo et al. |
| 8,273,770 B2 | 9/2012 | Guzzo et al. |
| 2002/0013333 A1 | 1/2002 | Batty et al. |
| 2002/0099068 A1 | 7/2002 | Ritzeler et al. |
| 2002/0173503 A1 | 11/2002 | Robichaud et al. |
| 2003/0022819 A1 | 1/2003 | Ling et al. |
| 2003/0095958 A1 | 5/2003 | Bhisetti et al. |
| 2003/0130293 A1 | 7/2003 | Bamdad |
| 2003/0144267 A1 | 7/2003 | Hansen et al. |
| 2003/0149047 A1 | 8/2003 | Eriksson et al. |
| 2003/0158225 A1 | 8/2003 | Hansen et al. |
| 2003/0225058 A1 | 12/2003 | Frank et al. |
| 2003/0232843 A1 | 12/2003 | Cole et al. |
| 2004/0002527 A1 | 1/2004 | Cole et al. |
| 2004/0023947 A1 | 2/2004 | Martin et al. |
| 2004/0116458 A1 | 6/2004 | Sawyer et al. |
| 2004/0122035 A1 | 6/2004 | Orme et al. |
| 2004/0186094 A1 | 9/2004 | Robichaud et al. |
| 2004/0235820 A1 | 11/2004 | Tepe |
| 2005/0004156 A1 | 1/2005 | Feng et al. |
| 2005/0026941 A1 | 2/2005 | Sawyer et al. |
| 2005/0033049 A1 | 2/2005 | Nazare et al. |
| 2005/0054634 A1 | 3/2005 | Busch et al. |
| 2005/0176775 A1 | 8/2005 | Devadas et al. |
| 2005/0187387 A1 | 8/2005 | Lynch et al. |
| 2005/0192333 A1 | 9/2005 | Hinze et al. |
| 2005/0215580 A1 | 9/2005 | Wang et al. |
| 2006/0004041 A1 | 1/2006 | Cummings et al. |
| 2006/0019952 A1 | 1/2006 | Distefano et al. |
| 2006/0128711 A1 | 6/2006 | Gallego et al. |
| 2006/0167259 A1 | 7/2006 | Chao et al. |
| 2006/0189639 A1 | 8/2006 | Stewart et al. |
| 2006/0235012 A1 | 10/2006 | Davidson et al. |
| 2006/0247228 A1 | 11/2006 | Umeda et al. |
| 2006/0276451 A1 | 12/2006 | Tepe |
| 2006/0281786 A1 | 12/2006 | Hamprecht et al. |
| 2006/0281796 A1 | 12/2006 | Edmondson et al. |
| 2006/0287296 A1 | 12/2006 | Tepe |
| 2006/0293305 A1 | 12/2006 | Tepe |
| 2007/0004765 A1 | 1/2007 | Graffner-Nordberg et al. |
| 2007/0027178 A1 | 2/2007 | Lee |
| 2007/0037791 A1 | 2/2007 | Rawson et al. |
| 2007/0049575 A1 | 3/2007 | Tepe |
| 2007/0049593 A1 | 3/2007 | Oka et al. |
| 2007/0149557 A1 | 6/2007 | Collins et al. |
| 2007/0173537 A1 | 7/2007 | Takemiya et al. |
| 2007/0185184 A1 | 8/2007 | Hanson et al. |
| 2007/0213351 A1 | 9/2007 | Sundermann et al. |
| 2007/0254877 A1 | 11/2007 | Nishikimi et al. |
| 2007/0293491 A1 | 12/2007 | Shafer et al. |
| 2008/0045539 A1 | 2/2008 | Ji et al. |
| 2008/0103164 A1 | 5/2008 | Gudmundsson et al. |
| 2008/0124319 A1 | 5/2008 | Pothoulakis et al. |
| 2008/0125475 A1 | 5/2008 | Linz et al. |
| 2008/0194803 A1 | 8/2008 | Sinclair et al. |
| 2008/0207594 A1 | 8/2008 | Mussmann et al. |
| 2008/0221141 A1 | 9/2008 | Friderichs et al. |
| 2008/0269055 A1 | 10/2008 | Bastiaans et al. |
| 2008/0287423 A1 | 11/2008 | Mussmann et al. |
| 2008/0292626 A1 | 11/2008 | Wang et al. |
| 2008/0312218 A1 | 12/2008 | Burnett et al. |
| 2009/0012062 A1 | 1/2009 | Andres-Gill et al. |
| 2009/0012077 A1 | 1/2009 | Dossetter et al. |
| 2009/0069367 A1 | 3/2009 | Bamdad |
| 2009/0075996 A1 | 3/2009 | Alper et al. |
| 2009/0232879 A1 | 9/2009 | Cable et al. |
| 2009/0264426 A1 | 10/2009 | Sakuraba et al. |
| 2010/0105679 A1 | 4/2010 | Guzzo et al. |
| 2010/0249105 A1 | 9/2010 | Schrimpf et al. |
| 2010/0331339 A9 | 12/2010 | Guzzo et al. |
| 2011/0003737 A1 | 1/2011 | Guzzo et al. |
| 2011/0003738 A1 | 1/2011 | Guzzo et al. |
| 2011/0003739 A1 | 1/2011 | Guzzo et al. |
| 2011/0003793 A1 | 1/2011 | Guzzo et al. |
| 2012/0035102 A9 | 2/2012 | Guzzo et al. |
| 2012/0058939 A9 | 3/2012 | Guzzo et al. |
| 2012/0058940 A9 | 3/2012 | Guzzo et al. |
| 2012/0157469 A1 | 6/2012 | Surman et al. |

FOREIGN PATENT DOCUMENTS

| | | |
|---|---|---|
| EP | 1462103 A1 | 9/2004 |
| EP | 1757607 A1 | 2/2007 |
| EP | 2003129 A1 | 12/2008 |
| EP | 2062895 A1 | 5/2009 |
| GB | 2120662 A | 12/1983 |
| WO | WO 92/00295 A1 | 1/1992 |
| WO | WO 94/22829 A2 | 10/1994 |
| WO | WO 96/11197 A1 | 4/1996 |
| WO | WO 96/12721 A1 | 5/1996 |
| WO | WO 96/33211 A1 | 10/1996 |
| WO | WO 97/12613 A1 | 4/1997 |
| WO | WO 97/23458 A1 | 7/1997 |
| WO | WO 97/31910 A1 | 9/1997 |
| WO | WO 98/00134 A1 | 1/1998 |
| WO | WO 98/00401 A1 | 1/1998 |
| WO | WO 99/47521 A1 | 9/1999 |
| WO | WO 00/64899 A1 | 11/2000 |
| WO | WO 00/77002 A1 | 12/2000 |
| WO | WO 01/05793 A1 | 1/2001 |
| WO | WO 01/58869 A2 | 8/2001 |
| WO | WO 01/64680 A1 | 9/2001 |
| WO | WO 01/68648 A1 | 9/2001 |
| WO | WO 01/87038 A2 | 11/2001 |
| WO | WO 01/87883 A1 | 11/2001 |
| WO | WO 01/94345 A2 | 12/2001 |
| WO | WO 02/04456 A1 | 1/2002 |
| WO | WO 02/04457 A1 | 1/2002 |
| WO | WO 02/24701 A2 | 3/2002 |
| WO | WO 0228859 A2 | 4/2002 |
| WO | WO 0228865 A2 | 4/2002 |
| WO | WO 02/50034 A2 | 6/2002 |
| WO | WO 02/064590 A2 | 8/2002 |
| WO | WO 02/064591 A2 | 8/2002 |
| WO | WO 02059082 A2 | 8/2002 |
| WO | WO 02059129 A2 | 8/2002 |
| WO | WO 02/088101 A2 | 11/2002 |
| WO | WO 02/088123 A1 | 11/2002 |
| WO | WO 02/098875 A1 | 12/2002 |
| WO | WO 03/014118 A1 | 2/2003 |
| WO | WO 03099821 A1 | 12/2003 |
| WO | WO 2004030629 A2 | 4/2004 |
| WO | WO 2004081010 A1 | 9/2004 |
| WO | WO 2005/070930 A2 | 8/2005 |
| WO | WO 2005/107471 A1 | 11/2005 |
| WO | WO 2005/108367 A1 | 11/2005 |
| WO | WO 2005118587 A1 | 12/2005 |
| WO | WO 2006/015035 A1 | 2/2006 |
| WO | WO 2006018184 A2 | 2/2006 |
| WO | WO 2006064355 A2 | 6/2006 |

(56) References Cited

FOREIGN PATENT DOCUMENTS

| WO | WO 2006064757 A1 | 6/2006 |
|---|---|---|
| WO | WO 2006089874 A1 | 8/2006 |
| WO | WO 2006/122931 A1 | 11/2006 |
| WO | WO 2006117548 A1 | 11/2006 |
| WO | WO 2007002051 A1 | 1/2007 |
| WO | WO 2007009120 A2 | 1/2007 |
| WO | WO 2007/024004 A1 | 3/2007 |
| WO | WO 2007/035620 A2 | 3/2007 |
| WO | WO 2007062175 A2 | 5/2007 |
| WO | WO 2007070796 A1 | 6/2007 |
| WO | WO 2007120333 A2 | 10/2007 |
| WO | WO 2007124903 A1 | 11/2007 |
| WO | WO 2007/142217 A1 | 12/2007 |
| WO | WO 2007141200 A1 | 12/2007 |
| WO | WO 2008011805 A1 | 1/2008 |
| WO | WO 2008024029 A1 | 2/2008 |
| WO | WO 2008046155 A1 | 4/2008 |
| WO | WO 2008060190 A2 | 5/2008 |
| WO | WO 2008081282 A2 | 7/2008 |
| WO | WO 2008101659 A1 | 8/2008 |
| WO | WO 2008101660 A1 | 8/2008 |
| WO | WO 2008103470 A3 | 8/2008 |
| WO | WO 2008106594 A2 | 9/2008 |
| WO | WO 2008112280 A1 | 9/2008 |
| WO | WO 2009003003 A2 | 12/2008 |
| WO | WO 2009022104 A1 | 2/2009 |
| WO | WO 2009032123 A2 | 3/2009 |
| WO | WO 2009/089482 | 7/2009 |
| WO | WO 2011003005 A1 | 1/2011 |
| WO | WO 2011003007 A1 | 1/2011 |
| WO | WO 2011003012 A1 | 1/2011 |
| WO | WO 2011003021 A1 | 1/2011 |

OTHER PUBLICATIONS

Written Opinion of the International Patent Searching Authority for International Patent Application No. PCT/US10/40800 (Aug. 30, 2010).
International Search Report for International Patent Application No. PCT/US10/40809 (Aug. 30, 2010).
Written Opinion of the International Searching Authority for International Patent Application No. PCT/US10/40809 (Aug. 30, 2010).
International Search Report for International Patent Application No. PCT/US2010/040803 (Aug. 30, 2010).
Written Opinion for International Patent Application No. PCT/US2010/040803 (Aug. 30, 2010).
International Search Report for International Patent Application No. PCT/US10/40820 (Aug. 30, 2010).
Written Opinion of the International Searching Authority for International Patent Application No. PCT/US10/40820 (Aug. 18, 2010).
BE 896590 to Gadient (Oct. 28, 1983) (abstract only).
CN 101074207 to Deng et al. (Nov. 21, 2007) (abstract only).
IN 2000CH01126 to Bipul et al. (Mar. 4, 2005) (abstract only).
JP 04319958 to Ito, A. (Nov. 10, 1992) (abstract only).
JP 2951434 to Ito, A. (Sep. 20, 1999) (abstract only).
International Search Report for International Patent Application No. PCT/US2009/030646 (Apr. 2, 2009).
Written Opinion of the International Searching Authority for International Patent Application No. PCT/US2009/030646 (Apr. 2, 2009).
Extended European Search Report for corresponding EP Application No. 10794771.5 (mailed Oct. 16, 2012).
Kokkotou et al., "Melanin-Concentrating Hormone as a Mediator of Intestinal Inflammation," PNAS 105(30):10613-10618 (2008).
Lakaye et al., "Melanin-Concentrating Hormone and Immune Function," Peptides 30:2076-2080 (2009).
Kokkotou et al., "Melanin-Concentrating Hormone (MCH) Modulates C Difficile Toxin A-Mediated Enteritis in Mice," Gut. 58(1):34-40 (2009).
Office Action dated Jan. 24, 2012 for U.S. Appl. No. 12/351,561.
Office Action dated Mar. 7, 2012 for Chinese Application No. 200980105529.7.
Office Action dated Jan. 30, 2013 for U.S. Appl. No. 12/828,890.
Office Action dated Feb. 20, 2013 for U.S. Appl. No. 12/828,955.
Patent Examination Report dated Oct. 22, 2012 for Australian Application No. 2009204048.
Office Action dated Jan. 5, 2013 for Chinese Application No. 200980105529.7.
Translation of Office Action dated Oct. 30, 2012 for Israeli Application No. 206594.
Office Action dated Feb. 17, 2011 for New Zealand Application No. 586120.
Office Action dated May 30, 2012 for New Zealand Application No. 586120.
Extended Search Report dated Jun. 7, 2012 for European Application No. 12163813.4.
Office Action dated Jan. 17, 2013 for U.S. Appl. No. 12/828,855.
Jantzen and Robinson, Modern Pharmaceutics, 596 (1996).
STN Registry Database, RN 1260582-72-6, available online Jan. 27, 2011.
Hadden et al., "Synthesis and SAR of 4-aryl-1-(indazol-5-yl)pyridin-2(1H)ones as MCH-1 Antagonists for the Treatment of Obesity," Bioorg. Med. Chem. Lett. 20:7020-7023 (2010).
Sargent et al., "New Central Targets for the Treatment of Obesity," Br. J. Clin. Pharmacol. 68(6):852-860 (2009).
Henderson et al., "Tetrahydrocarboline Analogs as MCH-1 Antagonists," Bioorg. Med. Chem. Lett. 20:7024-7028 (2010).
Surman et al., "5-(Pyridinon-1-yl)indazoles and 5-(furopyridinon-5-yl)indazoles as MCH-1 Antagonists," Bioorg. Med. Chem. Lett. 20:7015-7019 (2010).
Viggers et al., "Development and Validation of a Radioligand Receptor Binding Assay for MCH-1 Receptors Using [3H]AMR-MCH-1 In Vitro and Ex Vivo," Abstract 584.27/SS8, Society for Neuroscience Annual Meeting (2008).
International Search Report and Written Opinion for International Patent Application No. PCT/US2011/066027 (Aug. 14, 2012).
International Search Report and Written Opinion for International Patent Application No. PCT/US2011/066177 (Jun. 28, 2012).
Office action dated Jul. 2, 2012 for U.S. Appl. No. 12/828,807.
Office action dated Jul. 19, 2013 for U.S. Appl. No. 13/330,989.
Carpenter et al., "Melanin-Concentrating Hormone Receptor Antagonist as Potential Antiobesity Agents," Expert Opin. Ther. Patents, 12(11):1639-1646 (2002).
Dyke et al., "Recent Developments in the Discovery of MCH-1R Antagonists for the Treatment of Obesity—an Update," Expert Opin. Ther. Patents, 15(10):1303-1313 (2005).
Johansson "Recent Progress in the Discovery of Melanin-Concentrating Hormone 1-receptor Antagonists," Expert Opin. Ther. Patents, 21(6):905-925 (2011).
Vippagunta et al., "Crystalline Solids," Adv. Drug Deliv. Reviews 48:3-26 (2001).
"Burger's Medicinal Chemistry," edited by Manfred E. Wolf, $5^{th}$ Ed. Part 1, 975-977 (1995).
Banker et al., "Modern Pharmaceutics," $3^{rd}$ Ed. pp. 451, 596 (1996).
Translation of Office Action dated Oct. 3, 2013 for Japanese Application No. 2010-542381.
Translation of Notice Prior to Notice of Allowance dated Jan. 23, 2014 for Israeli Application No. 206594.
Translation of Notice of Reasons for Rejection for Japanese Patent Application No. 2012-518609 (Jul. 7, 2014).

* cited by examiner

TETRAHYDRO-AZACARBOLINE MCH-1 ANTAGONISTS, METHODS OF MAKING, AND USES THEREOF

This application claims the benefit of U.S. Provisional Patent Application Ser. No. 61/425,602, filed Dec. 21, 2010, which is hereby incorporated by reference in its entirety.

FIELD OF THE INVENTION

The present invention relates to tetrahydro-azacarboline derivatives, which are melanin-concentrating hormone (MCH-1) receptor antagonists, pharmaceutical compositions including these compounds, and methods of preparation and use thereof. The compounds are useful in the treatment of, for example, obesity, anxiety, depression, non-alcoholic fatty liver disease, psychiatric disorders, and inflammatory bowel disease.

BACKGROUND OF THE INVENTION

Obesity and the multitude of co-morbidities associated with obesity such as diabetes, dyslipidemia, coronary heart disease, and certain cancers are a major concern for public health. The currently available pharmaceutical therapies for the treatment of obesity have limited efficacy and side effects that limit their use. Thus, there is a significant medical need for better pharmacotherapy for obesity.

Obesity has associated with it, economic and social costs. Obese people, an increasing proportion of most western societies, are regarded as having out of control feeding habits often associated with low self-esteem. Moreover, obese persons are more likely to have medical problems associated with or exacerbated by the excess body weight. Examples of medical conditions caused, exacerbated, or triggered by excessive weight include bone fractures, pains in the knee joints, arthritis, increased risk of hypertension, artherosclerosis, stroke, and diabetes.

Melanin-concentrating hormone (MCH) has been identified as an orexigenic peptide that exerts an effect on food intake and body weight regulation. MCH is a cyclic 19 amino acid neuropeptide expressed in the zona incerta and lateral hypothalamus in response to both energy restriction and leptin deficiency. MCH is known to stimulate feeding when injected into the lateral ventricle of rats and the mRNA for MCH is upregulated in the hypothalamus of genetically obese mice (ob/ob) and in fasted control and ob/ob animals. In addition, animals treated with MCH show increases in glucose, insulin and leptin levels, mimicking human metabolic syndrome (Gomori, "Chronic Infusion of MCH Causes Obesity in Mice," *Am. J. Physiol. Endocrinol. Metab.,* 284:E583 (2002)). Mice lacking MCH are hypophagic and lean with increased metabolic rate, whereas animals over-expressing MCH gain excess weight on both standard and high fat diets. MCH is thought to have effects on other nervous system functions as well (Rocksz, "Biological Examination of Melanin Concentrating Hormone 1: Multi-tasking from the Hypothalamus," *Drug News Perspect.,* 19(5):273 (2006)). An orphan G-protein coupled receptor (GPCR) was recently identified as a receptor for MCH. Disruption of the binding between MCH and the MCH receptor, i.e. MCH antagonism, may thus be used to counteract the effects of MCH (McBriar, "Recent Advances in the Discovery of Melanin-Concentrating Hormone Receptor Antagonists," *Curr. Opin. Drug Disc. & Dev.,* 9(4):496 (2006)).

The current preferred treatment for obesity as well as Type II non-insulin dependent diabetes is diet and exercise with a view toward weight reduction and improved insulin sensitivity for diabetics. Patient compliance, however, is usually poor. The problem is compounded by the fact that there is currently only one medication approved for the treatment of obesity (orlistat (XENICAL™)).

The present invention is directed to overcoming these and other deficiencies in the art.

SUMMARY OF THE INVENTION

The present invention relates to a compound of formula (I):

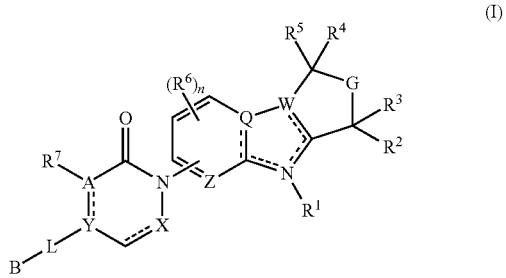

wherein
G is —NR$^8$—CR$^9$R$^{10}$— or —CR$^9$R$^{10}$—NR$^8$—;
X is CR$^{16}$, C(R$^{16}$)$_2$, N, or NR$^{16}$;
Y is CR$^{16}$, C, or N;
W is C or N;
Q is C or N;
Z is C, CH, or N;
L is —(CH$_2$)$_p$—O—, —(CH$_2$)$_p$—, —CH=CH—, or a bond;
A is C, CH, CH$_2$, or N;
B is aryl, heteroaryl, heterocyclyl, or cycloalkyl, wherein each of the aryl, heteroaryl, heterocyclyl, or cycloalkyl is optionally substituted with from 1 to 3 substituents selected from the group consisting of H, alkoxy, —S-alkyl, optionally substituted C$_1$-C$_6$ alkyl, halogen, —CF$_3$, and —CN;
R$^1$ is optionally present and, if present, is selected from the group consisting of H, —S(O)$_q$R$^{12}$, —C(O)R$^{12}$, —C(O)NR$^{11}$R$^{12}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl is optionally substituted with from 1 to 3 substituents independently selected at each occurrence thereof from C$_1$-C$_3$ alkyl, halogen, —CN, —OR$^{14}$, —NR$^{14}$R$^{15}$, and phenyl which is optionally substituted 1-3 times with halogen, C$_1$-C$_4$ alkyl, C$_1$-C$_4$ haloalkyl, C$_1$-C$_4$ alkoxy, —CN, —OR$^{14}$, or —NR$^{14}$R$^{15}$;
R$^2$-R$^5$ and R$^9$-R$^{10}$ are each, independently, selected from the group consisting of H, halogen, —OR$^{11}$, —NR$^{11}$R$^{12}$, —NR$^{11}$C(O)R$^{12}$, —NR$^{11}$C(O)$_2$R$^{12}$, —NR$^{13}$C(O)NR$^{12}$R$^{13}$, —S(O)$_q$R$^{12}$, —CN, —C(O)R$^{12}$, —C(O)NR$^{11}$R$^{12}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^{14}$, —NR$^{14}$R$^{15}$, and phenyl which is optionally substituted 1-3 times with halogen, C$_1$-C$_4$ alkyl, C$_1$-C$_4$ haloalkyl, C$_1$-C$_4$ alkoxy, —CN, —OR$^{14}$, or —NR$^{14}$R$^{15}$; or R$^2$ and R$^3$ or R$^4$ and R$^5$ can combine to form an oxo, thio, imine, cycloalkyl, or heterocycle group containing from 1 to 5 heteroatoms selected from the group consisting of oxygen, nitrogen, and sulfur;

$R^6$ is independently selected at each location from the group consisting of H, halogen, —$OR^{11}$, —$NR^{11}C(O)R^{12}$, —$NR^{11}C(O)_2R^{12}$, —$NR^{13}C(O)NR^{12}R^{13}$, —$S(O)_qR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{14}$, —$NR^{14}R^{15}$, and phenyl which is optionally substituted 1-3 times with halogen, $C_1$-$C_4$ alkyl, $C_1$-$C_4$ haloalkyl, $C_1$-$C_4$ alkoxy, —CN, —$OR^{14}$, or —$NR^{14}R^{15}$;

$R^7$ is optionally present and, if present, is selected from the group consisting of H, halogen, —$OR^{11}$, —$NR^{11}R^{12}$, —$NR^{11}C(O)R^{12}$, —$NR^{11}C(O)_2R^{12}$, —$NR^{13}C(O)NR^{12}R^{13}$, —$S(O)_qR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{14}$, —$NR^{14}$—$R^{15}$, and phenyl which is optionally substituted 1-3 times with halogen, $C_1$-$C_4$ alkyl, $C_1$-$C_4$ haloalkyl, $C_1$-$C_4$ alkoxy, —CN, —$OR^{14}$, or —$NR^{14}R^{15}$;

$R^8$ is selected from the group consisting of H, —$S(O)_qR^{12}$, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, and heteroaryl is optionally substituted with from 1 to 3 substituents independently selected at each occurrence thereof from $C_1$-$C_3$ alkyl, halogen, —CN, —$OR^{14}$, —$NR^{14}R^{15}$, and phenyl which is optionally substituted 1-3 times with halogen, $C_1$-$C_4$ alkyl, $C_1$-$C_4$ haloalkyl, $C_1$-$C_4$ alkoxy, —CN, —$OR^{14}$, or —$NR^{14}R^{15}$;

$R^{11}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{12}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{13}$ is $C_1$-$C_4$ alkyl, $C_1$-$C_4$ haloalkyl, or phenyl;

$R^{14}$ and $R^{15}$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

$R^{16}$ is selected from the group consisting of H, halogen, —$OR^{11}$, —$NR^{11}R^{12}$—$NR^{11}C(O)R^{12}$, —$NR^{11}C(O)_2R^{12}$, —$NR^{12}C(O)NR^{12}R^{13}$, —$S(O)_qR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{14}$, —$NR^{14}R^{15}$, and phenyl which is optionally substituted 1-3 times with halogen, $C_1$-$C_4$ alkyl, $C_1$-$C_4$ haloalkyl, $C_1$-$C_4$ alkoxy, —CN, —$OR^{14}$, or —$NR^{14}R^{15}$;

n is 0, 1, 2, or 3;

p is from 1 to 4;

q is 0, 1, or 2; and

=== represents an optional double bond, or an oxide thereof, a pharmaceutically acceptable salt thereof, a solvate thereof, or prodrug thereof.

Additional aspects of the present invention include pharmaceutical compositions comprising a compound of the invention and a pharmaceutically acceptable carrier and, optionally, one or more additional additive agent(s) as discussed below.

The present invention also relates to a method of treating a disease or condition which is susceptible to treatment with a MCH-1 receptor antagonist. This method involves selecting a patient with a disease or condition which is susceptible to treatment with a MCH-1 antagonist and administering to the patient a therapeutically effective amount of a compound of formula I or a pharmaceutically acceptable salt thereof.

The present invention also relates to a method of treating obesity in a subject in need of weight loss. This method involves selecting a patient in need of weight loss and administering to the patient a therapeutically effective amount of a compound of formula I or a pharmaceutically acceptable salt thereof.

Yet another aspect of the present invention relates to a method of treating obesity in a subject who has experienced weight loss. This method involves selecting a patient who has experienced weight loss and administering to the patient a therapeutically effective amount of a compound of formula I or a pharmaceutically acceptable salt thereof.

A further aspect of the present invention relates to a method of treating anxiety. This method involves selecting a patient with anxiety and administering to the patient a therapeutically effective amount of a compound of formula I or a pharmaceutically acceptable salt thereof.

The present invention also relates to a method of treating depression. This method involves selecting a patient with depression and administering to the patient a therapeutically effective amount of a compound of formula I or a pharmaceutically acceptable salt thereof.

Another aspect of the present invention relates to a method of treating non-alcoholic fatty liver disease. This method involves selecting a patient who has non-alcoholic fatty liver disease and administering to the patient a therapeutically effective amount of a compound of formula I or a pharmaceutically acceptable salt thereof.

Yet another aspect of the present invention relates to a method of treating inflammatory bowel disease. This method involves selecting a patient who has inflammatory bowel disease and administering to the patient a therapeutically effective amount of a compound of formula I or a pharmaceutically acceptable salt thereof.

A further aspect of the present invention relates to a process for preparation of a product compound of formula I which includes treating a first intermediate compound of formula V:

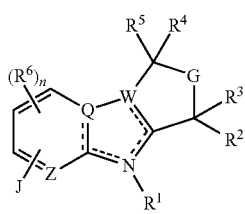

wherein J is a halogen, under conditions effective to form the product compound.

It has now been found that compounds of formula I are MCH-1 receptor antagonists. This invention provides compounds that bind to the MCH-1 receptor with high affinity. The compounds provided by formula I are useful for the treatment of obesity, anxiety, depression, psychiatric disorders, and other disorders described herein. In particular, it is contemplated that the compounds of this invention will be effective in treating obesity, including weight loss and maintenance of weight loss in patients who have been diagnosed with obesity by the one or more of the following measurements: an increased body mass index, increased waist circumference (an indicator of intra-abdominal fat), Dual Energy X-Ray Absorptiometry (DEXA), and trucal (android) fat mass. It is further contemplated that the compounds of the invention will be effective in inducing improvements in certain factors measured in these tests.

DETAILED DESCRIPTION OF THE INVENTION

The present invention relates to a compound of formula (I):

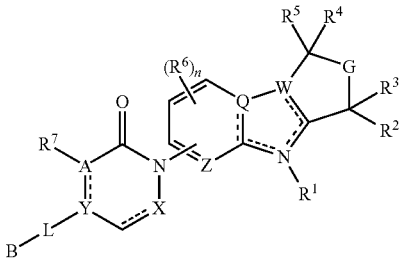

wherein
G is —NR$^8$—CR$^9$R$^{10}$— or —CR$^9$R$^{10}$—NR$^8$—;
X is CR$^{16}$, C(R$^{16}$)$_2$, N, or NR$^{16}$;
Y is CR$^{16}$, C, or N;
W is C or N;
Q is C or N;
Z is C, CH, or N;
L is —(CH$_2$)$_p$—O—, —(CH$_2$)$_p$—, —CH=CH—, or a bond;
A is C, CH, CH$_2$, or N;
B is aryl, heteroaryl, heterocyclyl, or cycloalkyl, wherein each of the aryl, heteroaryl, heterocyclyl, or cycloalkyl is optionally substituted with from 1 to 3 substituents selected from the group consisting of H, alkoxy, —S-alkyl, optionally substituted C$_1$-C$_6$ alkyl, halogen, —CF$_3$, and —CN;
R$^1$ is optionally present and, if present, is selected from the group consisting of H, —S(O)$_q$R$^{12}$, —C(O)R$^{12}$, —C(O)NR$^{11}$R$^{12}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl is optionally substituted with from 1 to 3 substituents independently selected at each occurrence thereof from C$_1$-C$_3$ alkyl, halogen, —CN, —OR$^{14}$, —NR$^{14}$R$^{15}$, and phenyl which is optionally substituted 1-3 times with halogen, C$_1$-C$_4$ alkyl, C$_1$-C$_4$ haloalkyl, C$_1$-C$_4$ alkoxy, —CN, —OR$^{14}$, or —NR$^{14}$R$^{15}$;

R$^2$-R$^5$ and R$^9$-R$^{10}$ are each, independently, selected from the group consisting of H, halogen, —OR$^{11}$, —NR$^{11}$R$^{12}$, —NR$^{11}$C(O)R$^{12}$, —NR$^{11}$C(O)$_2$R$^{12}$, —NR$^{13}$C(O)NR$^{12}$R$^{13}$, —S(O)$_q$R$^{12}$, —CN, —C(O)R$^{12}$, —C(O)NR$^{11}$R$^{12}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^{14}$, —NR$^{14}$R$^{15}$, and phenyl which is optionally substituted 1-3 times with halogen, C$_1$-C$_4$ alkyl, C$_1$-C$_4$ haloalkyl, C$_1$-C$_4$ alkoxy, —CN, —OR$^{14}$, or —NR$^{14}$R$^{15}$; or R$^2$ and R$^3$ or R$^4$ and R$^5$ can combine to form an oxo, thio, imine, cycloalkyl, or heterocycle group containing from 1 to 5 heteroatoms selected from the group consisting of oxygen, nitrogen, and sulfur;

R$^6$ is independently selected at each location from the group consisting of H, halogen, —OR$^{11}$, —NR$^{11}$C(O)R$^{12}$, —NR$^{11}$C(O)$_2$R$^{12}$, —NR$^{13}$C(O)NR$^{12}$R$^{13}$, —S(O)$_q$R$^{12}$, —CN, —C(O)R$^{12}$, —C(O)NR$^{11}$R$^{12}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^{14}$, —NR$^{14}$R$^{15}$, and phenyl which is optionally substituted 1-3 times with halogen, C$_1$-C$_4$ alkyl, C$_1$-C$_4$ haloalkyl, C$_1$-C$_4$ alkoxy, —CN, —OR$^{14}$, or —NR$^{14}$R$^{15}$;

R$^7$ is optionally present and, if present, is selected from the group consisting of H, halogen, —OR$^{11}$, —NR$^{11}$R$^{12}$, —NR$^{11}$C(O)R$^{12}$, —NR$^{11}$C(O)$_2$R$^{12}$, —NR$^{13}$C(O)NR$^{12}$R$^{13}$, —S(O)$_q$R$^{12}$, —CN, —C(O)R$^{12}$, —C(O)NR$^{11}$R$^{12}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^{14}$, —NR$^{14}$—R$^{15}$, and phenyl which is optionally substituted 1-3 times with halogen, C$_1$-C$_4$ alkyl, C$_1$-C$_4$ haloalkyl, C$_1$-C$_4$ alkoxy, —CN, —OR$^{14}$, or —NR$^{14}$R$^{15}$;

R$^8$ is selected from the group consisting of H, —S(O)$_q$R$^{12}$, —C(O)R$^{12}$, —C(O)NR$^{11}$R$^{12}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl is optionally substituted with from 1 to 3 substituents independently selected at each occurrence thereof from C$_1$-C$_3$ alkyl, halogen, —CN, —OR$^{14}$, —NR$^{14}$R$^{15}$, and phenyl which is optionally substituted 1-3 times with halogen, C$_1$-C$_4$ alkyl, C$_1$-C$_4$ haloalkyl, C$_1$-C$_4$ alkoxy, —CN, —OR$^{14}$, or —NR$^{14}$R$^{15}$;

$R^{11}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)$R^{13}$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{12}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{13}$ is $C_1$-$C_4$ alkyl, $C_1$-$C_4$ haloalkyl, or phenyl;

$R^{14}$ and $R^{15}$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)$R^{13}$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

$R^{16}$ is selected from the group consisting of H, halogen, —O$R^{11}$, —N$R^{11}R^{12}$, —N$R^{11}$C(O)$R^{12}$, —N$R^{11}$C(O)$_2R^{12}$, —N$R^{12}$C(O)N$R^{12}R^{13}$, S(O)$_qR^{12}$, —CN, —C(O)$R^{12}$, —C(O)N$R^{11}R^{12}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —O$R^{14}$, —N$R^{14}R^{15}$, and phenyl which is optionally substituted 1-3 times with halogen, $C_1$-$C_4$ alkyl, $C_1$-$C_4$ haloalkyl, $C_1$-$C_4$ alkoxy, —CN, —O$R^{14}$, or —N$R^{14}R^{15}$;

n is 0, 1, 2, or 3;

p is from 1 to 4;

q is 0, 1, or 2; and

═ represents an optional double bond, or an oxide thereof, a pharmaceutically acceptable salt thereof, a solvate thereof, or prodrug thereof.

As used above, and throughout the description of the invention, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Lower alkyl refers to alkyl groups having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, and the like.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. In the present invention, the term "alkenyl" may also refer to a hydrocarbon chain having 2 to 6 carbons containing at least one double bond and at least one triple bond.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "aryl" means an aromatic monocyclic or multicyclic (polycyclic) ring system of 6 to about 19 carbon atoms, preferably of 6 to about 10 carbon atoms, and includes arylalkyl groups. The ring system of the aryl group may be optionally substituted. Representative aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" means an alkyl residue attached to an aryl ring. Examples are benzyl, phenethyl, and the like.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be

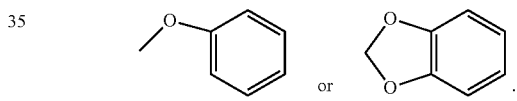

The term "compounds of the invention", and equivalent expressions, are meant to embrace compounds of general formula I as hereinbefore described. Also contemplated are the prodrugs, the pharmaceutically acceptable salts, the oxides, the solvates, e.g. hydrates, and inclusion complexes of that compound, where the context so permits, as well as any stereoisomeric form, or a mixture of any such forms of that compound in any ratio. Inclusion complexes are described in Remington, *The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims. Thus, in accordance with some embodiments of the invention, a compound as described herein, including in the contexts of pharmaceutical compositions, methods of treatment, and compounds per se, is provided as the salt form. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "cycloalkyl" means a non-aromatic, saturated or unsaturated, mono- or multi-cyclic ring system of about 3 to about 7 carbon atoms, preferably of about to about 7 carbon atoms, and which may include at least one double bond.

Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "cycloalkylalkyl" means an cycloalkyl-alkyl-group in which the cycloalkyl and alkyl are as defined herein. Exemplary cycloalkylalkyl groups include cyclopropylmethyl and cyclopentylmethyl. The alkyl radical and the cycloalkyl radical may be optionally substituted as defined herein.

The term "haloalkyl" means both branched and straight-chain alkyl substituted with one or more halogen, wherein the alkyl group is as herein described.

The term "halogen" means fluorine, chlorine, bromine, or iodine.

The term "heteroaryl" means an aromatic monocyclic or multi-cyclic ring system of about 5 to about 19 ring atoms, preferably about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, phthalazinyl, quinoxalinyl, 2,3-dihydrobenzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "heterocyclyl" or "heterocycle" refers to a stable 3- to 18-membered ring (radical) which consists of carbon atoms and from one to five heteroatoms selected from the group consisting of nitrogen, oxygen and sulfur. For purposes of this invention, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "method of treating" means amelioration or relief from the symptoms and/or effects associated with the disorders described herein. As used herein, reference to "treatment" of a patient is intended to include prophylaxis.

The term "monocyclic" used herein indicates a molecular structure having one ring.

The term "optionally substituted" is used to indicate that a group may have a substituent at each substitutable atom of the group (including more than one substituent on a single atom), provided that the designated atom's normal valency is not exceeded and the identity of each substituent is independent of the others. In accordance with the present invention, up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "pharmaceutical composition" means a composition comprising a compound of formula I and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. As used herein, the term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Commonly, the conversion of prodrug to drug occurs by enzymatic processes in the liver or blood of the mammal Many of the compounds of the invention may be chemically modified without absorption into the systemic circulation, and in those cases, activation in vivo may come about by chemical action (as in the acid-catalyzed cleavage in the stomach) or through the intermediacy of enzymes and microflora in the gastrointestinal GI tract. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier (1985); Methods in Enzymology, K. Widder et al, Ed., Academic Press, 42, p. 309-396 (1985); A Textbook of Drug Design and Development, Krogsgaard-Larsen and H. Bundgaard, ed., Chapter 5; "Design and Applications of Prodrugs," p. 113-191 (1991); Advanced Drug Delivery Reviews, H. Bundgaard, 8, p. 1-38 (1992); Journal of Pharmaceutical Sciences, 77:285 (1988); Nakeya et al, Chem. Pharm. Bull., 32:692 (1984); Higuchi et al., "Prodrugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The term "pharmaceutically acceptable salt" refers to salts prepared from pharmaceutically acceptable non-toxic acids or bases including inorganic acids and bases and organic acids and bases. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine. Pharmaceutically acceptable salts include, but are not limited to, amine salts, such as but not limited to N, N'dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine, and tris(hydroxymethyl)aminomethane; alkali metal salts, such as but not limited to lithium, potassium, and sodium; alkali earth metal salts, such as but not limited to barium, calcium, and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula C=C(OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C=C(OC(O)R) where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3 or 4, solvent or water molecules.

The term "polycyclic" or "multi-cyclic" used herein indicates a molecular structure having two or more rings, including, but not limited to, fused, bridged, or spiro rings.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups." Suitable groups for that purpose are discussed in standard textbooks in the field of chemistry, such as Greene, *Protective Groups in Organic Synthesis*, John Wiley & Sons, New York (1991), which is hereby incorporated by reference in its entirety.

The term "solvate" refers to a compound of formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "therapeutically effective amount" is meant to describe an amount of compound of the present invention effective producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

One embodiment of the present invention relates to a compound of formula (II):

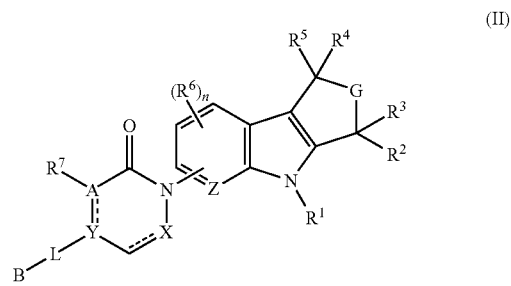

(II)

wherein the substituents are as described above. In a further embodiment, Z is N.

Another embodiment of the present invention relates to a compound of formula (III):

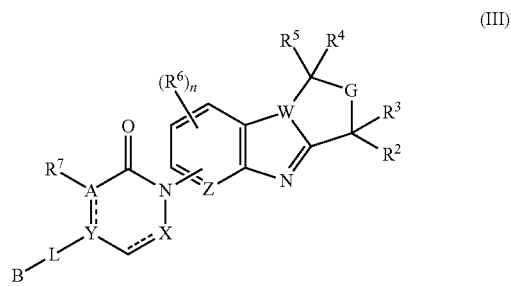

(III)

wherein the substituents are as described above. In a further embodiment, W is N. In yet another embodiment, Z is C or CH.

A further embodiment of the present invention relates to a compound of formula (IV):

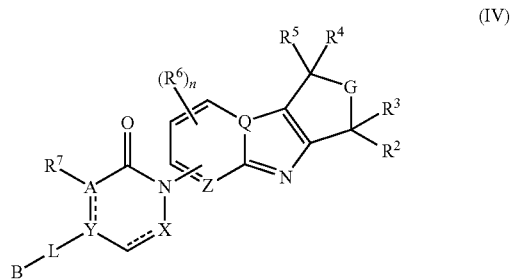

(IV)

wherein the substituents are as described above. In a further embodiment, Q is N. In yet another embodiment, Z is C or CH.

In accordance with one embodiment of the present invention, $R^1$ is optionally substituted $C_1$-$C_6$ alkyl, for example, methyl. In accordance with yet another embodiment of the present invention, $R^1$ is selected from the group consisting of H, —S(O)$_q$R$^4$, —C(O)R$^4$, —C(O)NR$^4$R$^5$, $C_1$-$C_6$ alkyl, $C_2$-$C_6$ alkenyl, and $C_2$-$C_6$ alkynyl.

In accordance with one embodiment of the present invention, n is 1.

In accordance with one embodiment of the present invention, n is 2.

In accordance with one embodiment of the present invention, X is N, CH, or CH$_2$.

In accordance with one embodiment of the present invention, Y is N, C, or CH. In yet another embodiment, Y is N.

In accordance with one embodiment of the present invention, L is a bond. In accordance with another embodiment of the present invention, L is —CH$_2$—O—. In accordance with another embodiment of the present invention, L is —CH$_2$—CH$_2$—.

In accordance with one embodiment of the present invention, B is aryl. In one embodiment, B is phenyl. In accordance with another embodiment of the present invention, B is heteroaryl. In one embodiment, B is pyridinyl, for example pyridin-2-yl or pyridin-3-yl, pyridazinyl, for example, pyridazin-3-yl, or pyrimidinyl, for example, pyrimidin-5-yl.

As described herein, B may be optionally substituted. In one embodiment, B is unsubstituted. In another embodiment, B is substituted with one substituent selected from trifluoromethyl, chloro, fluoro, methyl, and methanethio.

In accordance with one embodiment of the present invention, B is selected from the group consisting of phenyl, 4-(trifluoromethyl)phenyl, 4-(methylthio)-phenyl, 5-(trifluoromethyl)pyridin-2-yl, 2-(trifluoromethyl)-pyrimidin-5-yl, and 6-(trifluoromethyl)pyridazin-3-yl, 5-fluoro-pyridin-2-yl, 6-methylpyridin-3-yl, 6-(trifluoromethyl)pyridin-3-yl, 5-chloro-pyridin-2-yl, 2,4-dichloro-phenyl, 2,4-difluorophenyl, 4-chloro-phenyl, 4-chloro-2-fluoro-phenyl, 3,5-dichloro-pyridin-2-yl, 4-fluorophenyl, pyridin-2-yl, and 3,5-difluoro-pyridin-2-yl.

In accordance with one embodiment of the present invention the compound has the structure:

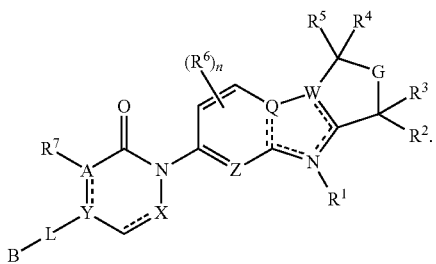

In accordance with one embodiment of the present invention, the compound has the structure

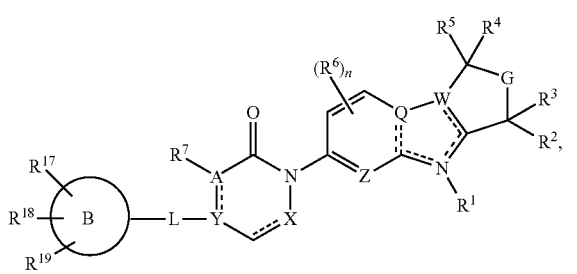

wherein R$^{17}$, R$^{18}$, and R$^{19}$ are individually selected from the group consisting of H, alkoxy, —S-alkyl, optionally substituted C$_1$-C$_6$ alkyl, halogen, —CF$_3$, and —CN.

Within these embodiments, the selection of a particular preferred substituent at any one of R$^1$-R$^{19}$, X, Y, G, A, L, B, Z, Q, and W does not affect the selection of a substituent at any of the others of R$^1$-R$^{19}$, X, Y, G, A, L, B, Z, Q, and W. That is, preferred compounds provided herein have any of the preferred substituents at any of the positions.

In accordance with one embodiment of the present invention, the compound is selected from

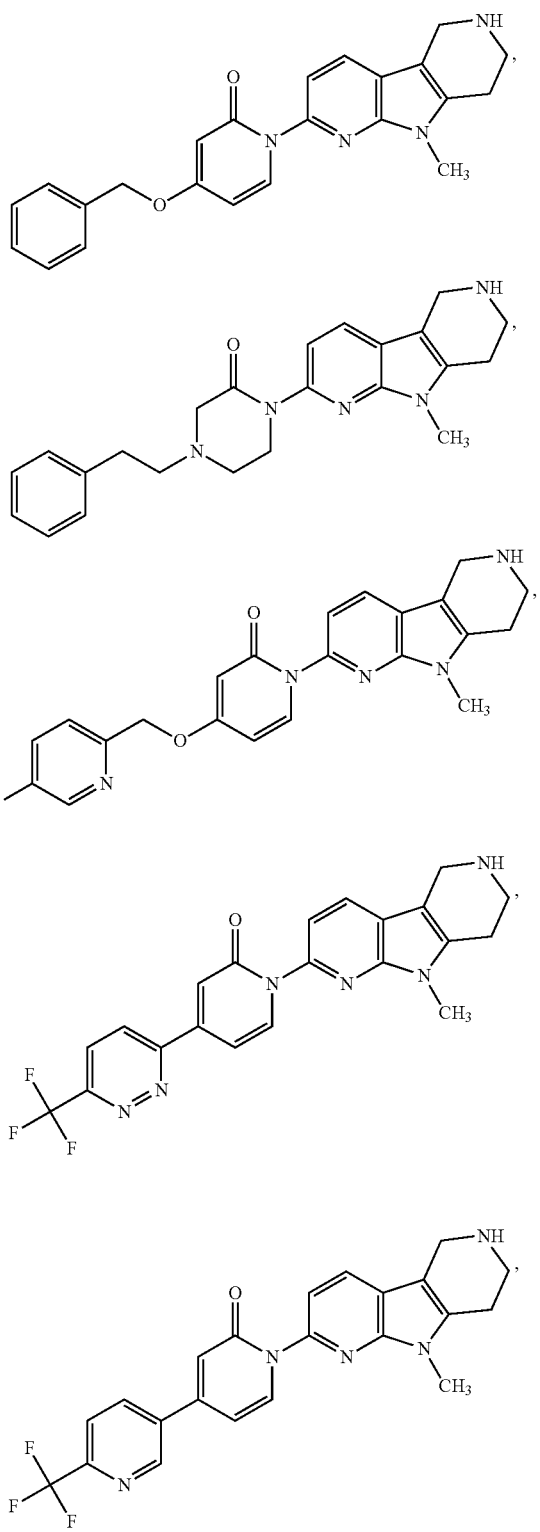

-continued
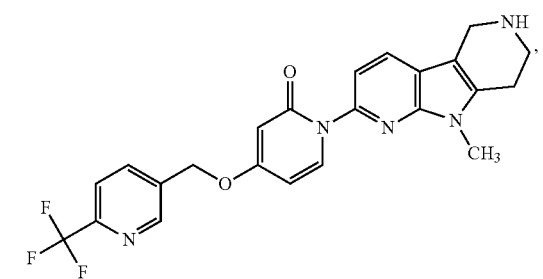
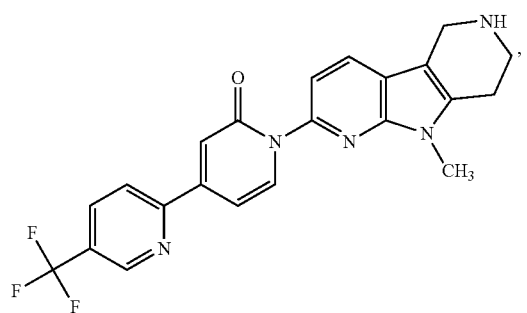
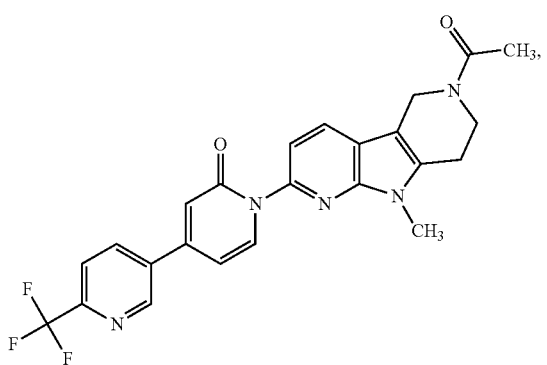
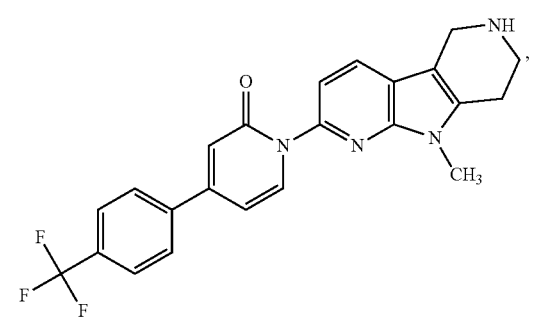
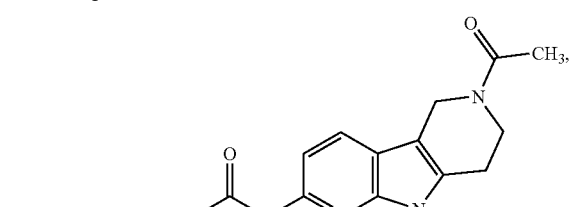
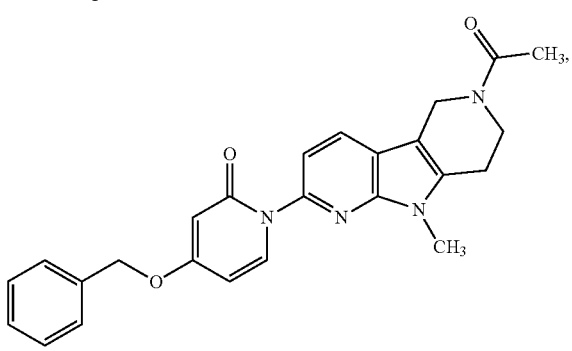
-continued
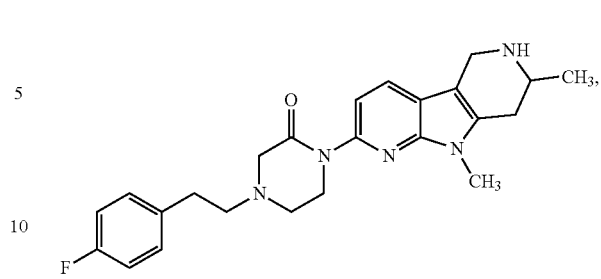
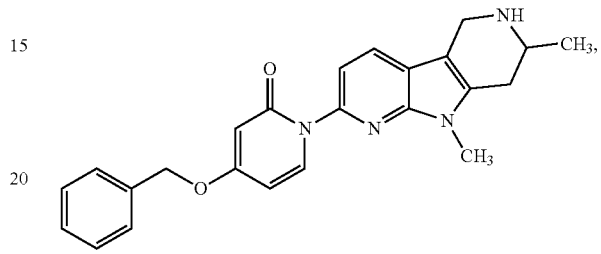
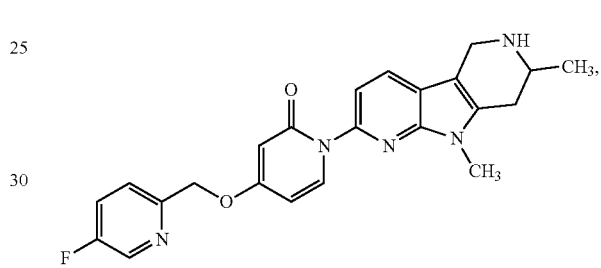
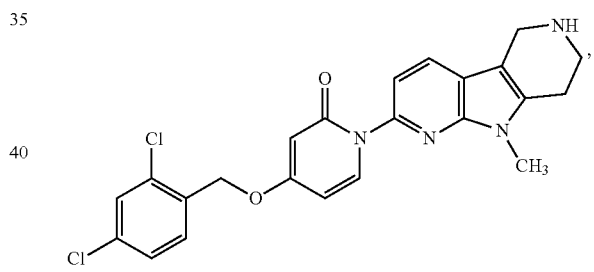
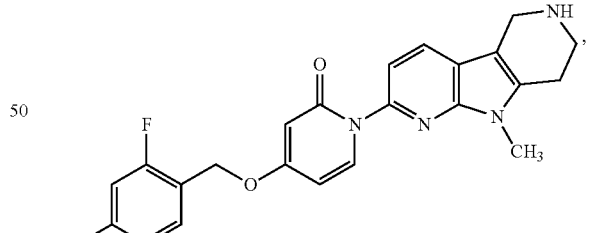
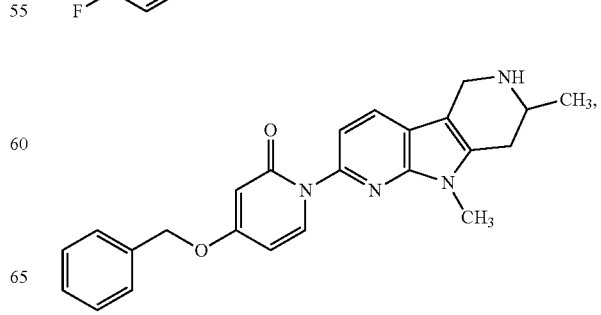

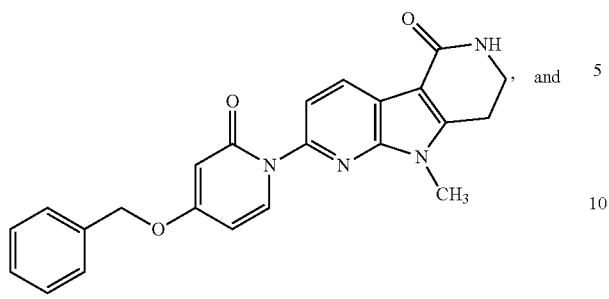
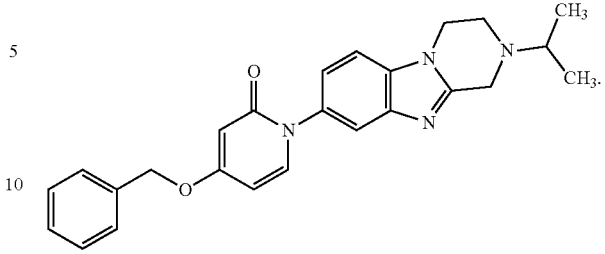
In accordance with a further embodiment of the present invention, the compound is selected from
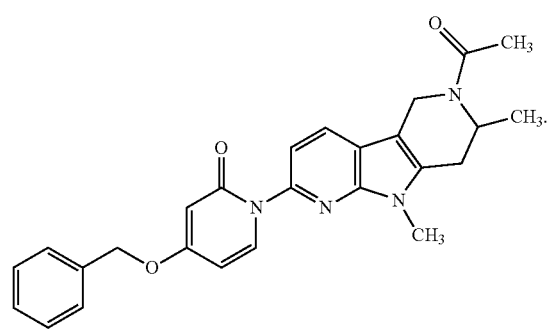
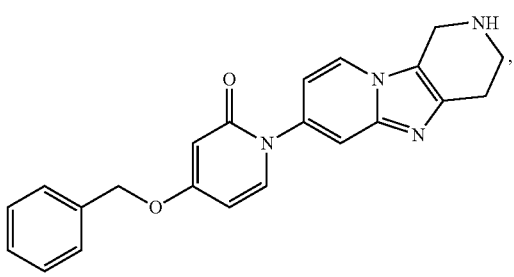
In accordance with another embodiment of the present invention, the compound is selected from
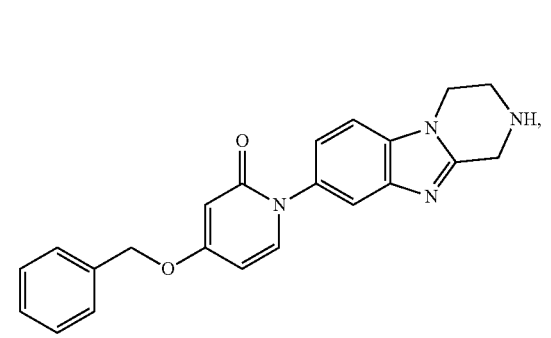
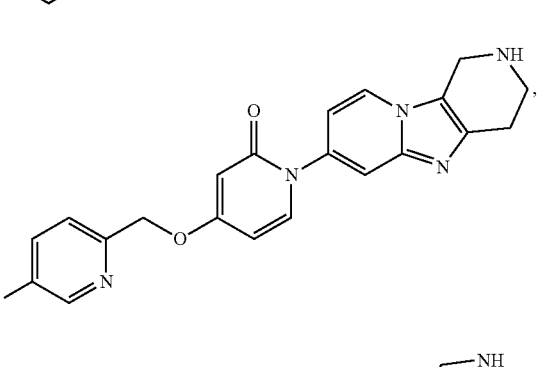
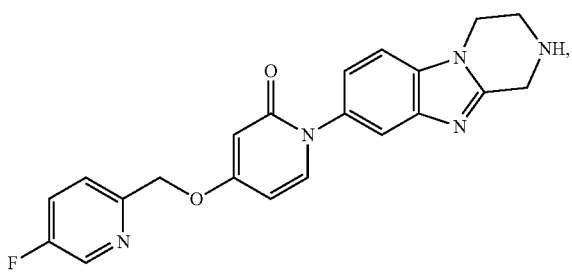
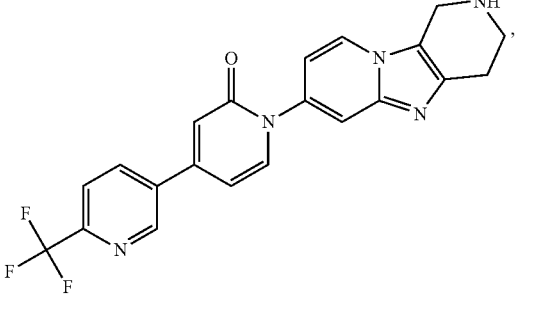
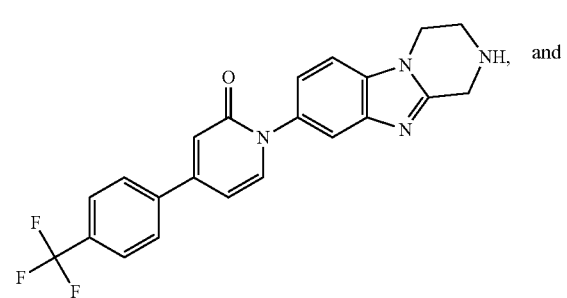
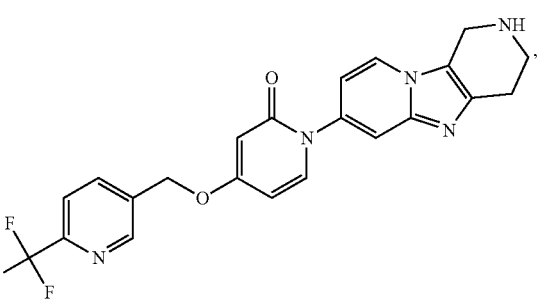

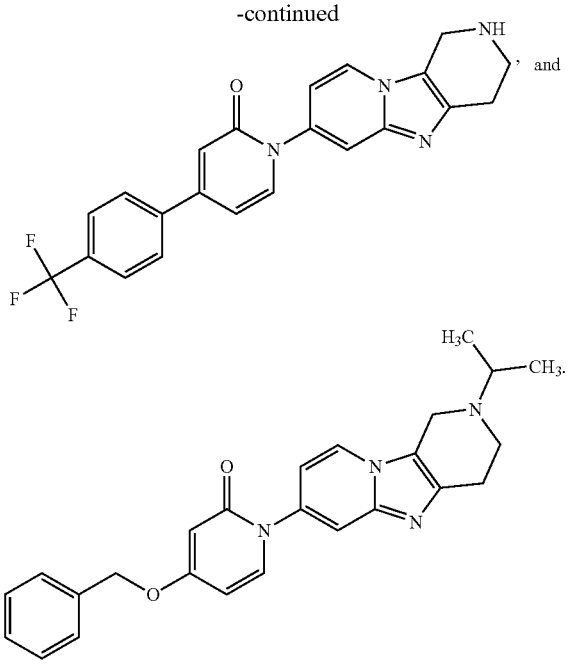

Table 1, infra, lists compounds representative of embodiments of the present invention.

One embodiment of the present invention relates to pharmaceutically acceptable salts, or non-salt forms, of any of the compounds of formula I described herein. In one embodiment, the salt is a HCl salt.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

The present invention also includes compounds of the present invention, wherein one or more of the atoms, e.g., C or H, are replaced by the corresponding radioactive isotopes of that atom (e.g., C replaced by $^{14}$C and H replaced by $^{3}$H), or a stable isotope of that atom (e.g., C replaced by $^{13}$C or H replaced by $^{2}$H). Radioisotopes of hydrogen, carbon, phosphorous, fluorine, iodine and chlorine include $^{3}$H, $^{14}$C, $^{35}$S, $^{18}$F, $^{32}$P, $^{33}$P, $^{125}$I, and $^{36}$Cl, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent. Such compounds have a variety of potential uses, e.g., as standards and reagents in determining the ability of a potential pharmaceutical to bind to neurotransmitter proteins. In addition, in the case of stable isotopes, such compounds may have the potential to favorably modify the biological properties, e.g., pharmacological and/or pharmacokinetic properties, of compounds of formula I. The details concerning selection of suitable sites for incorporating radioactive isotopes into the compounds are known to those skilled in the art.

Compounds of the present invention as described herein are useful as MCH-1 receptor antagonists. It may be found upon examination that compounds that are not presently excluded from the claims are not patentable to the inventors in this application. In that case, the exclusion of species and genera in applicants' claims are to be considered artifacts of patent prosecution and not reflective of the inventors' concept or description of their invention. The invention, in a compound aspect, is all compounds of formula I-IV, except those that are in the public's possession.

While it may be possible for compounds of the present invention to be administered as the raw chemical, it will often be preferable to present them as part of a pharmaceutical composition. Accordingly, another aspect of the present invention is a pharmaceutical composition containing a therapeutically effective amount of a compound of formula I-IV, or a pharmaceutically acceptable salt or solvate thereof, and a pharmaceutically acceptable carrier. The carrier must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts.

Solid carriers suitable for use in the composition of the invention include one or more substances which may also act as flavoring agents, lubricants, solubilizers, suspending agents, fillers, glidants, compression aides, binders, tablet-disintegrating agents, or encapsulating materials. In powders, the carrier may be a finely divided solid which is in admixture with a finely divided compound of the present invention. In tablets, the formula I-IV compound may be mixed with a carrier having the necessary compression properties in suitable proportions and compacted in the shape and size desired. Said powders and tablets may contain up to 99% by weight of the formula I-IV compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins.

Any pharmaceutically acceptable liquid carrier suitable for preparing solutions, suspensions, emulsions, syrups and elixirs may be employed in the composition of the invention. Compounds of formula I-IV may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

In one embodiment of the present invention, the pharmaceutical composition further comprises one or more other therapeutic adjuncts, e.g., other compounds effective in the treatment of obesity, anxiety, depression, or non-alcoholic fatty liver disease, that are known to persons of skill in the art. Such other therapeutic adjuncts are described below.

Another aspect of the present invention relates to a method of treating a disease or condition which is susceptible to treatment with an MCH-1 receptor antagonist. This method involves selecting a patient with a disease or condition which is susceptible to treatment with an MCH-1 receptor antagonist and administering to the patient a therapeutically effective amount of a compound of the present invention or a pharmaceutically acceptable salt thereof.

Diseases or conditions which are susceptible to treatment with an MCH-1 receptor antagonist in accordance with the present invention include, but are not limited to, obesity, general anxiety disorders, inflammatory bowel disease, social phobias, vertigo, obsessive-compulsive disorders, panic disorders, post-traumatic stress disorders, Parkinson's Disease Psychosis, schizophrenia, cognitive decline and defects in schizophrenia, Parkinson's Disease, Huntington's Chorea, presenile dementias, Alzheimer's Disease, psychological disorders, depression, substance abuse disorders, dementia associated with neurodegenerative disease, cognition deficits, and epilepsy (see PCT Publication No. WO 2007/010275, which is hereby incorporated by reference in its entirety).

As described above, the compounds of the present invention are useful as MCH-1 antagonists. As used in this invention, the term "antagonist" refers to a compound which binds to, and decreases the activity of, a receptor in the presence of an agonist.

As used herein, treatment means any manner in which one or more of the symptoms of a disease or disorder are ameliorated or otherwise beneficially altered. Treatment also encompasses any pharmaceutical use of the compositions herein, such as use for treating diseases or disorders in which MCH-1 receptor activity is implicated.

In another embodiment of the present invention, the above method further involves administering a therapeutically effective amount of one or more therapeutic adjuncts. Suitable therapeutic adjuncts include, but are not limited to, anti-obesity and/or anorectic agents, anti-anxiety agents, anti-depression agents, and anti-non-alcoholic fatty liver disease agents.

Suitable anti-obesity and/or anorectic adjuncts include, but are not limited to, phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist or inverse agonist, a melanin concentrating hormone receptor antagonist, a serotonin 5-$HT_6$ receptor antagonist, a serotonin 5-$HT_{2C}$ receptor agonist, the OB protein (hereinafter referred to as "leptin"), a leptin analog, a leptin receptor agonist, the amylin peptide, an amylin analog, an amylin receptor agonist, a neuropeptide Y receptor modulator, a galanin antagonist, or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Suitable anti-anxiety adjuncts include, but are not limited to, an allosteric modulator of the $GABA_A$ receptor (such as diazepam, lorazepam, or alprazolam), a serotonin 5-$HT_{1A}$ receptor partial agonist (such as buspirone), a selective serotonin reuptake inhibitor (SSRI, such as citalopram, escitalopram, fluoxetine, paroxetine, or sertraline), a serotonin-norepinephrine reuptake inhibitor (SNRI, such as duloxetine or venlafaxine), a monoamine neurotransmitter reuptake inhibitor of the tricyclic antidepressant (TCA) class (such as amitriptyline, desipramine, or imipramine), a combined serotonin reuptake inhibitor and 5-$HT_{2C}$ antagonist (such as trazodone), and an $H_1$ receptor antagonist (such as hydroxyzine).

Suitable anti-depression adjuncts include, but are not limited to, a serotonin 5-$HT_{1A}$ receptor partial agonist (such as buspirone), a selective serotonin reuptake inhibitor (SSRI, such as citalopram, escitalopram, fluoxetine, paroxetine, or sertraline), a serotonin-norepinephrine reuptake inhibitor (SNRI, such as duloxetine or venlafaxine), a monoamine neurotransmitter reuptake inhibitor of the tricyclic antidepressant (TCA) class (such as amitriptyline, desipramine, or imipramine), a combined serotonin reuptake inhibitor and 5-$HT_{2C}$ antagonist (such as trazodone), a noradrenergic and specific serotonergic antidepressant (NaSSA, such as mianserin or mirtazapine), a norepinephrine reuptake inhibitor (NRI, such as atomoxetine or Mazindol), a norepinephrine-dopamine reuptake inhibitor (NDRI, such as bupropion), and a monoamine oxidase inhibitor (MAOI, such as isocarboxazid or moclobemide).

Suitable anti-non-alcoholic fatty liver disease adjuncts include, but are not limited to, an AMP-activated protein kinase (AMPK) agonist (such as metformin), a peroxisome proliferator-activated receptor (PPAR) gamma activator (such as rosiglitazone, pioglitazone, or troglitazone), a HMG-CoA reductase inhibitor (such as atorvastatin or simvastatin), and a PDE4 inhibitor (such as pentoxifylline).

In one embodiment, the patient is a mammal. The term "mammal" is used in its dictionary sense. The term "mammal" includes, for example, mice, hamsters, rats, cows, sheep, pigs, goats, and horses, monkeys, dogs (e.g., *Canis familiaris*), cats, rabbits, guinea pigs, and primates, including humans.

The present invention also relates to a method of treating obesity in a subject in need of weight loss. This method involves selecting a patient in need of weight loss and administering to the patient a therapeutically effective amount of a compound of the present invention or a pharmaceutically acceptable salt thereof.

This method further involves administering an anti-obesity adjunct, as described above.

Yet another aspect of the present invention relates to a method of treating obesity in a subject who has experienced weight loss. This method involves selecting a patient who has experienced weight loss and administering to the patient a therapeutically effective amount of a compound of the present invention or a pharmaceutically acceptable salt thereof.

A further aspect of the present invention relates to a method of treating anxiety. This method involves selecting a patient with anxiety and administering to the patient a therapeutically effective amount of a compound of the present invention or a pharmaceutically acceptable salt thereof.

This method further involves administering an anti-anxiety adjunct, as described above.

The present invention also relates to a method of treating depression. This method involves selecting a patient with depression and administering to the patient a therapeutically effective amount of a compound of the present invention or a pharmaceutically acceptable salt thereof.

This method further involves administering an anti-depression adjunct, as described above.

Another aspect of the present invention relates to a method of treating non-alcoholic fatty liver disease. This method involves selecting a patient who has non-alcoholic fatty liver disease and administering to the patient a therapeutically effective amount of a compound of the present invention or a pharmaceutically acceptable salt thereof.

This method further involves administering an anti-non-alcoholic fatty liver disease adjunct, as described above.

Yet another aspect of the present invention relates to a method of treating inflammatory bowel disease. This method involves selecting a patient who has inflammatory bowel disease and administering to the patient a therapeutically effective amount of a compound of formula I or a pharmaceutically acceptable salt thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

The present invention also relates to a process for preparation of a product compound of formula I which includes treating a first intermediate compound of formula V:

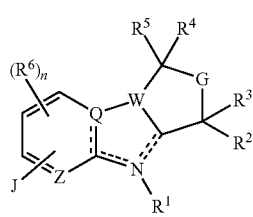

(V)

wherein J is a halogen, under conditions effective to form the product compound of formula I, wherein $R^1$-$R^{19}$, G, X, Y, A, L, B, Z, Q, and W are as defined above.

In one embodiment, treating involves reacting the first intermediate with a second intermediate having the structure:

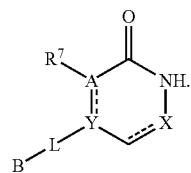

Compounds useful according to the invention may be prepared by the application or adaptation of known methods, by which is meant methods used heretofore or described in the literature, for example, those described by Larock, *Comprehensive Organic Transformations*, Wiley-VCH publishers, New York (1989), which is hereby incorporated by reference in its entirety.

A compound of formula I-IV including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxy, amino, imino, thio, or carboxy groups, where these are desired in the final product, to avoid their unwanted participation in the reactions. Conventional protecting groups may be used in accordance with standard practice and as described above.

The novel MCH-1 antagonists of formula I-IV of this invention can be prepared by the methods illustrated in the general reaction schemes as, for example, described below, or by modifications thereof, using readily available starting materials, reagents, and conventional synthesis procedures. In these reactions, it is also possible to make use of variants that are known in the art but are not mentioned here. Although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

Synthetic Methods

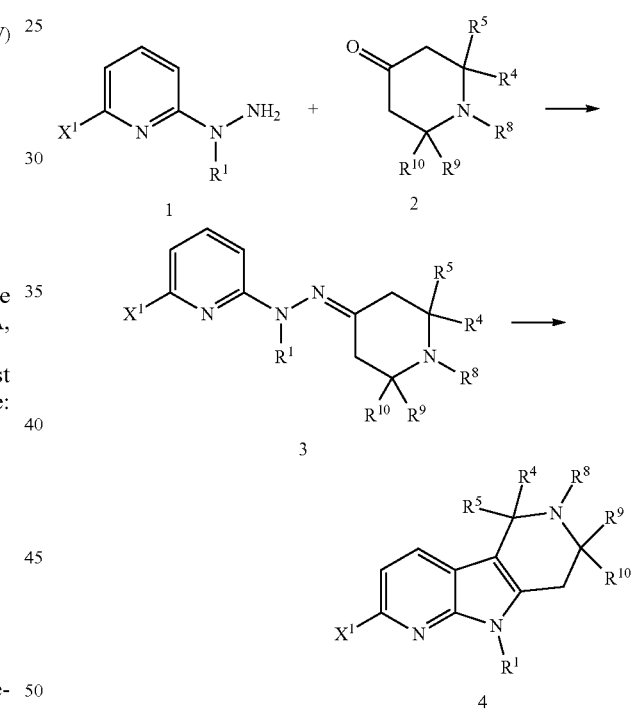

Scheme 1

Compounds of formula 3 (wherein $X^1$ is chlorine, bromine, or iodine; $R^1$ is H or alkyl; $R^8$ is H or a protecting group such as tert-butoxycarbonyl or benzyloxycarbonyl; and $R^4$, $R^5$, $R^9$, and $R^{10}$ are each independently H or alkyl) can be prepared from compounds of formula I (or a salt thereof, wherein $X^1$ is chlorine, bromine, or iodine and $R^1$ is H or alkyl) and piperidinone 2 (wherein $R^8$ is H or a protecting group such as tert-butoxycarbonyl or benzyloxycarbonyl and $R^4$, $R^5$, $R^9$, and $R^{10}$ are each independently H or alkyl) under ambient to heated conditions. In the case where $R^1$ is H, optional alkylation of compound 3 can provide compounds of formula 3 wherein $R^1$ is alkyl. Compounds of formula 4 (wherein $X^1$ is chlorine, bromine, or iodine; $R^1$ is H or alkyl; $R^8$ is H or a protecting group such as tert-butoxycarbonyl or benzyloxycarbonyl; and $R^4$, $R^5$, $R^9$, and $R^{10}$ are each independently H or alkyl) can be prepared from compounds of formula 3 under heated acidic conditions. In the case where $R^1$ is H, optional alkylation or protection of compound 4 can provide compounds of formula 4 wherein $R^1$ is alkyl or a protecting group such as tert-butoxycarbonyl, benzyloxycarbonyl or p-toluenesulfonyl. Optional removal of protecting group $R^8$ and reductive amination or alkylation can provide compounds of formula 4 wherein $R^8$ is alkyl.

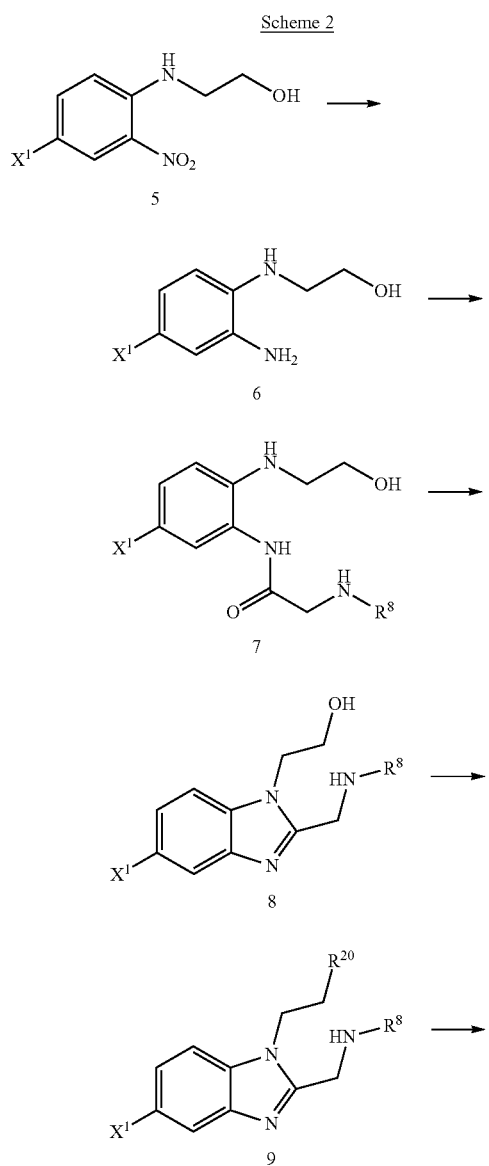

Compounds of formula 6 (wherein $X^1$ is chlorine, bromine, or iodine) can be prepared from compounds of formula 5 (wherein $X^1$ is chlorine, bromine, or iodine) under reducing conditions, such as heating with iron powder and ammonium chloride. Treatment of compounds of formula 6 with N-alkyl or N-protected glycine, a coupling agent such as HATU and a base such as i-Pr$_2$NEt can provide compounds of formula 7 (wherein $X^1$ is chlorine, bromine, or iodine and $R^8$ is alkyl or a protecting group such as tert-butoxycarbonyl or benzyloxycarbonyl). Treatment of compounds of formula 7 under heated acidic conditions can provide compounds of formula 8 (wherein $X^1$ is chlorine, bromine, or iodine and $R^8$ is H, alkyl, or a protecting group such as benzyloxycarbonyl). In the case where $R^8$ is H, optional alkylation or protection of compound 8 can provide compounds of formula 8 wherein $R^8$ is alkyl or a protecting group such as tert-butoxycarbonyl or benzyloxycarbonyl. The hydroxyl group on compounds of formula 8 can be converted to an appropriate leaving group to give compounds of formula 9. In the case where $R^{20}$ is mesylate, compounds of formula 8 can be treated with methanesulfonyl chloride and a base such as triethylamine under ambient conditions to give compounds of formula 9. Compounds of formula 10 (wherein $X^1$ is chlorine, bromine, or iodine and $R^8$ is H, alkyl, or a protecting group such as benzyloxycarbonyl) can be prepared from compounds of formula 9 under heated acidic conditions. In the case where $R^8$ is H, optional alkylation or protection of compound 10 can provide compounds of formula 10 wherein $R^8$ is alkyl or a protecting group such as tert-butoxycarbonyl or benzyloxycarbonyl.

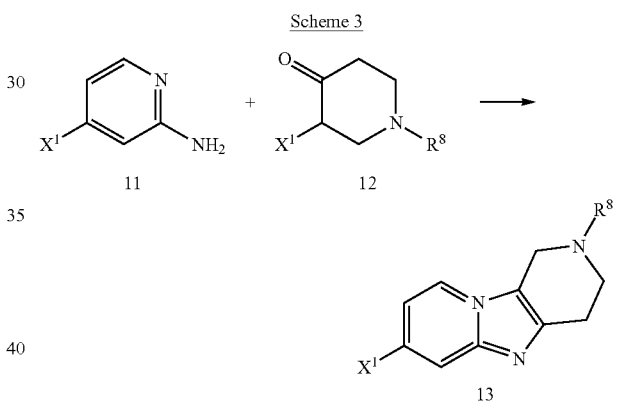

Compounds of formula 13 (wherein $X^1$ is chlorine, bromine, or iodine and $R^8$ is alkyl or a protecting group such as tert-butoxycarbonyl or benzyloxycarbonyl) can be prepared from compounds of formula II (wherein $X^1$ is chlorine, bromine, or iodine) and compounds of formula 12 (wherein $R^8$ is alkyl or a protecting group such as tert-butoxycarbonyl or benzyloxycarbonyl) under heated conditions. In the case where $R^8$ is a protecting group, deprotection and optional alkylation can provide compounds of formula 13 wherein $R^8$ is H or alkyl.

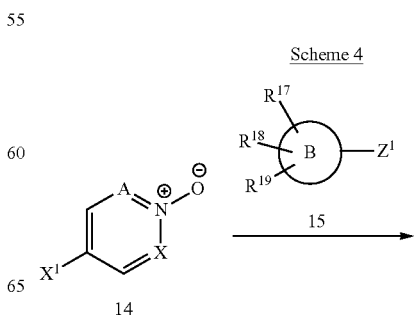

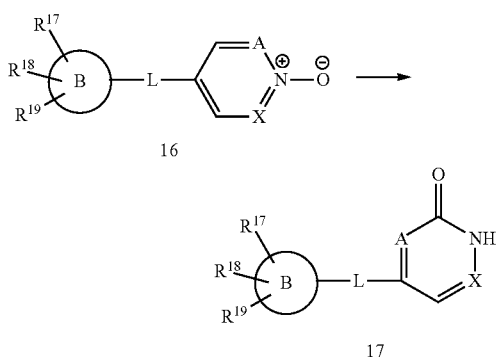

Compounds of formula 17 (wherein B is aryl, heteroaryl, heterocyclyl, or cycloalkyl; $R^{17}$, $R^{18}$, and $R^{19}$ are each independently selected from H, alkoxy, S-alkyl, alkyl, halo, —$CF_3$, and —CN; A is CH; X is CH; and L is —$CH_2$—O— or a bond) can be prepared by treating compounds of formula 14 (wherein $X^1$ is chlorine, bromine or iodine; A is CH; and X is CH) with compounds of formula 15 (wherein B is aryl, heteroaryl, heterocyclyl, or cycloalkyl; $R^{17}$, $R^{18}$, and $R^{19}$ are each independently selected from H, —O-alkyl, alkyl, halo, —$CF_3$, and —CN; $Z^1$ is $B(OH)_2$, $B(OR^{21})_2$, $SnR^{21}{}_3$ or the like and $R^{21}$ is alkyl), a catalyst such as palladium(0), and a base such as potassium carbonate to give compounds of formula 16, wherein L is a direct bond. Alternatively, in the case where $Z^1$ is —$CH_2$—OH and B is aryl, heteroaryl, heterocyclyl, or cycloalkyl, compounds of formula 15 can be treated with a base such as sodium hydride and compounds of formula 14 under heated conditions to give compounds of formula 16, wherein L is —$CH_2$—O—. In turn, compounds of formula 16 can be treated with acetic anhydride under heated conditions followed by methanol and water or methanol and sodium hydroxide under ambient to heated conditions to provide compounds of formula 17, wherein L is —$CH_2O$— or a direct bond.

Scheme 5

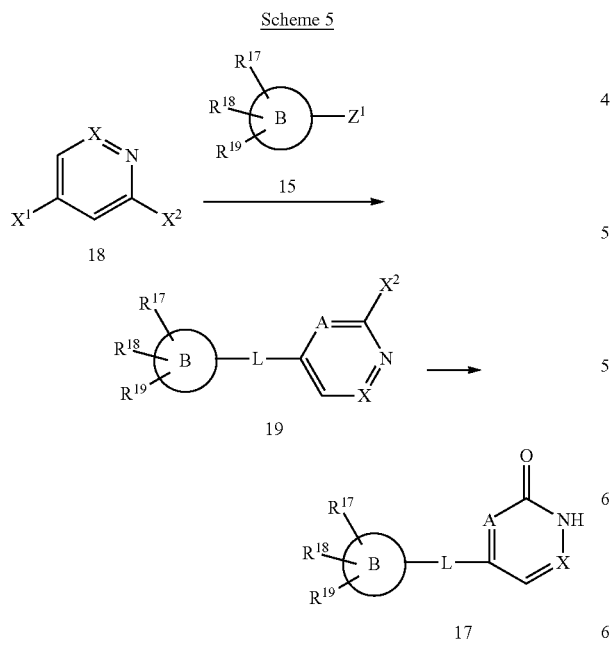

Alternatively, compounds of formula 17 (wherein B is aryl, heteroaryl, heterocyclyl, or cycloalkyl; $R^{17}$, $R^{18}$, and $R^{19}$ are each independently selected from H, alkoxy, —S-alkyl, alkyl, halo, —$CF_3$, and —CN; A is CH or N; X is CH; and L is —$CH_2$—$CH_2$—, or a bond) can be prepared by treating compounds of formula 18 (wherein $X^1$ is chlorine, bromine or iodine; $X^2$ is —O—$CH_3$ or chlorine; A is CH or N; and X is CH) with compounds of formula 15 (wherein $Z^1$, is —CH=CH—$B(OR^{21})_2$, $B(OH)_2$, $B(OR^{21})_2$, $SnR^{21}{}_3$ or the like and $R^{21}$ is alkyl), a catalyst such as palladium(0), and a base such as potassium carbonate to give compounds of formula 19, wherein L is —CH=CH— or a direct bond, in accordance with $Z^1$. In the case where L is —CH=CH—, compounds of formula 19 can be treated with palladium on carbon under an atmosphere of hydrogen to give compounds of formula 19, wherein L is —$CH_2CH_2$—. Alternatively, in the case where $Z^1$ is —$CH_2$—OH, compounds of formula 18 can be treated with compounds of formula 15, a catalyst such as copper iodide, a ligand such as 3,4,7,8-tetramethylphenanthroline and a base such as cesium carbonate under heated conditions to give compounds of formula 19, wherein L is —$CH_2$—O—. In turn, when L is —$CH_2$—$CH_2$—, —$CH_2$—O— or a direct bond, compounds of formula 19 can be heated under acid conditions to provide compounds of formula 17, wherein L is —$CH_2$—$CH_2$—, —$CH_2$—O— or a direct bond, respectively.

Scheme 6

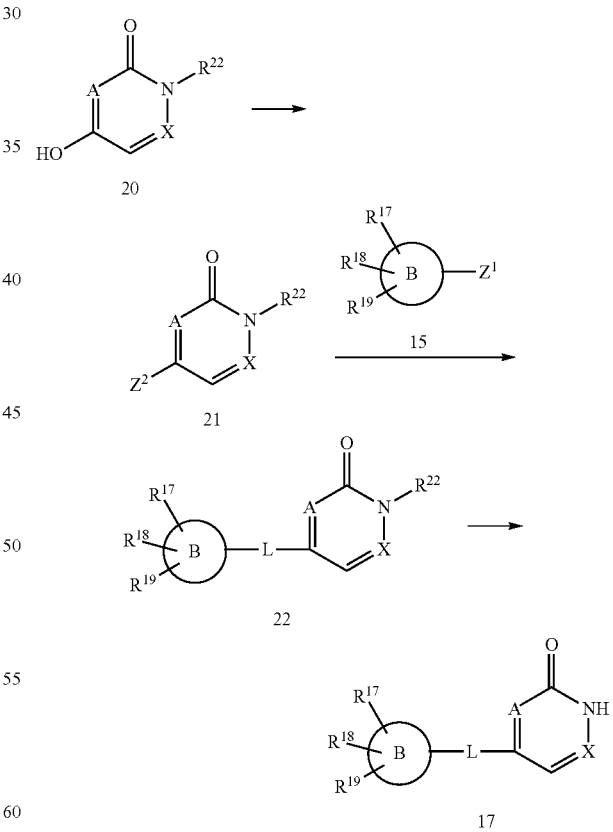

Alternatively, compounds of formula 17 (wherein B is aryl, heteroaryl, heterocyclyl, or cycloalkyl; $R^{17}$, $R^{18}$, and $R^{19}$ are each independently selected from H, alkoxy, S-alkyl, alkyl, halo, —$CF_3$, and —CN; A is CH; X is N; and L is —$CH_2$—O— or a bond) can be prepared from compounds of formula 20 (wherein A is CH; X is N; and $R^{22}$ is a protecting group such as tetrahydropyran-2-yl). The hydroxyl group on compound 20 can be converted to an appropriate activating group to give compounds of formula 21. In the case where $Z^2$ is triflate, compounds of formula 20 can be treated with trifluoromethylsulfonic anhydride or N-phenyl trifluoromethanesulfonamide and a base such as triethylamine, pyridine or lithium bis(trimethylsilyl)amide under cooled conditions to give compounds of formula 21. Treatment of compounds of formula 21 with compounds of formula 15 (wherein B is aryl, heteroaryl, heterocyclyl, or cycloalkyl; $R^{17}$, $R^{18}$, and $R^{19}$ are each independently selected from H, alkoxy, S-alkyl, alkyl, halo, —$CF_3$, and —CN; $Z^1$ is $B(OH)_2$, $B(OR^{21})_2$, $SnR^{21}{}_3$ or the like, and $R^{21}$ is alkyl), a catalyst such as palladium(0), and a base such as potassium carbonate under heated conditions can provide compounds of formula 22, wherein L is a direct bond. Alternatively, in the case where $Z^1$ is —$CH_2$—Br, compounds of formula 15 can be treated with compounds of formula 20 and a base such as potassium carbonate to give compounds of formula 22, wherein L is —$CH_2$—O—. Removal of the protecting group $R^{22}$ on compound 22 can provide compounds of formula 17, wherein L is —$CH_2$—O— or a bond.

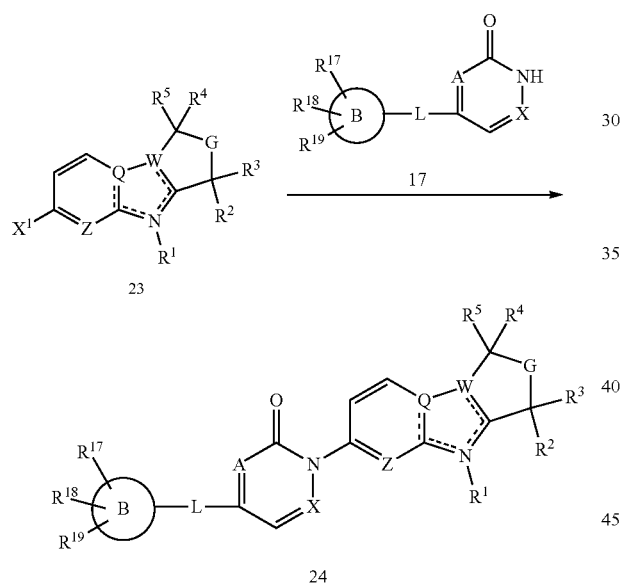

Scheme 7

Compounds of formula 24 (wherein B is aryl, heteroaryl, heterocyclyl, or cycloalkyl; $R^{17}$, $R^{18}$, and $R^{19}$ are each independently selected from H, alkoxy, —S-alkyl, alkyl, halo, —$CF_3$, and —CN; L is —$CH_2$—$CH_2$—, —$CH_2$—O— or a bond; A is CH or N; X is CH or N; Z is CH or N and W and Q are each C or N, wherein one of Q, W, and Z is N; G is —$NR^8$—$CH_2$— or —$CH_2$—$NR^8$—; $R^8$ is H, alkyl, or a protecting group such as tert-butoxycarbonyl or benzyloxycarbonyl; $R^1$ is optionally present and, if present, is alkyl or a protecting group such as tert-butoxycarbonyl, benzyloxycarbonyl or p-toluenesulfonyl; and $R^2$, $R^3$, $R^4$, and $R^5$ are each independently H or alkyl) can be prepared by treating compounds of formula 23 (wherein Z is CH or N and W and Z are each C or N, wherein one of Q, W, and Z is N; G is —$NR^8$—$CH_2$— or —$CH_2$—$NR^8$—; $R^8$ is H, alkyl, or a protecting group such as tert-butoxycarbonyl or benzyloxycarbonyl; $R^1$ is optionally present and, if present, is alkyl or a protecting group such as tert-butoxycarbonyl, benzyloxycarbonyl or p-toluenesulfonyl; and $R^2$, $R^3$, $R^4$, and $R^5$ are each independently H or alkyl) under heated conditions with a catalyst such as copper iodide, a ligand such as trans-1,2-diaminocyclohexane or 8-hydroxyquinoline, a base such as potassium carbonate, cesium carbonate or potassium phosphate and compounds of formula 17 (wherein B is aryl, heteroaryl, heterocyclyl, or cycloalkyl; $R^{17}$, $R^{18}$, and $R^{19}$ are each independently selected from H, alkoxy, —S-alkyl, alkyl, halo, —$CF_3$, and —CN; L is —$CH_2$—$CH_2$—, —$CH_2$—O— or a bond; A is CH or N; and X is CH or N). In the case where $R^8$ is a protecting group, the protecting group can be removed to give compounds of formula 24 wherein $R^8$ is H. In the case where $R^8$ is H, reductive amination or alkylation can provide compounds of formula 24, wherein $R^8$ is an alkyl group. Additionally, in the case where $R^1$ is a protecting group, the protecting group can be removed to give compounds of formula 24 wherein $R^1$ is H.

Scheme 8

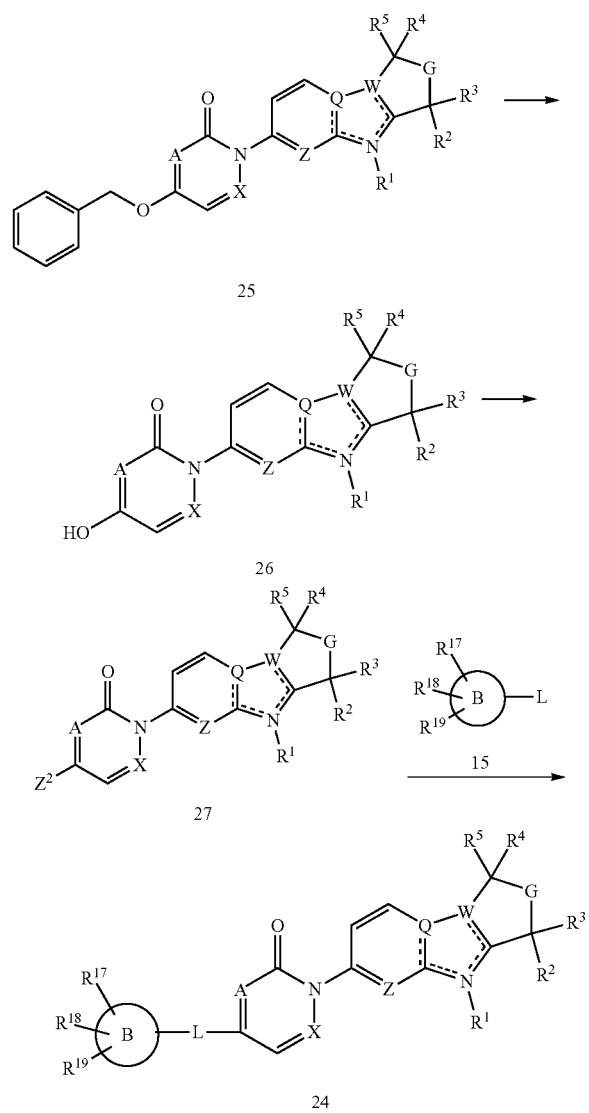

Compounds of formula 25 (wherein A is CH or N; X is CH or N; Z is CH or N and W and Q are each C or N, wherein one of Q, W, and Z is N; G is —$NR^8$—$CH_2$— or —$CH_2$—$NR^8$—; $R^8$ is H, alkyl, or a protecting group such as tert-butoxycarbonyl or benzyloxycarbonyl; $R^1$ is optionally present and, if present, is alkyl or a protecting group such as tert-butoxycarbonyl, benzyloxycarbonyl, or p-toluenesulfonyl; and $R^2$, $R^3$, $R^4$, and $R^5$ are each independently H or alkyl) can be treated with hydrogen and a catalyst such as palladium on carbon to provide compounds of formula 26. The hydroxyl group on compounds of formula 26 can be converted to an appropriate activating group to give compounds of formula 27. In the case where $Z^2$ is triflate, compounds of formula 26 can be treated with trifluoromethylsulfonic anhydride or N-phenyl trifluoromethanesulfonamide and a base such as pyridine or lithium bis(trimethylsilyl)amide under cooled conditions to give compounds of formula 27. Treatment of compounds of formula 27 with compounds of formula 15 (wherein B is aryl, heteroaryl, heterocyclyl, or cycloalkyl; $R^{17}$, $R^{18}$, and $R^{19}$ are each independently selected from H, alkoxy, —S-alkyl, alkyl, halo, —$CF_3$, and —CN; $Z^1$ is —CH═CH—B($OR^{21}$)$_2$, B(OH)$_2$, B($OR^{21}$)$_2$, $SnR^{21}{}_3$ or the like and $R^{21}$ is alkyl), a catalyst such as palladium(0), and a base such as potassium carbonate under heated conditions can provide compounds of formula 24, wherein L is —CH═CH— or a direct bond. In the case where L is —CH═CH—, compounds of formula 24 can be treated with palladium on carbon under an atmosphere of hydrogen to give compounds of formula 24, where L is —$CH_2CH_2$—.

Scheme 9

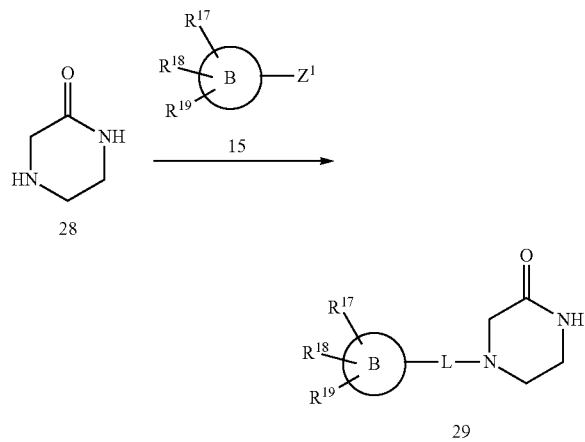

Compounds of formula 29 (wherein B is aryl, heteroaryl, heterocyclyl, or cycloalkyl; $R^{17}$, $R^{18}$, and $R^{19}$ are each independently selected from H, alkoxy, —S-alkyl, alkyl, halo, —$CF_3$, and —CN; and L is —$CH_2$—$CH_2$—) can be prepared by treating piperazin-2-one 28 with compounds of formula 15 (wherein $Z^1$ is —$CH_2$—$CH_2$—$X^1$; and $X^1$ is a leaving group such as chlorine, bromine, iodine or the like) and a base such as di-isopropylamine to give compounds of formula 29, wherein L is —$CH_2$—$CH_2$—.

Scheme 10

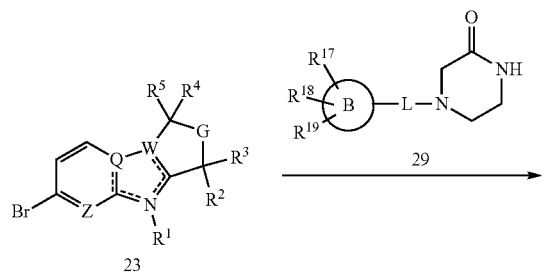

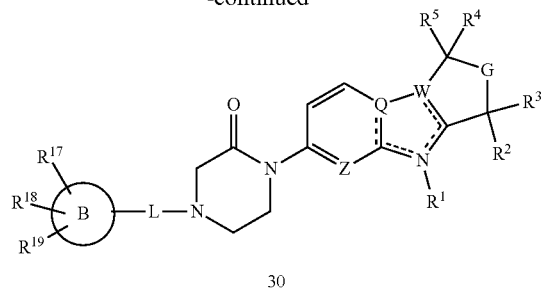

Compounds of formula 30 (wherein B is aryl, heteroaryl, heterocyclyl, or cycloalkyl; $R^{17}$, $R^{18}$, and $R^{19}$ are each independently selected from H, alkoxy, —S-alkyl, alkyl, halo, —$CF_3$, and —CN; L is —$CH_2$—$CH_2$—; Z is CH or N and W and Q are each C or N, wherein one of Q, W, and Z is N; G is —$NR^8$—$CH_2$— or —$CH_2$—$NR^8$—; $R^8$ is H, alkyl, or a protecting group such as tert-butoxycarbonyl or benzyloxycarbonyl; $R^1$ is optionally present and, if present, is alkyl or a protecting group such as tert-butoxycarbonyl, benzyloxycarbonyl or p-toluenesulfonyl; and $R^2$, $R^3$, $R^4$ and $R^5$ are each independently H or alkyl) can be prepared by treating compounds of formula 23 (wherein Z is CH or N and W and Q are each C or N, wherein one of Q, W, and Z is N; G is —$NR^8$—$CH_2$— or —$CH_2$—$NR^8$—; $R^8$ is H, alkyl, or a protecting group such as tert-butoxycarbonyl or benzyloxycarbonyl; $R^1$ is optionally present and, if present, is alkyl or a protecting group such as tert-butoxycarbonyl, benzyloxycarbonyl or p-toluenesulfonyl; and $R^2$, $R^3$, $R^4$, and $R^5$ are each independently H or alkyl) under heated conditions with a catalyst such as copper iodide, a ligand such as trans-1,2-bis(methylamino)cyclohexane or 8-hydroxyquinoline, a base such as potassium carbonate, cesium carbonate or potassium phosphate and compounds of formula 29 (wherein B is aryl, heteroaryl, heterocyclyl, or cycloalkyl; $R^{17}$, $R^{18}$, and $R^{19}$ are each independently selected from H, alkoxy, —S-alkyl, alkyl, halo, —$CF_3$, and —CN; and L is —$CH_2$—$CH_2$—). In the case where $R^8$ is a protecting group, the protecting group can be removed to give compounds of formula 30 wherein $R^8$ is H. In the case where $R^8$ is H, reductive amination or alkylation can provide compounds of formula 30, wherein $R^8$ is an alkyl group. Additionally, in the case where $R^1$ is a protecting group, the protecting group can be removed to give compounds of formula 30 wherein $R^1$ is H.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining one or more active ingredients useful in treating the disease. A kit may provide (alone or in combination with a pharmaceutically acceptable diluent or carrier) the compounds of formula I and an additional active ingredient (alone or in combination with diluent or carrier), as described above.

The products according to the present invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The formulations of compounds of formula I-IV include those suitable for oral, parenteral (including subcutaneous, intradermal, intramuscular, intraperitoneal, intravenous, and intraarticular), rectal, colonic, and topical (including dermal, buccal, nasal, sublingual, and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I-IV or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Molded tablets may be made by molding in a suitable machine a mixture of the powdered compound moistened with an inert liquid diluent. The tablets may optionally be coated or scored and may be formulated so as to provide sustained, delayed, or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I-IV to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.001 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The amount of active ingredient that may be combined with the carrier materials to produce a single dosage form will vary depending upon the host treated and the particular mode of administration. For example, a formulation intended for the oral administration of humans may vary from about 5 to about 95% of the total composition.

A dosage unit (e.g. an oral dosage unit) can include from, for example, 0.01 to 0.1 mg, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 0.01 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

For additional information about pharmaceutical compositions and their formulation, see, for example, Remington, *The Science and Practice of Pharmacy*, 20th Edition (2000), which is hereby incorporated by reference in its entirety.

The compounds of formula 1-IV can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The compounds of formula I-IV can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. PCT Publication No. WO 97/11682, which is hereby incorporated by reference in its entirety) via a liposomal formulation (see, e.g., European Patent EP 736299 and PCT Publication Nos. WO 99/59550 and WO 97/13500, which are hereby incorporated by reference in their entirety), via formulations described in PCT Publication No. WO 03/094886, which is hereby incorporated by reference in its entirety, or in some other form. The compounds of formula I-IV can also be administered transdermally (i.e. via reservoir-type or matrix-type patches, microneedles, thermal poration, hypodermic needles, iontophoresis, electro-poration, ultrasound or other forms of sonophoresis, jet injection, or a combination of any of the preceding methods (Prausnitz et al., *Nature Reviews Drug Discovery* 3:115 (2004), which is hereby incorporated by reference in its entirety)). The compounds can be administered locally, for example, at the site of injury to an injured blood vessel. The compounds can be coated on a stent. The compounds can be administered using high-velocity transdermal particle injection techniques using the hydrogel particle formulation described in U.S. Patent Publication No. 20020061336, which is hereby incorporated by reference in its entirety. Additional particle formulations are described in PCT Publication Nos. WO 00/45792, WO 00/53160, and WO 02/19989, which are hereby incorporated by reference in their entirety. An example of a transdermal formulation containing plaster and the absorption promoter dimethylisosorbide can be found in PCT Publication No. WO 89/04179, which is hereby incorporated by reference in its entirety. PCT Publication No. WO 96/11705, which is hereby incorporated by reference in its entirety, provides formulations suitable for transdermal administration.

The compounds can be administered in the form a suppository or by other vaginal or rectal means. The compounds can be administered in a transmembrane formulation as described in PCT Publication No. WO 90/07923, which is hereby incorporated by reference in its entirety. The compounds can be administered non-invasively via the dehydrated particles described in U.S. Pat. No. 6,485,706, which is hereby incorporated by reference in its entirety. The compound can be administered in an enteric-coated drug formulation as described in PCT Publication No. WO 02/49621, which is hereby incorporated by reference in its entirety. The compounds can be administered intranasally using the formulation described in U.S. Pat. No. 5,179,079, which is hereby incorporated by reference in its entirety. Formulations suitable for parenteral injection are described in PCT Publication No. WO 00/62759, which is hereby incorporated by reference in its entirety. The compounds can be administered using the casein formulation described in U.S. Patent Publication No. 20030206939 and PCT Publication No. WO 00/06108, which are hereby incorporated by reference in their entirety. The compounds can be administered using the particulate formulations described in U.S. Patent Application Publication No. 20020034536, which is hereby incorporated by reference in its entirety.

The compounds, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion.

Pulmonary formulations may also include surfactants which include but are not limited to bile salts and those described in U.S. Pat. No. 6,524,557 and references therein, which is hereby incorporated by reference in its entirety. The surfactants described in U.S. Pat. No. 6,524,557, which is hereby incorporated by reference in its entirety, e.g., a $C_8$-$C_{16}$ fatty acid salt, a bile salt, a phospholipid, or alkyl saccharide are advantageous in that some of them also reportedly enhance absorption of the compound in the formulation.

Also suitable in the invention are dry powder formulations comprising a therapeutically effective amount of active compound blended with an appropriate carrier and adapted for use in connection with a dry-powder inhaler. Absorption enhancers that can be added to dry powder formulations of the present invention include those described in U.S. Pat. No. 6,632,456, which is hereby incorporated by reference in its entirety. PCT Publication No. WO 02/080884, which is hereby incorporated by reference in its entirety, describes new methods for the surface modification of powders. Aerosol formulations may include U.S. Pat. No. 5,230,884, U.S. Pat. No. 5,292,499, PCT Publication No. WO 017/8694, PCT Publication No. WO 01/78696, U.S. Patent Application Publication No. 2003019437, U.S. Patent Application Publication No. 20030165436, and PCT Publication No. WO 96/40089 (which includes vegetable oil), which are hereby incorporated by reference in their entirety. Sustained release formulations suitable for inhalation are described in U.S. Patent Application Publication Nos. 20010036481A1, 20030232019A1, and 20040018243A1 as well as in PCT Publication Nos. WO 01/13891, WO 02/067902, WO 03/072080, and WO 03/079885, which are hereby incorporated by reference in their entirety.

Pulmonary formulations containing microparticles are described in PCT Publication No. WO 03/015750, U.S. Patent Application Publication No. 20030008013, and PCT Publication No. WO 00/00176, which are hereby incorporated by reference in their entirety. Pulmonary formulations containing stable glassy state powder are described in U.S. Patent Application Publication No. 20020141945 and U.S. Pat. No. 6,309,671, which are hereby incorporated by reference in their entirety. Other aerosol formulations are described in EP 1338272A1, PCT Publication No. WO 90/09781, U.S. Pat. No. 5,348,730, U.S. Pat. No. 6,436,367, PCT Publication No. WO 91/04011, and U.S. Pat. No. 6,294,153, which are hereby incorporated by reference in their entirety, and U.S. Pat. No. 6,290,987, which is hereby incorporated by reference in its entirety, describes a liposomal based formulation that can be administered via aerosol or other means.

Powder formulations for inhalation are described in U.S. Patent Application Publication No. 20030053960 and PCT Publication No. WO 01/60341, which are hereby incorporated by reference in their entirety. The compounds can be administered intranasally as described in U.S. Patent Application Publication No. 20010038824, which is hereby incorporated by reference in its entirety.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy, which are hereby incorporated by reference in their entirety.

Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington, which are hereby incorporated by reference in their entirety.

Compounds of formula I-IV can be incorporated into a liposome to improve half-life. Compounds of formula I-IV can also be conjugated to polyethylene glycol (PEG) chains. Methods for pegylation and additional formulations containing PEG-conjugates (i.e. PEG-based hydrogels, PEG modified liposomes) can be found in Harris et al., *Nature Reviews Drug Discovery*, 2:214-221 (2003) and the references therein, which are hereby incorporated by reference in their entirety. Compounds of formula I-IV can also be administered via a nanocochleate or cochleate delivery vehicle (BioDelivery Sciences International, Raleigh, N.C.). Compounds of formula I can also be delivered using nanoemulsion formulations.

EXAMPLES

The Examples set forth below are for illustrative purposes only and are not intended to limit, in any way, the scope of the present invention.

Example 1

Analytical Methods and Materials

Unless otherwise noted, reagents and solvents were used as received from commercial suppliers. Proton nuclear magnetic resonance (NMR) spectra were obtained on Bruker spectrometers at 300, 400 or 500 MHz. Spectra are given in ppm (δ) and coupling constants, J, are reported in Hertz. Tetramethylsilane (TMS) was used as an internal standard. Mass spectra were collected using either a Finnigan LCQ Duo LCMS ion trap electrospray ionization (ESI) or a mass Varian 1200L single quadrapole mass spectrometer (ESI). High performance liquid chromatograph (HPLC) analyses were obtained using a Luna C18(2) column (250×4.6 mm, Phenomenex) or a Gemini C18 column (250×4.6 mm, Phenomenex) with UV detection at 254 nm or 223 nm using a standard solvent gradient program (Method A, Method B or Method C).

Method A:

| Time (min) | Flow (mL/min) | % A | % B |
|---|---|---|---|
| 0.0 | 1.0 | 90.0 | 10.0 |
| 20 | 1.0 | 10.0 | 90.0 |
| 30 | 1.0 | 10.0 | 90.0 |

A = Water with 0.05% Trifluoroacetic Acid
B = Acetonitrile with 0.05% Trifluoroacetic Acid Method B:

| Time (min) | Flow (mL/min) | % A | % B |
|---|---|---|---|
| 0.0 | 1.0 | 98.0 | 2.0 |
| 20 | 1.0 | 2.0 | 98.0 |
| 25 | 1.0 | 2.0 | 98.0 |

A = Water with 0.025% Trifluoroacetic Acid
B = Acetonitrile with 0.025% Trifluoroacetic Acid Method C:

| Time (min) | Flow (mL/min) | % A | % B |
|---|---|---|---|
| 0.0 | 1.0 | 98.0 | 2.0 |
| 20 | 1.0 | 10.0 | 90.0 |
| 30 | 1.0 | 10.0 | 90.0 |

A = Water with 0.025% Trifluoroacetic Acid
B = Acetonitrile with 0.025% Trifluoroacetic Acid

Example 2

Preparation of 4-(Benzyloxy)-1-(9-methyl-5,7,8,9-tetrahydro-6H-pyrido[3',4':4,5]pyrrolo[2,3-b]pyridin-2-yl)pyridin-2(1H)-one dihydrochloride a) 2-Bromo-6-hydrazinylpyridine

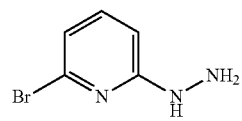

Chemical Formula: $C_5H_6BrN_3$
Exact Mass: 186.97
Molecular Weight: 188.03

Hydrazine (27 mL, 83 mmol) was added to 2,6-dibromopyridine (20 g, 84 mmol), and the resulting suspension was heated at 70° C. for 30 min. The solution was cooled to 50° C. and diluted with $H_2O$ (150 mL). The resulting solids were stirred for 2 h, collected by filtration, and washed with $H_2O$ (350 mL) to provide the title compound (13 g, 83%) as a white solid: $^1H$ NMR (300 MHz, DMSO-$d_6$) δ 7.87 (s, 1H), 7.34 (overlapping dd, J=7.8 Hz, 1H), 6.68 (d, J=7.8 Hz, 1H), 6.65 (d, J=7.8 Hz, 1H), 4.19 (s, 2H).

b) tert-Butyl 4-(2-(6-bromopyridin-2-yl)hydrazono)piperidine-1-carboxylate

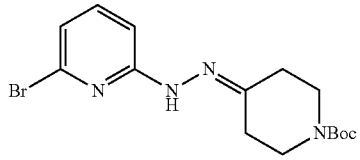

Chemical Formula: $C_{15}H_{21}BrN_4O_2$
Exact Mass: 368.08
Molecular Weight: 369.26

N-Boc piperidinone (13.8 g, 69.1 mmol) was added to a solution of 2-bromo-6-hydrazinylpyridine (13.0 g, 69.1 mmol) in MeOH (240 mL). The resulting solution was stirred at ambient temperature for 2 h. The solution was concentrated and dried to provide the title compound (25.4 g, 99%) as a white foam: $^1$H NMR (300 MHz, DMSO-$d_6$) δ 9.97 (s, 1H), 7.49 (overlapping dd, J=7.8 Hz, 1H), 7.03 (d, J=8.4 Hz, 1H), 6.88 (d, J=7.5 Hz, 1H), 3.52-3.38 (m, 4H), 2.59-2.40 (m, 2H overlaps with solvent), 2.38 (t, J=5.7 Hz, 2H), 1.41 (s, 9H); ESI MS m/z 369 [M+H]+.

c) tert-Butyl 4-(2-(6-bromopyridin-2-yl)-2-methylhydrazono)piperidine-1-carboxylate

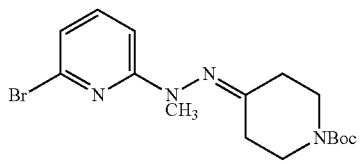

Chemical Formula: $C_{16}H_{23}BrN_4O_2$
Exact Mass: 382.10
Molecular Weight: 383.28

Sodium hydride (60% dispersion in oil, 0.72 g, 18 mmol) was added to a solution of tert-butyl 4-(2-(6-bromopyridin-2-yl)hydrazono)piperidine-1-carboxylate (5.5 g, 15 mmol) in DMF (50 mL) at room temperature under $N_2$, and the resulting solution was stirred for 20 min. Methyl iodide (1.0 mL, 17 mmol) was added to the solution, and the resulting solution was stirred for 2 h at ambient temperature. The mixture was quenched with $H_2O$ (100 mL) and extracted with EtOAc (4×50 mL). The combined organic extracts were concentrated to an orange oil under reduced pressure. The oil was diluted with EtOAc (100 mL) and washed with brine (7×50 mL). The organics were dried over $Na_2SO_4$, filtered, and concentrated to dryness under reduced pressure to provide the title compound (5.7 g, 99%) as an orange oil: $^1$H NMR (300 MHz, DMSO-$d_6$) δ 7.45 (dd, J=8.1, 7.5 Hz, 1H), 6.91 (d, J=7.5 Hz, 1H), 6.67 (d, J=8.4 Hz, 1H), 3.56 (t, J=6.0 Hz, 2H), 3.44 (t, J=6.0 Hz, 2H), 3.09 (s, 3H), 2.53-2.46 (m, 4H, overlap with solvent), 1.42 (s, 9H).

d) tert-Butyl 2-bromo-9-methyl-5,7,8,9-tetrahydro-6H-pyrido[3',4':4,5]pyrrolo[2,3-b]pyridine-6-carboxylate

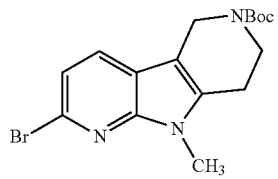

Chemical Formula: $C_{16}H_{20}BrN_3O_2$
Exact Mass: 365.07
Molecular Weight: 366.25 tert-Butyl 4-(2-(6-bromopyridin-2yl-)-2methylhydrazono)piperidine-1-carboxylate (26.3 g, 68.8 mmol) and p-toluene sulfonic acid (27.4 g, 144 mmol) were heated to 160° C. in an oil bath over 45 min. The resulting solution was held at 160° C. for 45 min and cooled to ambient temperature. The resulting oil was diluted with 6:5 $H_2O$/iPrOH (252 mL). $K_2CO_3$ (41.8 g, 302 mmol) was added followed by $Boc_2O$ (116 g, 75.7 mmol), and the resulting solution was stirred at ambient temperature for 2 h. The reaction mixture was diluted with $H_2O$ (100 mL) and extracted with EtOAc (4×50 mL). The combined organic extracts were dried over $Na_2SO_4$, filtered, and concentrated under reduced pressure. The obtained residue was stirred in MeOH (250 mL) for 1.5 h, and the resulting solids were collected by filtration to provide the title compound (2.3 g, 9.2%) as an off-white solid. Additional material was obtained by concentrating the remaining filtrate and diluting with MeOH (50 mL). The resulting solids were collected by filtration to provide the title compound (2.1 g, 8.4%). The remaining filtrate was loaded onto silica gel and passed through a silica gel plug (80:20 hexane/EtOAc, 1 L). The resulting filtrate was concentrated and triturated with hexanes (100 mL). The resulting solids were collected by filtration to provide additional title compound (1.5 g, 5.9%) as a light orange powder: $^1$H NMR (500 MHz, DMSO-$d_6$) δ 7.86 (d, J=8.0 Hz, 1H), 7.20 (d, J=8.5 Hz, 1H), 4.53 (s, 2H), 3.73 (t, J=5.5 Hz, 2H), 3.64 (s, 3H), 2.91-2.79 (m, 2H), 1.43 (s, 9H).

e) tert-Butyl 2-(4-(benzyloxy)-2-oxopyridin-1(2H)-yl)-9-methyl-5,7,8,9-tetrahydro-6H-pyrido[3',4':4,5]pyrrolo[2,3-b]pyridine-6-carboxylate

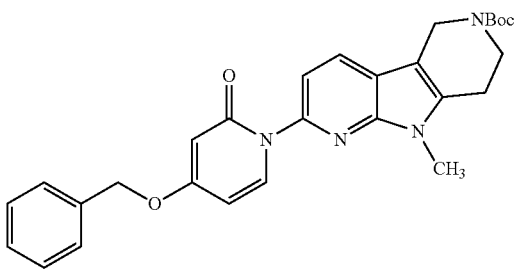

Chemical Formula: $C_{28}H_{30}N_4O_4$
Exact Mass: 486.23
Molecular Weight: 486.56 tert-Butyl 2-bromo-9-methyl-5,7,8,9-tetrahydro-6H-pyrido[3',4':4,5]pyrrolo[2,3-b]pyridine-6-carboxylate (0.73 g, 2.0 mmol), 4-benzyloxy pyridinone (0.44 g, 2.2 mmol), and Cs$_2$CO$_3$ (0.72 g, 2.2 mmol) were suspended in DMSO (12 mL), and the air was removed under vacuum for 15 min. The system was flushed with Ar, and 8-hydroxyquinoline (87 mg, 0.60 mmol) and copper iodide (0.49 g, 2.6 mmol) were added to the suspension. The evacuation/Ar flushing process was repeated twice more, and the reaction mixture was heated at 130° C. for 18 h under N$_2$. The mixture was cooled, diluted with 5.0:3.5:1.5 NH$_4$Cl(aq.)/NH$_4$OH/H$_2$O (70 mL), and the resulting suspension was stirred at ambient temperature for 30 min. The resulting solids were collected by filtration, dissolved in CH$_2$Cl$_2$ (30 mL) and washed with 5.0:3.5:1.5 NH$_4$Cl(aq.)/NH$_4$OH/H$_2$O (2×30 mL). The resulting organic solution was dried over Na$_2$SO$_4$, filtered, and concentrated to dryness under reduced pressure. Flash chromatography (40 g ISCO column, (1:1 hexanes/EtOAc)/(80:18:2 CH$_2$Cl$_2$/MeOH/NH$_4$OH), 100:0 for 2 column volumes, increased to 50:50 over 12 column volumes and held for 5 column volumes; increased to 0:100 over 10 column volumes and held for 5 column volumes) gave the title compound (0.51 g, 52%) as a yellow foam: $^1$H NMR (500 MHz, DMSO-d$_6$) δ 8.00 (d, J=8.0 Hz, 1H), 7.80 (d, J=8.0 Hz, 1H), 7.50-7.36 (m, 5H), 7.29 (d, J=8.0 Hz, 1H), 6.15 (dd, J=8.0, 2.5 Hz, 1H), 5.98 (d, J=2.5 Hz, 1H), 5.16 (s, 2H), 4.57 (s, 2H), 3.75 (t, J=5.5 Hz, 2H) 3.67 (s, 3H), 2.88 (t, J=5.5 Hz, 2H), 1.42 (s, 9H); ESI MS m/z 487 [M+H]$^+$.

f) 4-(Benzyloxy)-1-(9-methyl-5,7,8,9-tetrahydro-6H-pyrido[3',4':4,5]pyrrolo[2,3-b]pyridin-2-yl)pyridin-2(1H)-one

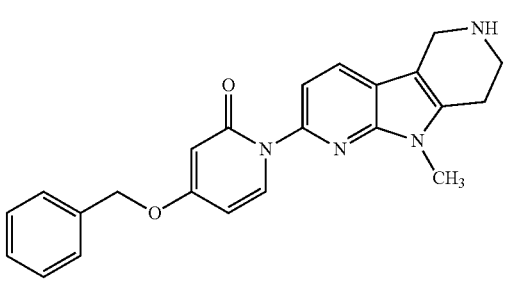

Chemical Formula: C$_{23}$H$_{22}$N$_4$O$_2$
Exact Mass: 386.17
Molecular Weight: 386.45 tert-Butyl 2-(4-(benzyloxy)-2-oxopyridin-1(2H)-yl)-9-methyl-5,7,8,9-tetrahydro-6H-pyrido[3',4':4,5]pyrrolo[2,3-b]pyridine-6-carboxylate (0.51 g, 1.1 mmol) was treated with 1.25 M HCl in MeOH (25 mL), and the resulting solution was stirred at ambient temperature for 18 h. The solution was concentrated to dryness under reduced pressure. The resulting residue was diluted with CH$_2$Cl$_2$ (30 mL) and washed with saturated NaHCO$_3$ solution (50 mL). The resulting layers were separated, and the aqueous phase was extracted with CH$_2$Cl$_2$ (3×30 mL). The combined organic extractions were dried over Na$_2$SO$_4$ and concentrated under reduced pressure to dryness. Flash chromatography (40 g ISCO column, CH$_2$Cl$_2$/(80:18:2 CH$_2$Cl$_2$/MeOH/NH$_4$OH), 100:0 for 4 column volumes, increased to 0:100 over 4 column volumes and held for 10 column volumes) provided the title compound (0.24 g, 59%) as an off-white film: $^1$H NMR (300 MHz, DMSO-d$_6$) δ 7.87 (d, J=8.1 Hz, 1H), 7.79 (d, J=7.8 Hz, 1H), 7.49-7.37 (m, 5H), 7.23 (d, J=8.1 Hz, 1H), 6.15 (dd, J=7.5, 2.7 Hz, 1H), 5.98 (d, J=2.7 Hz, 1H), 5.16 (s, 2H), 3.87 (s, 2H), 3.65 (s, 3H), 3.07 (t, J=5.1 Hz, 2H), 2.79-2.61 (m, 2H).

g) 4-(Benzyloxy)-1-(9-methyl-5,7,8,9-tetrahydro-6H-pyrido[3',4':4,5]pyrrolo[2,3-b]pyridin-2-yl)pyridin-2(1H)-one hydrochloride

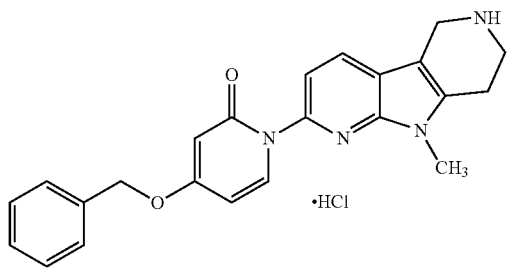

Chemical Formula: C$_{23}$H$_{23}$ClN$_4$O$_2$
Exact Mass: 422.15
Molecular Weight: 422.91

A solution of 4-(benzyloxy)-1-(9-methyl-5,7,8,9-tetrahydro-6H-pyrido[3',4':4,5]pyrrolo[2,3-b]pyridin-2-yl)pyridin-2(1H)-one (0.24 g, 0.62 mmol) in MeOH (2.0 mL) was treated with 1.25 M HCl in MeOH (0.67 mL, 0.84 mmol), and the resulting solution was stirred at ambient temperature for 3 h. The solution was concentrated to dryness, diluted with H$_2$O and lyophilized to yield the title compound (0.16 g, 60%) as an off-white powder: $^1$H NMR (500 MHz, DMSO-d$_6$) δ 8.53 (br s, 1H), 8.02 (d, J=8.0 Hz, 1H), 7.81 (d, J=7.5 Hz, 1H), 7.49-7.41 (m, 4H), 7.40-7.32 (m, 2H), 6.17 (dd, J=7.5, 2.5 Hz, 1H), 5.99 (d, J=2.5 Hz, 1H), 5.17 (s, 2H), 4.27 (s, 2H), 3.70 (s, 3H), 3.46 (t, J=5.5 Hz, 2H), 3.05 (t, J=5.5 Hz, 2H); ESI MS m/z 387 [M+H]$^+$; HPLC (Method A)>99% (AUC), t$_R$=13.5 min.

Example 3

Preparation of 1-(9-Methyl-5,7,8,9-tetrahydro-6H-pyrido[3',4':4,5]pyrrolo[2,3-b]pyridin-2-yl)-4-phenethylpiperazin-2-one dihydrochloride a) 4-Phenethylpiperazin-2-one (CAS Registry Number 23099-72-1) (JP 43017188 to Irikura et al., which is Hereby Incorporated by Reference in its Entirety)

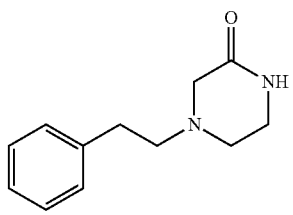

Chemical Formula: C$_{12}$H$_{16}$N$_2$O
Exact Mass: 204.13
Molecular Weight: 204.27

A suspension of (2-bromoethyl)benzene (4.10 mL, 30.0 mmol), piperazin-2-one (3.00 g, 30.0 mmol) and K$_2$CO$_3$ (4.90 g, 36.0 mmol) in DMSO (60.0 mL) was stirred at 80° C. for 5 h. The reaction mixture was cooled to room temperature and filtered. The filtrate was then washed with water (200 mL) and extracted with methylene chloride (2×). The combined organic layers were washed with brine, dried over MgSO$_4$, filtered, and concentrated. The result yellow solid was then dissolved in 1 N HCl (120 mL) and washed with methylene chloride. The aqueous layer was separated, basified with 6 N NaOH, and extracted with methylene chloride (3×). The combined organic layers were dried over MgSO$_4$, filtered, and concentrated. The residue was titrated with hexanes and filtered. The filtered solid was dried under reduced pressure to give the title compound (4.50 g, 74%) as an off-white solid: $^1$H NMR (500 MHz, CDCl$_3$) δ 7.31-7.28 (m, 2H), 7.23-7.19 (m, 3H), 6.17 (br s, 1H), 3.40-3.37 (m, 2H), 3.23 (s, 2H), 2.83-2.79 (m, 2H), 2.73-2.67 (m, 4H).

b) tert-Butyl 9-methyl-2-(2-oxo-4-phenethylpiperazin-1-yl)-5,7,8,9-tetrahydro-6H-pyrido[3',4':4,5]pyrrolo[2,3-b]pyridine-6-carboxylate

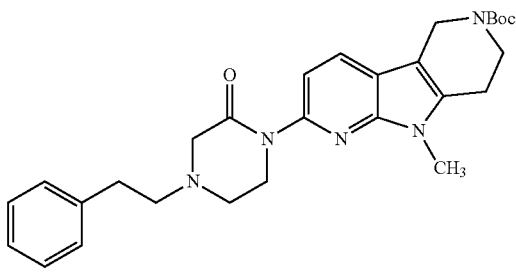

Chemical Formula: C$_{28}$H$_{35}$N$_5$O$_3$
Exact Mass: 489.27
Molecular Weight: 489.61 tert-Butyl 2-bromo-9-methyl-5,7,8,9-tetrahydro-6H-pyrido[3',4':4,5]pyrrolo[2,3-b]pyridine-6-carboxylate (86 mg, 0.23 mmol) and 4-phenethylpiperazin-2-one (56 mg, 0.27 mmol) were reacted according to Example 2 (step e) to provide the title compound (76 mg, 67%) as a yellow powder: ESI MS m/z 490 [M+H]$^+$.

c) 1-(9-Methyl-5,7,8,9-tetrahydro-6H-pyrido[3',4':4,5]pyrrolo[2,3-b]pyridin-2-yl)-4-phenethylpiperazin-2-one dihydrochloride

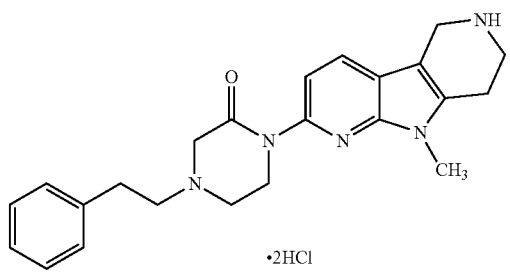

Chemical Formula: C$_{23}$H$_{29}$Cl$_2$N$_5$O
Exact Mass: 461.17
Molecular Weight: 462.42 tert-Butyl 9-methyl-2-(2-oxo-4-phenethylpiperazin-1-yl)-5,7,8,9-tetrahydro-6H-pyrido[3',4':4,5]pyrrolo[2,3-b]pyridine-6-carboxylate (76 mg, 0.15 mmol) was deprotected and converted to the hydrochloride salt according to Example 2 (steps f and g) to provide the title compound (14 mg, 20%) as an off-white solid; $^1$H NMR (500 MHz, DMSO-d$_6$) δ 9.47 (br s, 2H), 8.01 (d, J=8.4 Hz, 1H), 7.53 (d, J=8.4 Hz, 1H), 7.40-7.25 (m, 5H), 4.38-4.24 (m, 3H), 4.24-4.07 (m, 2H), 4.06-3.89 (m, 2H), 3.70 (s, 3H), 3.60-3.38 (m, 6H), 3.19-3.07 (m, 4H); ESI MS m/z 390 [M+H]$^+$; HPLC (Method B) 96.9% (AUC), t$_R$=11.6 min.

Example 4

Preparation of 4-((5-Fluoropyridin-2-yl)methoxy)-1-(9-methyl-5,7,8,9-tetrahydro-6H-pyrido[3',4':4,5]pyrrolo[2,3-b]pyridin-2-yl)pyridin-2(1H)-one hydrochloride a) 4-((5-Fluoropyridin-2-yl)methoxy)pyridine 1-oxide (CAS Registry Number 1173155-63-9) (WO 2009/089482 to Guzzo et al., which is Hereby Incorporated by Reference in its Entirety)

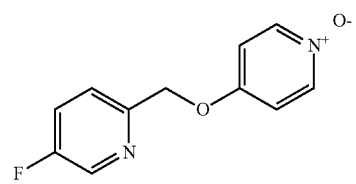

Chemical Formula: C$_{11}$H$_9$FN$_2$O$_2$
Exact Mass: 220.06
Molecular Weight: 220.20

5-Fluoro-2-pyridylbenzylalcohol (3.00 g, 23.6 mmol) was dissolved in DMF (20 mL), and NaH (60% weight dispersion in mineral oil, 0.92 g, 23 mmol) was added. After stirring for 30 minutes, 4-chloropyridine-N-oxide (2.03 g, 15.7 mmol) was added, and the reaction mixture was heated for 1 h at 120° C. Upon cooling, the mixture was diluted with methylene chloride, washed with 5% lithium chloride solution (5×), dried, and concentrated. Purification by flash column chromatography (40 g ISCO column eluting with methylene chloride and a methanol/ammonia mixture (10:1); gradient 100% methylene chloride to 90% methylene chloride over 30 min at 40 mL/min) provided the title compound (1.76 g, 50%) as a tan solid: $^1$H NMR (300 MHz, CDCl$_3$) δ 8.48 (s, 1H), 8.12 (d, J=7.7 Hz, 2H), 7.48-7.46 (m, 2H), 6.90 (d, J=7.7 Hz, 2H), 5.20 (s, 2H).

b) 4-((5-Fluoropyridin-2-yl)methoxy)pyridin-2(1H)-one (CAS Registry Number 924311-90-0) (WO 2007/018248 to Ando et al., which is Hereby Incorporated by Reference in its Entirety)

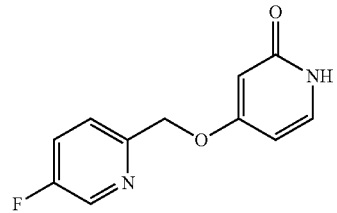

Chemical Formula: C$_{11}$H$_9$FN$_2$O$_2$
Exact Mass: 220.06
Molecular Weight: 220.20

4-((5-Fluoropyridin-2-yl)methoxy)pyridine 1-oxide (1.76 g, 7.99 mmol) was heated to 140° C. in acetic anhydride (80 mL) for 5 h. The mixture was concentrated and then heated at 80° C. for 1 h in a mixture of MeOH (20 mL) and aqueous 1 N NaOH (15 mL). The resulting black solution was concentrated to a volume of 15 mL, and the solid was filtered off, rinsed with CH$_2$Cl$_2$ and dried under vacuum to provide the title compound (1.29 g, 73%) as a yellow solid: $^1$H NMR (500 MHz, DMSO-d$_6$) δ 11.12 (s, 1H), 8.59 (d, J=2.9 Hz, 1H), 7.79 (ddd, J=8.7, 8.7, 2.9 Hz, 1H), 7.60 (dd, J=8.7, 4.5 Hz, 1H), 7.26 (d, J=7.3 Hz, 1H), 5.95 (dd, J=7.4, 2.6 Hz, 1H), 5.78 (d, J=2.5 Hz, 1H), 5.12 (s, 2H).

c) tert-Butyl 2-(4-((5-fluoropyridin-2-yl)methoxy)-2-oxopyridin-1(2H)-yl)-9-methyl-5,7,8,9-tetrahydro-6H-pyrido[3',4':4,5]pyrrolo[2,3-h]pyridine-6-carboxylate

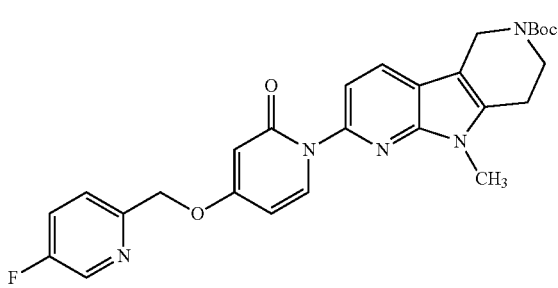

Chemical Formula: C$_{27}$H$_{28}$FN$_5$O$_4$
Exact Mass: 505.21
Molecular Weight: 505.54 tert-Butyl 2-bromo-9-methyl-5,7,8,9-tetrahydro-6H-pyrido[3',4':4,5]pyrrolo[2,3-b]pyridine-6-carboxylate (0.20 g, 0.55 mmol), 4-((5-fluoropyridin-2-yl)methoxy)pyridin-2 (1H)-one (0.13 g, 0.61 mmol), and Cs$_2$CO$_3$ (0.20 g, 0.61 mmol) were suspended in DMSO (3.2 mL), and the air was removed under vacuum for 15 min. The system was flushed with Ar, and 8-hydroxyquinoline (24 mg, 0.17 mmol) and copper iodide (0.14 g, 0.72 mmol) were added to the suspension. The evacuation/Ar flushing process was repeated twice more, and the reaction mixture was heated at 130° C. for 18 h under N$_2$. The mixture was cooled, diluted with 5.0:3.5:1.5 NH$_4$Cl(aq.)/NH$_4$OH/H$_2$O (70 mL), and the resulting suspension was stirred at ambient temperature for 30 min. The resulting solids were collected by filtration, dissolved in CH$_2$Cl$_2$ (30 mL) and washed with 5.0:3.5:1.5 NH$_4$Cl(aq.)/NH$_4$OH/H$_2$O (2×20 mL). The resulting organic solution was dried over Na$_2$SO$_4$, filtered, and concentrated to dryness under reduced pressure. Flash chromatography (12 g ISCO column, (1:1 hexanes/EtOAc)/(80:18:2 CH$_2$Cl$_2$/MeOH/NH$_4$OH), 100:0 for 4 column volumes, increased to 50:50 over 20 column volumes and held for 5 column volumes; increased to 0:100 over 10 column volumes) gave the title compound (0.14 g, 50%) as an off-white solid: $^1$H NMR (500 MHz, DMSO-d$_6$) δ 8.62 (d, J=3.0 Hz, 1H), 8.00 (d, J=8.0 Hz, 1H), 7.88-7.78 (m, 2H), 7.68-7.64 (m, 1H), 7.28 (d, J=8.0 Hz, 1H), 6.18 (dd, J=7.5, 2.5 Hz, 1H), 5.99 (d, J=3.0 Hz, 1H), 5.23 (s, 2H), 4.57 (s, 2H), 3.75 (t, J=5.5 Hz, 2H), 3.67 (s, 3H), 2.93-2.85 (m, 2H), 1.44 (s, 9H); ESI MS m/z 506 [M+H]$^+$.

d) 4-((5-Fluoropyridin-2-yl)methoxy)-1-(9-methyl-5,7,8,9-tetrahydro-6H-pyrido[3',4':4,5]pyrrolo[2,3-b]pyridin-2-yl)pyridin-2 (1H)-one

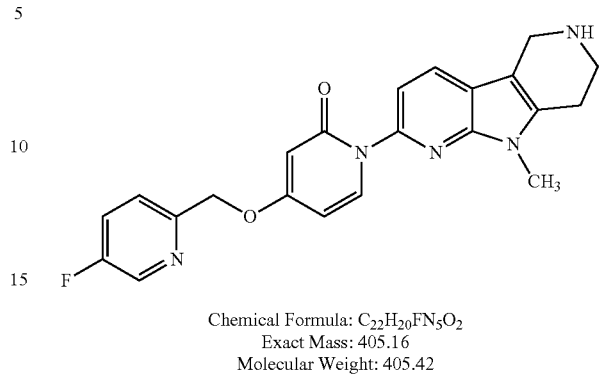

Chemical Formula: C$_{22}$H$_{20}$FN$_5$O$_2$
Exact Mass: 405.16
Molecular Weight: 405.42 tert-Butyl 2-(4-((5-fluoropyridin-2-yl)methoxy)-2-oxopyridin-1(2H)-yl)-9-methyl-5,7,8,9-tetrahydro-6H-pyrido[3',4':4,5]pyrrolo[2,3-b]pyridine-6-carboxylate (0.14 g, 0.28 mmol) was treated with 1.25 M HCl in MeOH (7.0 mL), and the resulting suspension was stirred at ambient temperature for 18 h. The resulting solids were collected by filtration, dissolved in CH$_2$Cl$_2$ (30 mL), and washed with saturated NaHCO$_3$ solution (50 mL). The resulting layers were separated, and the organic layer was dried over Na$_2$SO$_4$ and concentrated under reduced pressure to dryness. Flash chromatography (12 g ISCO column, CH$_2$Cl$_2$/(80:18:2 CH$_2$Cl$_2$/MeOH/NH$_4$OH), 100:0 for 4 column volumes, increased to 0:100 over 20 column volumes and held for 34 column volumes) provided the title compound (75 mg, 67%) as an off-white solid: $^1$H NMR (300 MHz, DMSO-d$_6$) δ 8.62 (d, J=2.7 Hz, 1H), 7.92-7.78 (m, 3H), 7.69-7.62 (m, 1H), 7.23 (d, J=8.1 Hz, 1H), 6.18 (dd, J=7.8, 2.7 Hz, 1H), 5.98 (d, J=2.7 Hz, 1H), 5.23 (s, 2H), 3.87 (s, 2H), 3.65 (s, 3H), 3.08 (t, J=5.7 Hz, 2H), 2.75 (t, J=5.4 Hz, 2H).

e) 4-((5-Fluoropyridin-2-yl)methoxy)-1-(9-methyl-5,7,8,9-tetrahydro-6H-pyrido[3',4':4,5]pyrrolo[2,3-b]pyridin-2-yl)pyridin-2 (1H)-one hydrochloride

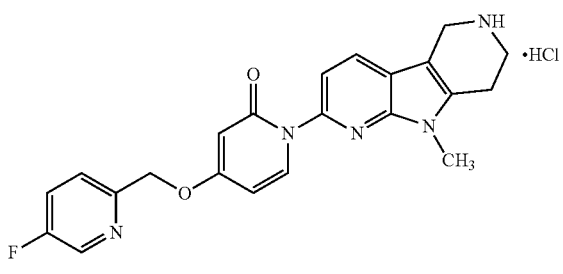

Chemical Formula: C$_{22}$H$_{21}$ClFN$_5$O$_2$
Exact Mass: 441.14
Molecular Weight: 441.89

A solution of 4-((5-fluoropyridin-2-yl)methoxy)-1-(9-methyl-5,7,8,9-tetrahydro-6H-pyrido[3',4':4,5]pyrrolo[2,3-b]pyridin-2-yl)pyridin-2(1H)-one (75 mg, 0.18 mmol) in MeOH (2.0 mL) was treated with 1.25 M HCl in MeOH (0.15 mL, 0.18 mmol), and the resulting solution was stirred at ambient temperature for 2 h. The resulting solids were collected by filtration to provide the title compound (63 mg, 77%) as an off-white powder: 250-256° C. decomp.; $^1$H NMR (500 MHz, DMSO-d$_6$) δ 8.62 (d, J=3.0 Hz, 1H), 7.97 (s, J=8.0 Hz, 1H), 7.87-7.78 (m, 2H), 7.69-7.64 (m, 1H), 7.30 (s, J=8.0 Hz, 1H), 7.09 (br s, 1H), 6.19 (dd, J=7.5, 2.5 Hz, 1H), 5.99 (d, J=3.0 Hz, 1H), 5.23 (s, 2H), 4.12 (s, 2H), 3.68 (s, 3H), 3.36-3.21 (m, 2H, overlap with H₂O), 2.94 (t, J=5.5 Hz, 2H); ESI MS m/z 406 [M+H]⁺; HPLC (Method A)>99% (AUC), t_R=11.4 min.

Example 5

Preparation of 1-(9-Methyl-5,7,8,9-tetrahydro-6H-pyrido[3',4':4,5]pyrrolo[2,3-b]pyridin-2-yl)-4-(6-(trifluoromethyl)pyridazin-3-yl)pyridin-2(1H)-one hydrochloride a) 3-(2-Methoxypyridin-4-yl)-6-(trifluoromethyl)pyridazine (CAS Registry Number 1173155-65-1) (WO 2009/089482 to Guzzo et al., which is Hereby Incorporated by Reference in its Entirety)

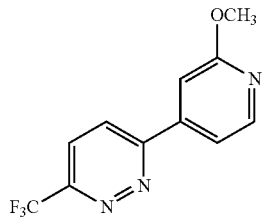

Chemical Formula: C₁₁H₈F₃N₃O
Exact Mass: 255.06
Molecular Weight: 255.20

3-Chloro-6-(trifluoromethyl)pyridazine (137 mg, 0.751 mmol), 2-methoxy-4-(4,4,5,5-tetramethyl-1,3,2-dioxaborolan-2-yl)pyridine (176 mg, 0.749 mmol), K₂CO₃ (310 mg, 2.25 mmol) and PdCl₂(dppf) (61 mg, 0.075 mmol) were stirred in DMSO (4 mL). The reaction mixture was degassed, then back-filled with N₂. The reaction mixture was stirred at 80° C. in a pre-heated oil bath for 2 hours. After cooling, the reaction was quenched with water and extracted with CH₂Cl₂. The organic layer was washed with H₂O and 5% LiCl solution, dried with Na₂SO₄, filtered and concentrated. Flash chromatography (silica gel, hexanes/EtOAc), 100:0 to 50:50) afforded the title compound (115 mg, 60%) as a white solid: ¹H NMR (500 MHz, CDCl₃) δ 8.39 (d, J=5.8 Hz, 1H), 8.05 (d, J=8.8 Hz, 1H), 7.94 (d, J=8.8 Hz, 1H), 7.62 (dd, J=5.4, 1.5 Hz, 1H), 7.45 (s, 1H), 4.03 (s, 3H).

b) 4-(6-(Trifluoromethyl)pyridazin-3-yl)pyridin-2 (1H)-one (CAS Registry Number 1173155-66-2 (WO 2009/089482 to Guzzo et al., which is Hereby Incorporated by Reference in its Entirety)

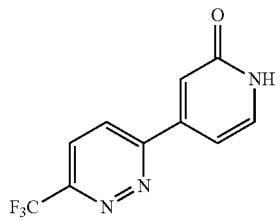

Chemical Formula: C₁₀H₆F₃N₃O
Exact Mass: 241.05
Molecular Weight: 241.17

3-(2-Methoxypyridin-4-yl)-6-(trifluoromethyl)pyridazine (115 mg, 0.451 mmol) was stirred in concentrated hydrochloric acid (20 mL) at 120° C. for 18 h and then concentrated. The residue was adjusted to pH 8 with 6 N NaOH solution, and the solids were filtered off, washed with water and dried under vacuum to provide the title compound (120 mg, quant) as a white solid: ¹H NMR (500 MHz, DMSO-d₆) δ 11.87 (s, 1H), 8.61 (d, J=8.9 Hz, 1H), 8.42 (d, J=8.9 Hz, 1H), 7.62 (d, J=6.8 Hz, 1H), 7.19 (s, 1H), 7.01 (dd, J=6.8, 1.6 Hz, 1H).

c) tert-Butyl 9-methyl-2-(2-oxo-4-(6-(trifluoromethyl)pyridazin-3-yl)pyridin-1(2H)-yl)-5,7,8,9-tetrahydro-6H-pyrido[3',4':4,5]pyrrolo[2,3-b]pyridine-6-carboxylate

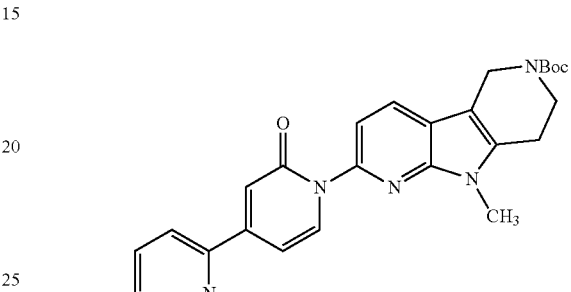

Chemical Formula: C₂₆H₂₅F₃N₆O₃
Exact Mass: 526.19
Molecular Weight: 526.51 tert-Butyl 2-bromo-9-methyl-5,7,8,9-tetrahydro-6H-pyrido[3',4':4,5]pyrrolo[2,3-b]pyridine-6-carboxylate (0.11 g, 0.30 mmol), 4-(6-(trifluoromethyl)pyridazin-3-yl)pyridin-2(1H)-one (73 mg, 0.30 mmol), and Cs₂CO₃ (0.11 g, 0.33 mmol) were suspended in DMSO (2.0 mL), and the air was removed under vacuum for 15 min. The system was flushed with Ar, and 8-hydroxyquinoline (13 mg, 0.091 mmol) and copper iodide (75 mg, 0.39 mmol) were added to the suspension. The evacuation/Ar flushing process was repeated twice more, and the reaction mixture was heated at 130° C. for 18 h under N₂. The mixture was cooled, diluted with 5.0:3.5:1.5 NH₄Cl(aq.)/NH₄OH/H₂O (70 mL), and the resulting suspension was stirred at ambient temperature for 30 min. The resulting solids were collected by filtration, dissolved in CH₂Cl₂ (30 mL), and washed with 5.0:3.5:1.5 NH₄Cl(aq.)/NH₄OH/H₂O (2×30 mL). Activated charcoal was added to the organic solution, and the resulting suspension was filtered through a Celite® plug and concentrated to dryness under reduced pressure. Flash chromatography (12 g ISCO column, (1:1 hexanes/EtOAc)/(80:18:2 CH₂Cl₂/MeOH/NH₄OH), 100:0 for 4 column volumes, increased to 50:50 over 20 column volumes and held for 4 column volumes; increased to 0:100 over 10 column volumes and held for 4 column volumes) gave the title compound (70 mg, 43%) as a yellow powder: ¹H NMR (500 MHz, DMSO-d₆) δ 8.71 (d, J=9.0 Hz, 1H), 8.46 (d, J=9.0 Hz, 1H), 8.13 (d, J=7.5 Hz, 1H), 8.08 (d, J=8.0 Hz, 1H), 7.43 (d, J=8.0 Hz, 1H), 7.41 (d, J=1.5 Hz, 1H), 7.22 (dd, J=7.5, 1.5 Hz, 1H), 4.60 (s, 2H), 3.77 (t, J=5.5 Hz, 2H), 3.71 (s, 3H), 2.90 (t, J=5.5 Hz, 2H), 1.45 (s, 9H); ESI MS m/z 527 [M+H]⁺.

d) 1-(9-Methyl-5,7,8,9-tetrahydro-6H-pyrido[3',4':4,5]pyrrolo[2,3-b]pyridin-2-yl)-4-(6-(trifluoromethyl)pyridazin-3-yl)pyridin-2(1H)-one

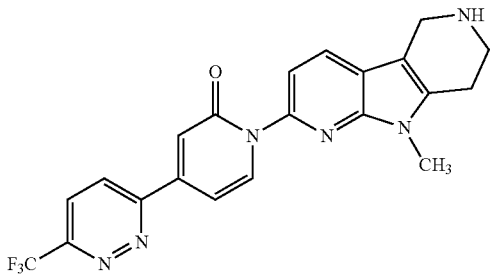

Chemical Formula: C₂₁H₁₇F₃N₆O
Exact Mass: 426.14
Molecular Weight: 426.39 tert-Butyl 9-methyl-2-(2-oxo-4-(6-(trifluoromethyl)pyridazin-3-yl)pyridin-1(2H)-yl)-5,7,8,9-tetrahydro-6H-pyrido[3',4':4,5]pyrrolo[2,3-b]pyridine-6-carboxylate (70 mg, 0.13 mmol) was treated with 1.25 M HCl in MeOH (3.4 mL), and the resulting suspension was stirred at ambient temperature for 18 h. The resulting suspension was diluted with CH₂Cl₂ (1.8 mL) and stirred at ambient temperature for 4 h. To the suspension 1.25 M HCl in MeOH (2.0 mL) was added, and the resulting suspension was stirred at ambient temperature for 18 h. The resulting solids were collected by filtration, dissolved in CH₂Cl₂ (30 mL), and washed with saturated NaHCO₃ solution (50 mL). The resulting layers were separated, and the organic extraction was dried over Na₂SO₄ and concentrated under reduced pressure to dryness. Flash chromatography (12 g ISCO column, CH₂Cl₂/(80:18:2 CH₂Cl₂/MeOH/NH₄OH), 100:0 for 1 column volumes, increased to 0:100 over 20 column volumes and held for 83 column volumes) provided the title compound (38 mg, 67%) as a yellow powder: ¹H NMR (500 MHz, DMSO-d₆) δ 8.71 (d, J=8.5 Hz, 1H), 8.46 (d, J=9.0 Hz, 1H), 8.13 (d, J=7.0 Hz, 1H), 7.96 (d, J=8.5 Hz, 1H), 7.40 (d, J=2.0 Hz, 1H), 7.38 (d, J=8.0 Hz, 1H), 7.22 (dd, J=7.5, 2.0 Hz, 1H), 3.91 (s, 2H), 3.69 (s, 3H), 3.11 (t, J=5.5 Hz, 2H), 2.78 (t, J=5.5 Hz, 2H); ESI MS m/z 427 [M+H]⁺.

e) 1-(9-Methyl-5,7,8,9-tetrahydro-6H-pyrido[3',4':4,5]pyrrolo[2,3-b]pyridin-2-yl)-4-(6-(trifluoromethyl)pyridazin-3-yl)pyridin-2(1H)-one hydrochloride

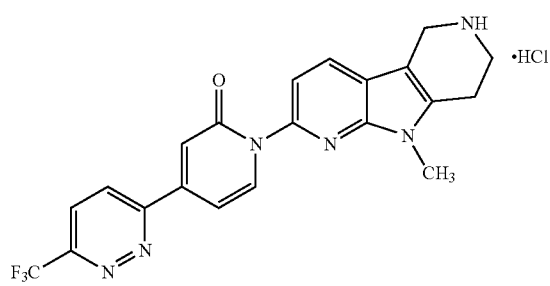

Chemical Formula: C₂₁H₁₈ClF₃N₆O
Exact Mass: 462.12
Molecular Weight: 462.86

A solution of 1-(9-methyl-5,7,8,9-tetrahydro-6H-pyrido[3',4':4,5]pyrrolo[2,3-b]pyridin-2-yl)-4-(6-(trifluoromethyl)pyridazin-3-yl)pyridin-2(1H)-one (34 mg, 0.081 mmol) in MeOH (2.0 mL) was treated with 1.25 M HCl in MeOH (65 µL, 0.081 mmol), and the resulting solution was stirred at ambient temperature for 3 h. The solution was diluted with Et₂O (20 mL), and the resulting solids were collected by filtration to provide the title compound (20 mg, 55%) as a yellow powder: 288-294° C. decomp.; ¹H NMR (500 MHz, DMSO-d₆) δ 8.72 (d, J=9.0 Hz, 1H), 8.47 (d, J=8.5 Hz, 1H), 8.14 (d, J=7.5 Hz, 1H), 8.06 (d, J=8.5 Hz, 1H), 7.45 (d, J=8.0 Hz, 1H), 7.41 (d, J=2.0 Hz, 1H), 7.23 (dd, J=7.5, 2.0 Hz, 1H), 4.19 (s, 2H), 3.72 (s, 3H), 3.38 (t, J=5.5 Hz, 2H), 3.00 (t, J=5.5 Hz, 2H); ESI MS m/z 427 [M+H]⁺; HPLC (Method A)>99% (AUC), $t_R$=12.5 min.

Example 6

Preparation of 1-(9-Methyl-5,7,8,9-tetrahydro-6H-pyrido[3',4':4,5]pyrrolo[2,3-b]pyridin-2-yl)-4-(6-(trifluoromethyl)pyridin-3-yl)pyridin-2(1H)-one hydrochloride a) 2'-Methoxy-6-(trifluoromethyl)-3,4'-bipyridine (CAS Registry Number 1173155-80-0) (WO 2009/089482 to Guzzo et al., which is Hereby Incorporated by Reference in its Entirety)

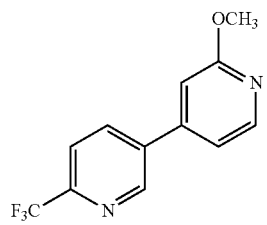

Chemical Formula: C₁₂H₉F₃N₂O
Exact Mass: 254.07
Molecular Weight: 254.21

2-Methoxy-4-(4,4,5,5-tetramethyl-1,3,2-dioxaborolan-2-yl)pyridine (1.24 g, 0.53 mmol) and 5-bromo-2-(trifluoromethyl)pyridine (2.4 g, 11 mmol) were reacted according to the procedure of Example 5 (step a) to provide the title compound (1.1 g, 81%) as a white solid: ESI MS m/z 255 [M+H].

b) 4-(6-(Trifluoromethyl)pyridin-3-yl)pyridin-2(1H)-one (CAS Registry Number 1173155-81-1) (WO 2009/089482 to Guzzo et al., which is Hereby Incorporated by Reference in its Entirety)

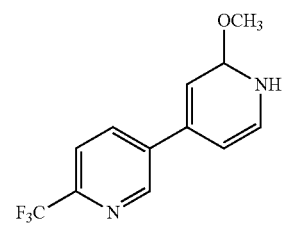

Chemical Formula: C₁₁H₇F₃N₂O
Exact Mass: 240.05
Molecular Weight: 240.18

2'-Methoxy-6-(trifluoromethyl)-3,4'-bipyridine (1.1 g, 4.3 mmol) was reacted according to the procedure of Example 5 (step b) to provide the title compound (522 mg, 50%) as a white solid: ¹H NMR (500 MHz, DMSO-d₆) δ 11.80 (br s, 1H), 9.10 (s, 1H), 8.40 (dd, J=8.1, 1.2 Hz, 1H), 8.00 (d, J=8.2 Hz, 1H), 7.56 (d, J=6.7 Hz, 1H), 6.81 (s, 1H), 6.63 (dd, J=6.7, 1.3 Hz, 1H).

c) tert-Butyl 9-methyl-2-(2-oxo-4-(6-(trifluoromethyl)pyridin-3-yl)pyridin-1(2H)-yl)-5,7,8,9-tetrahydro-6H-pyrido[3',4':4,5]pyrrolo[2,3-b]pyridine-6-carboxylate

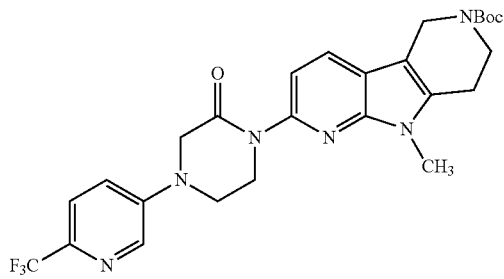

Chemical Formula: C₂₇H₂₆F₃N₅O₃
Exact Mass: 525.20
Molecular Weight: 525.52 tert-Butyl 2-bromo-9-methyl-5,7,8,9-tetrahydro-6H-pyrido[3',4':4,5]pyrrolo[2,3-b]pyridine-6-carboxylate (0.80 g, 2.2 mmol), 4-(6-(trifluoromethyl)pyridin-3-yl)pyridin-2 (1H)-one (0.58 g, 2.4 mmol), and Cs₂CO₃ (0.78 g, 2.4 mmol) were suspended in DMSO (13 mL), and the air was removed under vacuum for 15 min. The system was flushed with Ar, and 8-hydroxyquinoline (95 mg, 0.65 mmol) and copper iodide (0.54 g, 2.8 mmol) were added to the suspension. The evacuation/Ar flushing process was repeated twice more, and the reaction mixture was heated at 130° C. for 18 h under N₂. The mixture was cooled, diluted with 5.0:3.5:1.5 NH₄Cl(aq.)/NH₄OH/H₂O (70 mL), and the resulting suspension was stirred at ambient temperature for 30 min. The resulting solids were collected by filtration, dissolved in CH₂Cl₂ (30 mL) and washed with 5.0:3.5:1.5 NH₄Cl(aq.)/NH₄OH/H₂O (2×30 mL). Activated charcoal was added to the organic solution, and the resulting suspension was filtered through a Celite® plug and concentrated to dryness under reduced pressure. Flash chromatography (40 g ISCO column, (1:1 hexanes/EtOAc)/(80:18:2 CH₂Cl₂/MeOH/NH₄OH), 100:0 for 4 column volumes, increased to 50:50 over 12 column volumes and held for 4 column volumes; increased to 0:100 over 10 column volumes and held for 4 column volumes) gave the title compound (0.82 g, 71%) as a yellow solid: ¹H NMR (500 MHz, DMSO-d₆) δ 9.20 (d, J=1.5 Hz, 1H), 8.50 (dd, J=8.5, 2.0 Hz, 1H), 8.08-8.05 (m, 3H), 7.39 (d, J=8.5 Hz, 1H), 7.03 (d, J=1.5 Hz, 1H), 6.84 (dd, J=7.0, 2.0 Hz, 1H), 4.59 (s, 2H), 3.77 (t, J=5.5 Hz, 2H), 3.70 (s, 3H), 2.90 (t, J=5.5 Hz, 2H), 1.45 (s, 9H).

d) 1-(9-Methyl-5,7,8,9-tetrahydro-6H-pyrido[3',4':4,5]pyrrolo[2,3-b]pyridin-2-yl)-4-(6-(trifluoromethyl)pyridin-3-yl)pyridin-2(1H)-one

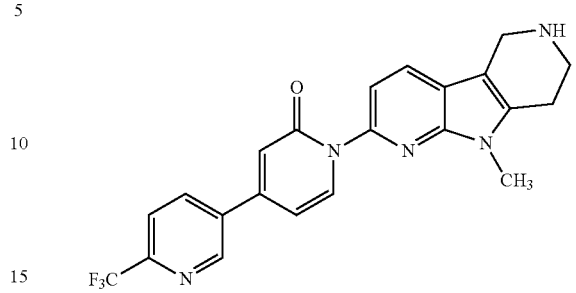

Chemical Formula: C₂₂H₁₈F₃N₅O
Exact Mass: 425.15
Molecular Weight: 425.41

To a solution of tert-butyl 9-methyl-2-(2-oxo-4-(6-(trifluoromethyl)pyridin-3-yl)pyridin-1(2H)-yl)-5,7,8,9-tetrahydro-6H-pyrido[3',4':4,5]pyrrolo[2,3-b]pyridine-6-carboxylate (0.81 g, 1.6 mmol) in CH₂Cl₂ (8.0 mL) was added 1.25 M HCl in MeOH (30 mL), and the resulting suspension was stirred at ambient temperature for 18 h. The suspension was diluted with CH₂Cl₂ (18 mL), 1.25 M HCl in MeOH (6.0 mL) was added, and the resulting suspension was stirred at ambient temperature for 72 h. The suspension was diluted with Et₂O (50 mL), and the resulting solids were collected by filtration, dissolved in CH₂Cl₂ (30 mL), and washed with saturated NaHCO₃ solution (50 mL). The resulting layers were separated, and the organic layer was concentrated under reduced pressure to dryness. Flash chromatography (40 g ISCO column, CH₂Cl₂/(80:18:2 CH₂Cl₂/MeOH/NH₄OH), 100:0 for 1 column volume, increased to 0:100 over 12 column volumes and held for 30 column volumes) provided the title compound (0.50 g, 75%) as a yellow powder: ¹H NMR (500 MHz, DMSO-d₆) δ 9.20 (d, J=2.0 Hz, 1H), 8.50 (dd, J=8.0, 2.0 Hz, 1H), 8.10-8.02 (m, 2H), 7.94 (d, J=8.0 Hz, 1H), 7.35 (d, J=8.5 Hz, 1H), 7.02 (d, J=2.0 Hz, 1H), 6.83 (dd, J=7.5, 20 Hz, 1H), 3.89 (s, 2H), 3.68 (s, 3H), 3.09 (t, J=5.5 Hz, 2H), 2.76 (t, J=5.5 Hz, 2H).

e) 1-(9-Methyl-5,7,8,9-tetrahydro-6H-pyrido[3',4':4,5]pyrrolo[2,3-b]pyridin-2-yl)-4-(6-(trifluoromethyl)pyridin-3-yl)pyridin-2(1H)-one hydrochloride

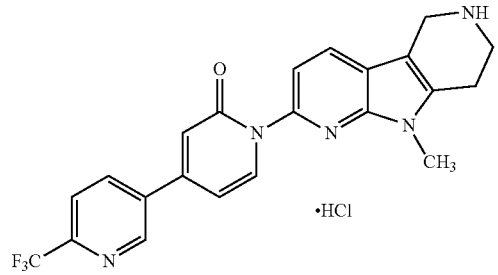

Chemical Formula: C₂₂H₁₉ClF₃N₅O
Exact Mass: 461.12
Molecular Weight: 461.87

A solution of 1-(9-methyl-5,7,8,9-tetrahydro-6H-pyrido[3',4':4,5]pyrrolo[2,3-b]pyridin-2-yl)-4-(6-(trifluoromethyl)

pyridin-3-yl)pyridin-2(1H)-one (0.49 g, 1.2 mmol) in MeOH (4.0 mL) was treated with 1.25 M HCl in MeOH (0.92 mL, 1.2 mmol), and the resulting suspension was stirred at ambient temperature for 4 h. The suspension was diluted with Et$_2$O (50 mL) the resulting solids were collected by filtration, washed with CH$_2$Cl$_2$ (60 mL), and Et$_2$O to provide the title compound (0.30 g, 55%) as a yellow powder: 307-316° C. decomp.; $^1$H NMR (500 MHz, DMSO-d$_6$) δ 9.38 (s, 2H), 9.21 (d, J=2.5 Hz, 1H), 8.51 (dd, J=8.0, 2.0 Hz, 1H), 8.12 (d, J=8.5 Hz, 1H), 8.09-8.04 (m, 2H), 7.46 (d, J=8.0 Hz, 1H), 7.04 (d, J=2.0 Hz, 1H), 6.86 (dd, J=7.5, 2.0 Hz, 1H), 4.37 (s, 2H), 3.74 (s, 3H), 3.55 (t, J=6.5 Hz, 2H), 3.15 (t, J=6.0 Hz, 2H); ESI MS m/z 426 [M+H]$^+$; HPLC (Method A)>99% (AUC), t$_R$=13.1 min.

Example 7

Preparation of 1-(9-Methyl-5,7,8,9-tetrahydro-6H-pyrido[3',4':4,5]pyrrolo[2,3-b]pyridin-2-yl)-4-((6-(trifluoromethyl)pyridin-3-yl)methoxy)pyridin-2(1H)-one hydrochloride a) 2-Methoxy-4-((6-(trifluoromethyl)pyridin-3-yl)methoxy)pyridine

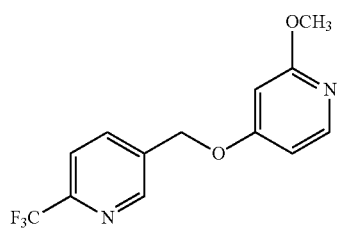

Chemical Formula: C$_{13}$H$_{11}$F$_3$N$_2$O$_2$
Exact Mass: 284.08
Molecular Weight: 284.23

4-Bromo-2-methoxypyridine (3.06 g, 16.2 mmol), (6-(trifluoromethyl)pyridin-3-yl)methanol (2.74 g, 15.5 mmol), 3,4,7,8-tetramethylphenanthroline (0.36 g, 0.15 mmol), CuI (0.14 g, 0.74 mmol) and Cs$_2$CO$_3$ (7.57 g, 23.2 mmol) were combined in toluene (15 mL) and heated to reflux under a nitrogen atmosphere for 16 h. Upon cooling the mixture was purified by flash column chromatography (silica gel, hexanes/EtOAc, 1:0 to 1:1) to provide the title compound (3.19 g, 72%) as a red oil: $^1$H NMR (300 MHz, CDCl$_3$) δ 8.78 (s, 1H), 8.02 (d, J=5.9 Hz, 1H), 7.95 (d, J=8.1 Hz, 1H), 7.32 (d, J=8.0 Hz, 1H), 6.55 (dd, J=5.9, 2.2 Hz, 1H), 6.26 (d, J=2.2 Hz, 1H), 5.16 (s, 2H), 3.93 (s, 3H).

b) 4-((6-(Trifluoromethyl)pyridin-3-yl)methoxy)pyridin-2(1H)-one

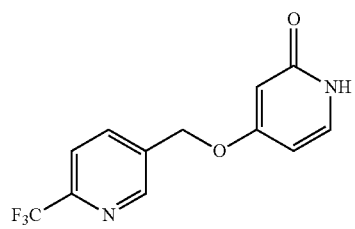

Chemical Formula: C$_{12}$H$_9$F$_3$N$_2$O$_2$
Exact Mass: 270.06
Molecular Weight: 270.21

2-Methoxy-4-((6-(trifluoromethyl)pyridin-3-yl)methoxy)pyridine (3.19 g, 11.2 mmol) was reacted according to the procedure of Example 5 (step b) to provide the title compound (2.04 g, 67%) as a white solid: $^1$H NMR (300 MHz, DMSO-d$_6$) δ 11.2 (br s, 1H), 8.84 (s, 1H), 8.14 (d, J=8.5 Hz, 1H), 7.96 (d, J=8.0 Hz, 1H), 7.28 (d, J=7.3 Hz, 1H), 5.95 (dd, J=7.3, 2.5 Hz, 1H), 5.82 (d, J=2.4 Hz, 1H), 5.25 (s, 2H).

c) tert-Butyl 9-methyl-2-(2-oxo-4-((6-(trifluoromethyl)pyridin-3-yl)methoxy)pyridin-1(2H)-yl)-5,7,8,9-tetrahydro-6H-pyrido[3',4':4,5]pyrrolo[2,3-b]pyridine-6-carboxylate

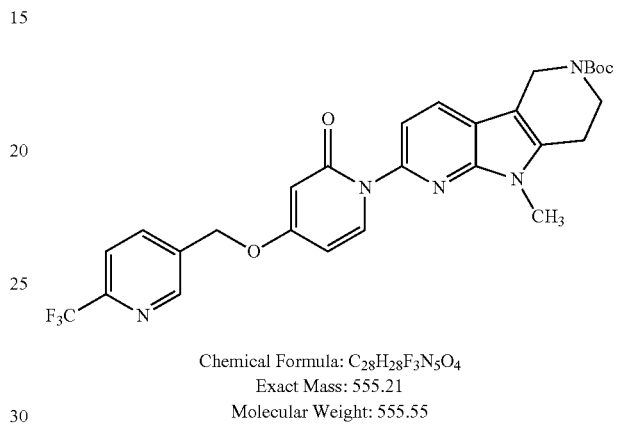

Chemical Formula: C$_{28}$H$_{28}$F$_3$N$_5$O$_4$
Exact Mass: 555.21
Molecular Weight: 555.55 tert-Butyl 2-bromo-9-methyl-5,7,8,9-tetrahydro-6H-pyrido[3',4':4,5]pyrrolo[2,3-b]pyridine-6-carboxylate (0.75 g, 2.0 mmol), 4-((6-(trifluoromethyl)pyridin-3-yl)methoxy)pyridin-2(1H)-one (0.59 g, 2.2 mmol), and Cs$_2$CO$_3$ (0.84 g, 2.6 mmol) were suspended in DMSO (6.0 mL), and the air was removed under vacuum for 15 min. The system was flushed with Ar, and 8-hydroxyquinoline (86 mg, 0.59 mmol) and copper iodide (0.49 g, 2.6 mmol) were added to the suspension. The evacuation/Ar flushing process was repeated twice more, and the reaction mixture was heated at 130° C. for 18 h under N$_2$. The mixture was cooled, diluted with 5.0:3.5:1.5 NH$_4$Cl(aq.)/NH$_4$OH/H$_2$O (70 mL), and the resulting suspension was stirred at ambient temperature for 30 min. The resulting solids were collected by filtration, dissolved in CH$_2$Cl$_2$ (30 mL), and washed with 5.0:3.5:1.5 NH$_4$Cl(aq.)/NH$_4$OH/H$_2$O (2×50 mL). Activated charcoal was added to the organic solution, and the resulting suspension was filtered through a Celite® plug and concentrated to dryness under reduced pressure. Flash chromatography (40 g ISCO column, (1:1 hexanes/EtOAc)/(80:18:2 CH$_2$Cl$_2$/MeOH/NH$_4$OH), 100:0 for 4 column volumes, increased to 50:50 over 12 column volumes and held for 2 column volumes; increased to 0:100 over 10 column volumes and held for 40 column volumes) gave the title compound (0.44 g, 39%) as an off-white solid: $^1$H NMR (300 MHz, DMSO-d$_6$) δ 8.89 (s, 1H), 8.19 (d, J=8.1 Hz, 1H), 8.26-7.95 (m, 2H), 7.84 (s, J=7.8 Hz, 1H), 7.29 (d, J=8.4 Hz, 1H), 6.20 (dd, J=7.5, 2.4 Hz, 1H), 6.04 (d, J=2.7 Hz, 1H), 5.36 (s, 2H), 4.57 (s, 2H), 3.75 (t, J=5.7 Hz, 2H), 3.67 (s, 3H), 2.99-2.81 (m, 2H), 1.42 (s, 9H); ESI MS m/z 556 [M+H]$^+$.

d) 1-(9-Methyl-5,7,8,9-tetrahydro-6H-pyrido[3',4':4,5]pyrrolo[2,3-b]pyridin-2-yl)-4-((6-(trifluoromethyl)pyridin-3-yl)methoxy)pyridin-2(1H)-one

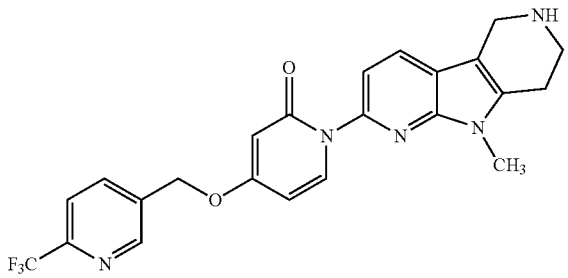

Chemical Formula: $C_{23}H_{20}F_3N_5O_2$
Exact Mass: 455.16
Molecular Weight: 455.43 tert-Butyl 9-methyl-2-(2-oxo-4-((6-(trifluoromethyl)pyridin-3-yl)methoxy)pyridin-1(2H)-yl)-5,7,8,9-tetrahydro-6H-pyrido[3',4':4,5]pyrrolo[2,3-b]pyridine-6-carboxylate (0.43 g, 0.77 mmol) was treated with 1.25 M HCl in MeOH (15 mL), and the resulting solution was stirred at ambient temperature for 18 h. The solution was diluted with Et$_2$O (50 mL). The resulting solids were collected by filtration, dissolved in 10:3 CH$_2$Cl$_2$/MeOH (50 mL), and washed with saturated NaHCO$_3$ solution (50 mL). The aqueous layer was extracted with CH$_2$Cl$_2$ (8×25 mL), and the organic extracts were combined. The remaining solids in the aqueous solution were separated by filtration and washed with MeOH (100 mL). The resulting filtrate was extracted with CH$_2$Cl$_2$ (3×50 mL). All the organic extracts were combined and concentrated to dryness under reduced pressure. The resulting residue was diluted in CH$_2$Cl$_2$, washed with brine (2×20 mL), dried over Na$_2$SO$_4$, filtered, and concentrated to dryness under reduced pressure to provide the title compound (0.27 g, 76%) as an off-white powder: $^1$H NMR (500 MHz, DMSO-d$_6$) δ 8.89 (d, J=1.5 Hz, 1H), 8.19 (dd, J=8.0, 1.5 Hz, 1H), 7.99 (d, J=8.0 Hz, 1H), 7.88 (d, J=8.0 Hz, 1H), 7.83 (d, J=8.0 Hz, 1H), 7.24 (d, J=8.0 Hz, 1H), 6.19 (dd, J=7.5, 2.5 Hz, 1H), 6.03 (s, J=3.0 Hz, 1H), 5.36 (s, 2H), 3.87 (s, 2H), 3.65 (s, 3H), 3.08 (t, J=5.5 Hz, 2H), 2.74 (t, J=5.5 Hz, 2H).

e) 1-(9-Methyl-5,7,8,9-tetrahydro-6H-pyrido[3',4':4,5]pyrrolo[2,3-b]pyridin-2-yl)-4-((6-(trifluoromethyl)pyridin-3-yl)methoxy)pyridin-2(1H)-one hydrochloride

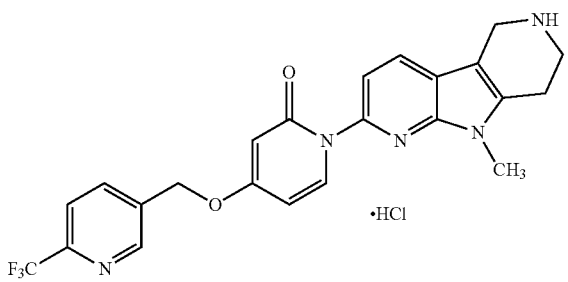

Chemical Formula: $C_{23}H_{21}ClF_3N_5O_2$
Exact Mass: 491.13
Molecular Weight: 491.89

A solution of 1-(9-methyl-5,7,8,9-tetrahydro-6H-pyrido[3',4':4,5]pyrrolo[2,3-b]pyridin-2-yl)-4-((6-(trifluoromethyl)pyridin-3-yl)methoxy)pyridin-2(1H)-one (0.27 g, 0.59 mmol) in MeOH (2.0 mL) was treated with 1.25 M HCl in MeOH (0.47 mL, 0.59 mmol), and the resulting suspension was stirred at ambient temperature for 6 h. The suspension was diluted with Et$_2$O, and the resulting solids were collected by filtration. The filtrate was concentrated, and the resulting residue was dissolved in CH$_2$Cl$_2$ (0.5 mL) and diluted with Et$_2$O (50 mL). The resulting solids were collected by filtration. The solids from both batches were combined in Et$_2$O and the resulting slurry was concentrated to dryness to provide the title compound (0.23 g, 78%) as an off-white powder: 280-278° C. decomp.; $^1$H NMR (500 MHz, DMSO-d$_6$) δ 8.89 (d, J=1.0 Hz, 1H), 8.19 (d, J=8.0, 1.5 Hz, 1H), 8.17-7.80 (m, 4H), 7.33 (d, J=8.5 Hz, 1H), 6.21 (dd, J=7.5, 2.5 Hz, 1H), 6.04 (d, J=2.5 Hz, 1H), 5.36 (s, 2H), 4.22 (s, 2H), 3.69 (s, 3H), 3.41 (t, J=6.0 Hz, 2H), 3.01 (t, J=5.5 Hz, 2H); ESI MS m/z 456 [M+H]; HPLC (Method A)>99% (AUC), t$_R$=13.4 min.

Example 8

Preparation of 1-(9-Methyl-5,7,8,9-tetrahydro-6H-pyrido[3',4':4,5]pyrrolo[2,3-b]pyridin-2-yl)-4-(5-(trifluoromethyl)pyridin-2-yl)pyridin-2(1H)-one hydrochloride a) 2'Methoxy-5-(trifluoromethyl)-2,4'-bipyridine (CAS Registry Number 1108184-24-2) (WO 2009/015037 to Guzzo et al., which is Hereby Incorporated by Reference in its Entirety)

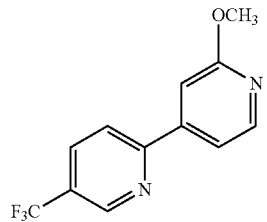

Chemical Formula: $C_{12}H_9F_3N_2O$
Exact Mass: 254.07
Molecular Weight: 254.21

2-Bromo-5-trifluoromethylpyridine (410 mg, 2.13 mmol) and 2-methoxy-4-(4,4,5,5-tetramethyl-1,3,2-dioxaborolan-2-yl)pyridine (500 mg, 1.81 mmol) were reacted according to Example 5 (step a) to provide the title compound (337 mg, 62%) as a white solid: $^1$H NMR (300 MHz, CDCl$_3$) δ 8.96 (s, 1H), 8.31 (d, J=5.4 Hz, 1H), 8.04 (dd, J=8.3, 2.1 Hz, 1H), 7.87 (d, J=8.3 Hz, 1H), 7.51 (dd, J=5.4, 1.4 Hz, 1H), 7.36 (s, 1H), 3.52 (s, 3H).

b) 4-(5-(Trifluoromethyl)pyridin-2-yl)pyridin-2(1H)-one (CAS Registry Number 1108184-25-3) (WO 2009/015037 to Guzzo et al., which is Hereby Incorporated by Reference in its Entirety)

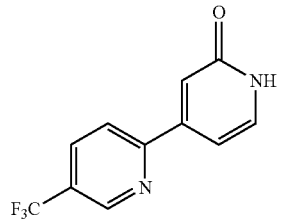

Chemical Formula: $C_{11}H_7F_3N_2O$
Exact Mass: 240.05
Molecular Weight: 240.18

2'-Methoxy-5-(trifluoromethyl)-2,4'-bipyridine (337 mg, 1.32 mmol) was reacted according to Example 5 (step b) to provide the title compound (289 mg, 89%) as a white solid: $^1$H NMR (300 MHz, DMSO-$d_6$) δ 11.08 (s, 1H) 9.10 (s, 1H), 8.35 (dd, J=8.4, 2.1 Hz, 1H), 8.25 (d, J=8.3 Hz, 1H), 7.53 (d, J=6.8, 1H), 7.09 (d, J=1.3 Hz, 1H), 6.90 (dd, J=6.8, 1.6 Hz, 1H).

c) tert-Butyl 9-methyl-2-(2-oxo-4-(5-(trifluoromethyl)pyridin-2-yl)pyridin-1(2H)-yl)-5,7,8,9-tetrahydro-6H-pyrido[3',4':4,5]pyrrolo[2,3-b]pyridine-6-carboxylate

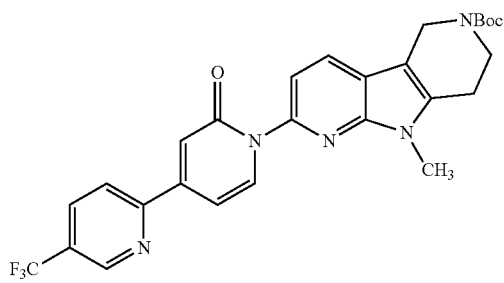

Chemical Formula: $C_{27}H_{26}F_3N_5O_3$
Exact Mass: 525.20
Molecular Weight: 525.52 tert-Butyl 2-bromo-9-methyl-5,7,8,9-tetrahydro-6H-pyrido[3',4':4,5]pyrrolo[2,3-b]pyridine-6-carboxylate (0.19 g, 0.52 mmol), 4-(5-(trifluoromethyl)pyridin-2-yl)pyridin-2(1H)-one (0.14 g, 0.57 mmol), and $K_3PO_4$ (0.22 g, 1.0 mmol) were suspended in 1,4-dioxane (15 mL), and $N_2$ was bubbled through the suspension for 45 min. To the suspension was added (1S,2S) N,N'-bismethyl-1,2-cyclohexane-diamine (20 μL, 0.14 mmol) and copper iodide (50 mg, 0.26 mmol). The reaction mixture was heated at reflux for 20 h under $N_2$. The mixture was cooled, passed through a silica gel plug eluting with 80:18:2 $CH_2Cl_2$/MeOH/$NH_4$OH, and concentrated to dryness under reduced pressure. Flash chromatography (12 g ISCO column, (1:1 hexanes/EtOAc)/(80:18:2 $CH_2Cl_2$/MeOH/$NH_4$OH), 100:0 for 4 column volumes, increased to 50:50 over 20 column volumes and held for 4 column volumes; increased to 0:100 over 10 column volumes and held for 4 column volumes) followed by additional flash chromatography (24 g ISCO column, $CH_2Cl_2$/(80:18:2 $CH_2Cl_2$/MeOH/$NH_4$OH), 100:0 for 4 column volumes, increased to 50:50 over 16 column volumes and held for 4 column volumes; increased to 0:100 over 10 column volumes) gave the title compound (82 mg, 30%) as a yellow film: $^1$H NMR (500 MHz, DMSO-$d_6$) δ 9.15 (s, 1H), 8.43-8.34 (m, 2H), 8.07 (d, J=8.0 Hz, 2H), 7.41 (d, J=8.0 Hz, 1H), 7.31 (d, J=1.5 Hz, 1H), 7.12 (dd, J=7.5, 2.0 Hz, 1H), 4.59 (s, 2H), 3.77 (t, J=5.5 Hz, 2H), 3.70 (s, 3H), 2.90 (t, J=5.5 Hz, 2H), 1.45 (s, 9H).

d) 1-(9-Methyl-5,7,8,9-tetrahydro-6H-pyrido[3',4':4,5]pyrrolo[2,3-b]pyridin-2-yl)-4-(5-(trifluoromethyl)pyridin-2-yl)pyridin-2(1H)-one hydrochloride

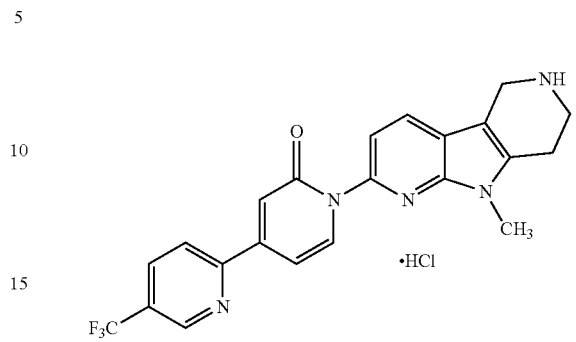

Chemical Formula: $C_{22}H_{19}ClF_3N_5O$
Exact Mass: 461.12
Molecular Weight: 461.87 tert-Butyl 9-methyl-2-(2-oxo-4-(5-(trifluoromethyl)pyridin-2-yl)pyridin-1(2H)-yl)-5,7,8,9-tetrahydro-6H-pyrido[3',4':4,5]pyrrolo[2,3-b]pyridine-6-carboxylate (82 mg, 0.16 mmol) was treated with 1.25 M HCl in MeOH (5.0 mL), and the resulting solution was stirred at ambient temperature for 18 h. The solution was diluted with $Et_2O$, and the resulting solids were collected by filtration to provide the title compound (55 mg, 76%) as a yellow solid: 298-302° C. decomp.; $^1$H NMR (500 MHz, DMSO-$d_6$) δ 9.30 (br s, 1H), 9.15 (t, J=1.0 Hz, 1H), 8.42-8.34 (m, 2H), 8.13 (d, J=8.0 Hz, 1H), 8.08 (d, J=7.0 Hz, 1H), 7.49 (d, J=8.5 Hz, 1H), 7.32 (d, J=2.0 Hz, 1H), 7.13 (dd, J=7.0, 2.0 Hz, 1H), 4.39 (s, 2H), 3.74 (s, 3H), 3.60-3.51 (m, 2H), 3.15 (t, J=6.0 Hz, 2H); ESI MS m/z 426 [M+H]$^+$; HPLC (Method A) 98.8% (AUC), $t_R$=13.7 min.

Example 9

Preparation of 1-(6-Acetyl-9-methyl-5,7,8,9-tetrahydro-6H-pyrido[3',4':4,5]pyrrolo[2,3-b]pyridin-2-yl)-4-(6-(trifluoromethyl)pyridin-3-yl)pyridin-2(1H)-one

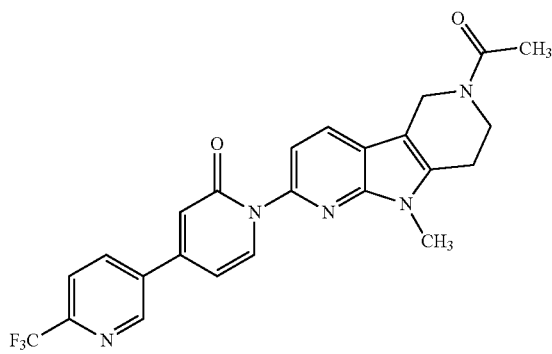

Chemical Formula: $C_{24}H_{20}F_3N_5O_2$
Exact Mass: 467.16
Molecular Weight: 467.44

Triethylamine (40 μL, 0.28 mmol), DMAP (3.5 mg, 0.028 mmol) and acetyl chloride (15 μL, 0.21 mmol) were added to a solution of 1-(9-methyl-5,7,8,9-tetrahydro-6H-pyrido[3',4': 4,5]pyrrolo[2,3-b]pyridin-2-yl)-4-(6-(trifluoromethyl)pyridin-3-yl)pyridin-2(1H)-one hydrochloride (80 mg, 0.14 mmol) in CH$_2$Cl$_2$ (8 mL) and the resulting solution was stirred at ambient temperature for 3 h under N$_2$. The resulting solution was concentrated to dryness under reduced pressure. Flash chromatography (12 g ISCO column, CH$_2$Cl$_2$/(80:18:2 CH$_2$Cl$_2$/MeOH/NH$_4$OH), 100:0 for 2 column volumes, increased to 0:100 over 20 column volumes and held for 14 column volumes) gave the title compound (51 mg, 77%) as a yellow solid and a mixture of rotomers: mp 238-242° C.; $^1$H NMR (500 MHz, DMSO-d$_6$) δ 9.20 (d, J=2.0 Hz, 1H), 8.50 (dd, J=8.0, 2.0 Hz, 1H), 8.11-8.04 (m, 3H), 7.44-7.37 (m, 1H), 7.03 (d, J=1.5 Hz, 1H), 6.86-6.83 (m, 1H), 4.73-4.68 (m, 2H), 3.90-3.83 (m, 2H), 3.71-3.69 (m, 3H), 3.01-2.86 (m, 2H), 2.16-2.12 (m, 3H); ESI MS m/z 468 [M+H]$^+$; HPLC (Method A)>99% (AUC), t$_R$=17.8 min.

Example 10

Preparation of 1-(9-Methyl-5,7,8,9-tetrahydro-6H-pyrido[3',4':4,5]pyrrolo[2,3-b]pyridin-2-yl)-4-(4-(trifluoromethyl)phenyl)pyridin-2(1H)-one hydrochloride a) 4-(4-(Trifluoromethyl)phenyl)pyridine 1-oxide (CAS Registry Number 545396-52-9) (WO 2003/049702 to Bo et al., which is Hereby Incorporated by Reference in its Entirety)

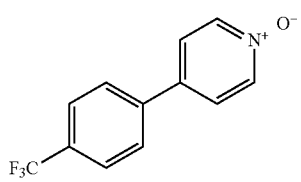

Chemical Formula: C$_{12}$H$_8$F$_3$NO
Exact Mass: 239.06
Molecular Weight: 239.19

4-Chloropyridine-N-oxide (3.0 g, 23 mmol), 4-trifluoromethylphenylboronic acid (6.57 g, 34.6 mmol), K$_2$CO$_3$ (4.8 g, 35 mmol) and PdCl$_2$(dppf) (470 mg, 0.57 mmol) were stirred in DMSO (40 mL) under vacuum for 30 min. The flask was flushed with nitrogen, and the mixture was heated to 80° C. for 10 min. Upon cooling, the mixture was diluted with methylene chloride and washed with 5% lithium chloride solution (5×), dried, concentrated, and the residue was purified by flash column chromatography (40 g ISCO column eluting with methylene chloride and a methanol/ammonia mixture (10:1); gradient 100% methylene chloride to 80% methylene chloride over 30 min at 40 mL/min) to provide the title compound (1.90 g, 34%) as a tan solid: ESI MS m/z 240 [M+H]$^+$.

b) 4-(4-(Trifluoromethyl)phenyl)pyridin-2(1H)-one (CAS Registry Number 942947-10-6) (U.S. Published Patent Application No. 2007/149513 to Chen et al., which is Hereby Incorporated by Reference in its Entirety)

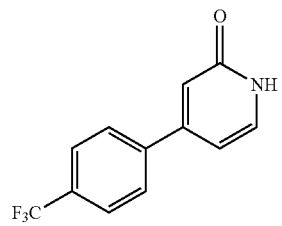

Chemical Formula: C$_{12}$H$_8$F$_3$NO
Exact Mass: 239.06
Molecular Weight: 239.19

4-(4-(Trifluoromethyl)phenyl)pyridine-1-oxide (1.9 g, 7.9 mmol) was heated to 140° C. in acetic anhydride (80 mL) for 5 h. The mixture was concentrated and then heated at 80° C. for 1 h in a mixture of MeOH (20 mL) and aqueous 1 N NaOH (15 mL). The resulting black solution was concentrated to a volume of 15 mL, and the solid was filtered off, rinsed with CH$_2$Cl$_2$ and dried under vacuum to provide the title compound (1.26 g, 66%) as a brown solid: $^1$H NMR (300 MHz, CD$_3$OD) δ 7.80-7.74 (br m, 5H), 6.85-6.66 (br m, 2H).

c) tert-Butyl 9-methyl-2-(2-oxo-4-(4-(trifluoromethyl)phenyl)pyridin-1(2H)-yl)-5,7,8,9-tetrahydro-6H-pyrido[3',4':4,5]pyrrolo[2,3-b]pyridine-6-carboxylate

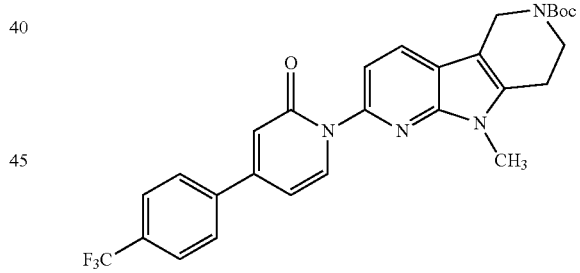

Chemical Formula: C$_{28}$H$_{27}$F$_3$N$_4$O$_3$
Exact Mass: 524.20
Molecular Weight: 524.53 tert-Butyl 2-bromo-9-methyl-5,7,8,9-tetrahydro-6H-pyrido[3',4':4,5]pyrrolo[2,3-b]pyridine-6-carboxylate (0.15 g, 0.41 mmol), 4-(4-(trifluoromethyl)phenyl)pyridin-2(1H)-one (98 mg, 0.41 mmol), and Cs$_2$CO$_3$ (0.15 g, 0.45 mmol) were suspended in DMSO (2.4 mL), and the air was removed under vacuum for 15 min. The system was flushed with Ar, and 8-hydroxyquinoline (18 mg, 0.12 mmol) and copper iodide (94 mg, 0.49 mmol) were added to the suspension. The evacuation/Ar flushing process was repeated twice more, and the reaction mixture was heated at 130° C. for 18 h under N$_2$. The mixture was cooled, diluted with 5.0:3.5:1.5 NH$_4$Cl(aq.)/ NH$_4$OH/H$_2$O (70 mL), and the resulting solution was stirred at ambient temperature for 30 min, extracted with CH$_2$Cl$_2$ (3×20 mL), and washed with 5.0:3.5:1.5 NH₄Cl(aq.)/ NH₄OH/H₂O (4×20 mL). The resulting organic solution was dried over Na₂SO₄, filtered and concentrated to dryness under reduced pressure. Flash chromatography (12 g ISCO column, (1:1 hexanes/EtOAc)/(80:18:2 CH₂Cl₂/MeOH/NH₄OH), 100:0 for 48 mL, increased to 50:50 over 240 mL and held for 48 mL; increased to 0:100 over 120 mL) gave the title compound (0.14 g, 63%) as a yellow powder: ¹H NMR (300 MHz, DMSO-d₆) δ 8.09-8.80 (m, 4H), 7.88 (d, J=8.1 Hz, 2H), 7.39 (d, J=8.1 Hz, 1H), 6.90 (d, J=1.8 Hz, 1H), 6.77 (dd, J=7.5, 2.1 Hz, 1H), 4.59 (s, 2H), 3.77 (t, J=6.0 Hz, 2H), 3.70 (s, 3H), 2.90 (t, J=4.8 Hz, 2H), 1.45 (s, 9H); ESI MS m/z 525 [M+H]⁺.

d) 1-(9-Methyl-5,7,8,9-tetrahydro-6H-pyrido[3',4':4,5]pyrrolo[2,3-b]pyridin-2-yl)-4-(4-(trifluoromethyl)phenyl)pyridin-2(1H)-one

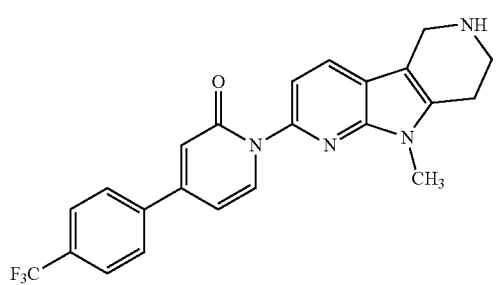

Chemical Formula: C₂₃H₁₉F₃N₄O
Exact Mass: 424.15
Molecular Weight: 424.42 tert-Butyl 9-methyl-2-(2-oxo-4-(4-(trifluoromethyl)phenyl)pyridin-1(2H)-yl)-5,7,8,9-tetrahydro-6H-pyrido[3',4':4,5]pyrrolo[2,3-b]pyridine-6-carboxylate (0.14 g, 0.26 mmol) was treated with 1.25 M HCl in MeOH (6.0 mL), and the resulting suspension was stirred at ambient temperature for 18 h. To the suspension was added CH₂Cl₂ (1.0 mL) and 1.25 M HCl in MeOH (2.0 mL), and the resulting solution was stirred at ambient temperature for 18 h. The solution was concentrated, diluted with CH₂Cl₂ (30 mL), washed with saturated NaHCO₃ solution (2×10 mL), dried over Na₂SO₄, filtered, and concentrated to dryness under reduced pressure. Flash chromatography (12 g ISCO column, CH₂Cl₂/(80:18:2 CH₂Cl₂/MeOH/NH₄OH), 100:0 for 4 column volumes, increased to 50:50 over 20 column volumes and held for 4 column volumes; increased to 0:100 over 10 column volumes and held for 30 column volumes) followed by preparative HPLC (Phenomenex Luna C18 (2), 250.0×50.0 mm, 10 micron, H₂O with 0.05% TFA and CH₃CN with 0.05% TFA) gave the title compound (51 mg, 46%) as a yellow powder: ¹H NMR (500 MHz, DMSO-d₆) δ 8.06-8.00 (m, 3H), 7.93 (d, J=8.0 Hz, 1H), 7.88 (d, J=8.0 Hz, 2H), 7.35 (d, J=8.0 Hz, 1H), 6.89 (d, J=1.5 Hz, 1H), 6.76 (dd, J=7.5, 2.0 Hz, 1H), 3.89 (s, 2H), 3.67 (s, 3H), 3.08 (t, J=5.5 Hz, 2H), 2.75 (t, J=5.5 Hz, 2H).

e) 1-(9-Methyl-5,7,8,9-tetrahydro-6H-pyrido[3',4':4,5]pyrrolo[2,3-b]pyridin-2-yl)-4-(4-(trifluoromethyl)phenyl)pyridin-2(1H)-one hydrochloride

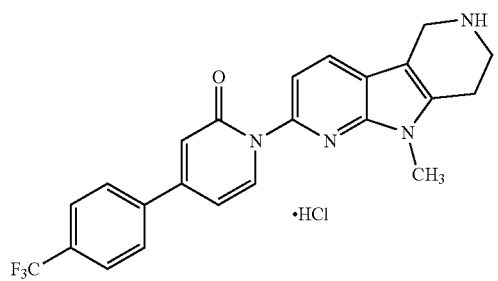

Chemical Formula: C₂₃H₂₀ClF₃N₄O
Exact Mass: 460.13
Molecular Weight: 460.88

A solution of 1-(9-methyl-5,7,8,9-tetrahydro-6H-pyrido[3',4':4,5]pyrrolo[2,3-b]pyridin-2-yl)-4-(4-(trifluoromethyl)phenyl)pyridin-2(1H)-one (50 mg, 0.12 mmol) in MeOH (2.0 mL) was treated with 1.25 M HCl in MeOH (94 μL, 0.12 mmol), and the resulting solution was stirred at ambient temperature for 18 h. The solution was concentrated to dryness to provide the title compound (45 mg, 82%) as a bright yellow powder: mp 278-281° C. decomp.; ¹H NMR (500 MHz, DMSO-d₆) δ 8.06-8.00 (m, 4H), 7.88 (d, J=8.0 Hz, 2H), 7.42 (d, J=3.0 Hz, 1H), 6.90 (d, J=2.0 Hz, 1H), 6.78 (dd, J=7.0, 2.0 Hz, 1H), 4.19 (s, 2H), 3.71 (s, 3H), 3.37 (t, J=5.5 Hz, 2H), 2.99 (t, J=5.5 Hz, 2H); ESI MS m/z 425 [M+H]⁺; HPLC (Method A) 98.9% (AUC), t$_R$=14.8 min.

Example 11

Preparation of 1-(6-Acetyl-9-methyl-5,7,8,9-tetrahydro-6H-pyrido[3',4':4,5]pyrrolo[2,3-b]pyridin-2-yl)-4-(benzyloxy)pyridin-2(1H)-one

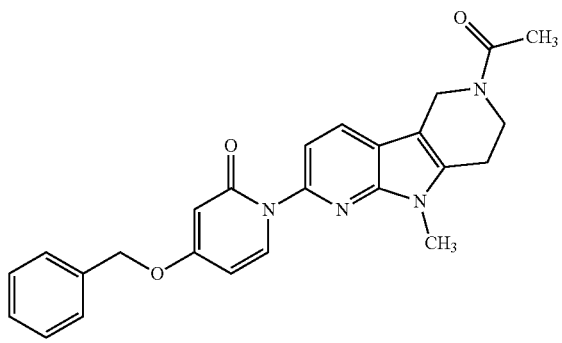

Chemical Formula: C₂₅H₂₄N₄O₃
Exact Mass: 428.18
Molecular Weight: 428.48

Triethylamine (33 μL, 0.24 mmol), DMAP (5.8 mg, 0.048 mmol) and acetyl chloride (25 μL, 0.36 mmol) were added to a solution of 4-(benzyloxy)-1-(9-methyl-5,7,8,9-tetrahydro-6H-pyrido[3',4':4,5]pyrrolo[2,3-b]pyridin-2-yl)pyridin-2(1H)-one (93 mg, 0.24 mmol) in CH₂Cl₂ (14 mL) and the resulting solution was stirred at ambient temperature for 2 h under N₂. The resulting solution was concentrated to dryness under reduced pressure. Flash chromatography (12 g ISCO column, CH₂Cl₂/(80:18:2 CH₂Cl₂/MeOH/NH₄OH), 100:0 for 2 column volumes, increased to 0:100 over 20 column volumes and held for 5 column volumes) gave the title compound (86 mg, 83%) as an off-white powder and a mixture of rotomers: mp 206-208° C.; ¹H NMR (500 MHz, DMSO-d₆) δ 8.01 (t, J=8.5 Hz, 1H), 7.80 (dd, J=7.5, 2.5 Hz, 1H), 7.49-7.36 (m, 5H), 7.33-7.26 (m, 1H), 6.15 (dd, J=8.0, 3.0 Hz, 1H), 5.98 (d, J=2.5 Hz, 1H), 5.16 (s, 2H), 4.71-4.66 (m, 2H), 3.90-3.81 (m, 2H), 3.67 (m, 3H), 3.00-2.86 (m, 2H), 2.16-2.10 (m, 3H); ESI MS m/z 429 [M+H]; HPLC (Method A)>99% (AUC), $t_R$=18.2 min.

Example 12

Preparation of 1-(7,9-Dimethyl-5,7,8,9-tetrahydro-6H-pyrido[3',4':4,5]pyrrolo[2,3-b]pyridin-2-yl)-4-(4-fluorophenethyl)piperazin-2-one hydrochloride a) 4-(4-Fluorophenethyl)piperazin-2-one

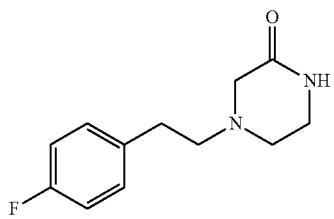

Chemical Formula: C₁₂H₁₅FN₂O
Exact Mass: 222.12
Molecular Weight: 222.26 piperazinone (1.20 g, 12.1 mmol), 1-fluoro-4-(2-chloroethyl)benzene (2.45 g, 12.1 mmol) and i-Pr₂NEt (3.25 g, 4.5 ml, 25 mmol) were combined in acetonitrile (25 mL) and heated to 85° C. for 2 h. The mixture was concentrated and partitioned between H₂O (20 mL) and CH₂Cl₂ (20 mL), and the organic layer was removed. The aqueous layer was extracted with CH₂Cl₂ (3×20 mL), the combined organics were concentrated, and the residue was dissolved in 2 N HCl (50 mL). This acidic mixture was washed with CH₂Cl₂ (3×20 mL) and then made basic with 6 N NaOH. The basic mixture was extracted with CH₂Cl₂ (3×20 mL), and the extracts were combined, dried and concentrated to provide the title compound (1.30 g, 48%) as a white solid: ¹H NMR (300 MHz, CDCl₃) δ 7.18-7.13 (m, 2H), 7.00-6.94 (m, 2H), 6.45 (s, 1H), 3.39-3.35 (m, 2H), 3.20 (s, 2H), 2.78-2.62 (m, 6H).

b) 2-Bromo-6-(1-methylhydrazinyl)pyridine

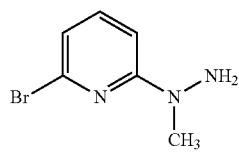

Chemical Formula: C₆H₈BrN₃
Exact Mass: 200.99
Molecular Weight: 202.05

A suspension of 2,6-dibromopyridine (10.0 g, 42.0 mmol) in anhydrous methylhydrazine (10 mL) was heated at 100° C. for 2 h. The mixture was cooled to room temperature and washed with water (3×20 mL). The combined organic extracts were dried over sodium sulfate, filtered, and concentrated under reduced pressure. Purification by flash column chromatography (silica gel, hexanes/EtOAc, 80:20) gave the title compound (5.70 g, 66%) as white solid: ¹H NMR (500 MHz, CDCl₃) δ 7.30-7.26 (dd, J=8.5, 7.8 Hz, 1H), 6.83 (d, J=8.0 Hz, 1H), 6.73 (d, J=7.0 Hz, 1H), 4.03 (br s, 2H), 3.36 (s, 3H).

c) 2-Bromo-6-(1-methyl-2-(2-methylpiperidin-4-ylidene)hydrazinyl)pyridine

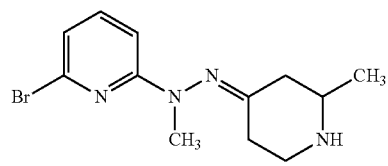

Chemical Formula: C₁₂H₁₇BrN₄
Exact Mass: 296.06
Molecular Weight: 297.19

2-Bromo-6-(1-methylhydrazinyl)pyridine (1.58 g, 7.80 mmol) and 2-methylpiperidin-4-one (975 mg, 8.63 mmol) were heated in EtOH (10 mL) at reflux for 16 h, and then the mixture was concentrated to provide the title compound as a white foam, carried forward crude assuming 100% yield: ESI MS m/z 282 [M+H]⁺.

d) tert-Butyl 2-bromo-7,9-dimethyl-5,7,8,9-tetrahydro-6H-pyrido[3',4':4,5]pyrrolo[2,3-b]pyridine-6-carboxylate

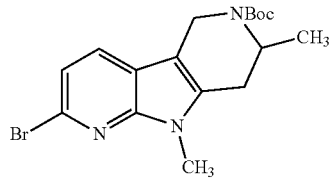

Chemical Formula: C₁₇H₂₂BrN₃O₂
Exact Mass: 379.09
Molecular Weight: 380.28

2-Bromo-6-(1-methyl-2-(2-methylpiperidin-4-ylidene) hydrazinyl)pyridine from step b above was combined with para-toluenesulphonic acid (3.1 g, 16 mmol) and heated to 160° C. for 10 minutes. The mixture was allowed to cool and isopropanol (20 mL), water (8 mL), potassium carbonate (5.00 g, 36.2 mmol), and di-tert-butyl dicarbonate (2.55 g, 11.7 mmol) were added. After stirring for 16 h, the mixture was partitioned between methylene chloride and water, and the organic layer was removed, dried and concentrated. The residue was purified by column chromatography eluting with ethyl acetate/hexanes (1:4) to provide the title compound (650 mg, 22%) as a white foam: ESI MS m/z 380 [M+H]⁺.

e) tert-Butyl 7,9-dimethyl-2-(2-oxo-4-(4-fluorophenethyl)piperazin-1-yl)-5,7,8,9-tetrahydro-6H-pyrido[3',4':4,5]pyrrolo[2,3-b]pyridine-6-carboxylate

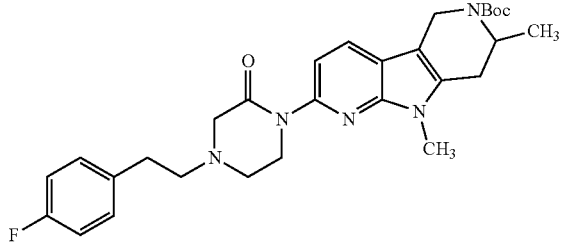

Chemical Formula: $C_{29}H_{36}FN_5O_3$
Exact Mass: 521.28
Molecular Weight: 521.63 tert-Butyl 2-bromo-7,9-dimethyl-5,7,8,9-tetrahydro-6H-pyrido[3',4':4,5]pyrrolo[2,3-b]pyridine-6-carboxylate (2-((4 mg, 0.640 mmol) and 4-(4-fluorophenethyl)piperazin-2-one (141 mg, 0.640 mmol) were reacted following the procedure for Example 2 (step e) to provide the title compound (245 mg, 73%) as a colorless oil: ESI MS m/z 522 [M+H]+.

f) 1-(7,9-Dimethyl-5,7,8,9-tetrahydro-6H-pyrido[3',4':4,5]pyrrolo[2,3-h]pyridin-2-yl)-4-(4-fluorophenethyl)piperazin-2-one hydrochloride

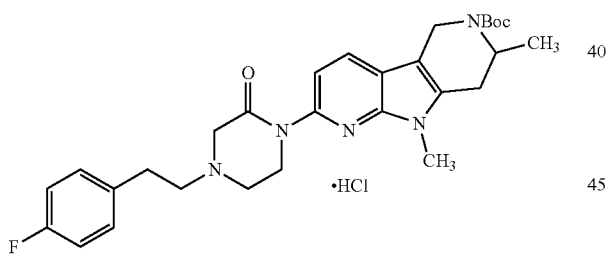

Chemical Formula: $C_{24}H_{29}ClFN_5O$
Exact Mass: 457.20
Molecular Weight: 457.97 tert-Butyl 7,9-dimethyl-2-(2-oxo-4-(4-fluorophenethyl)piperazin-1-yl)-5,7,8,9-tetrahydro-6H-pyrido[3',4':4,5]pyrrolo[2,3-b]pyridine-6-carboxylate (245 mg, 0.470 mmol) was reacted following the procedure for Example 2 (steps f and g) to provide the title compound (105 mg, 49%) as a white solid: mp 252-256° C.; $^1$H NMR (300 MHz, CD$_3$OD) δ 7.94 (d, J=8.3 Hz, 1H), 7.43 (d, J=8.3 Hz, 1H), 7.33-7.28 (m, 2H), 7.06-7.00 (m, 2H), 4.53 (d, J=14.7 Hz, 1H), 4.42 (d, J=14.7 Hz, 1H), 4.11-4.07 (m, 2H), 3.84-3.79 (m, 1H), 3.75 (s, 3H), 3.69-3.51 (m, 2H), 3.37-3.33 (m, 1H), 3.26-3.07 (m, 2H), 2.98-2.89 (m, 5H), 1.59 (d, J=6.5 Hz, 3H); ESI MS m/z 422 [M+H]+; HPLC (Method B)>99% (AUC), $t_R$=10.1 min.

Example 13

Preparation of 4-(Benzyloxy)-1-(7,9-dimethyl-5,7,8,9-tetrahydro-6H-pyrido[3',4':4,5]pyrrolo[2,3-b]pyridin-2-yl)pyridin-2(1H)-one hydrochloride a) tert-Butyl 2-(4-(benzyloxy)-2-oxopyridin-1(2H)-yl)-7,9-dimethyl-5,7,8,9-tetrahydro-6H-pyrido[3',4':4,5]pyrrolo[2,3-b]pyridine-6-carboxylate

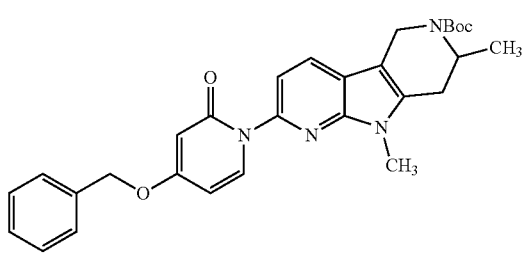

Chemical Formula: $C_{29}H_{32}N_4O_4$
Exact Mass: 500.24
Molecular Weight: 500.59 tert-Butyl 2-bromo-7,9-dimethyl-5,7,8,9-tetrahydro-6H-pyrido[3',4':4,5]pyrrolo[2,3-b]pyridine-6-carboxylate (200 mg, 0.520 mmol) and 4-(benzyloxy)pyridin-2(1H)-one (115 mg, 0.520 mmol) were reacted following the procedure for Example 2 (step e) to provide the title compound (150 mg, 57%) as a yellow oil: ESI MS m/z 501 [M+H]+.

b) 4-(Benzyloxy)-1-(7,9-dimethyl-5,7,8,9-tetrahydro-6H-pyrido[3',4':4,5]pyrrolo[2,3-b]pyridin-2-yl)pyridin-2(1H)-one hydrochloride

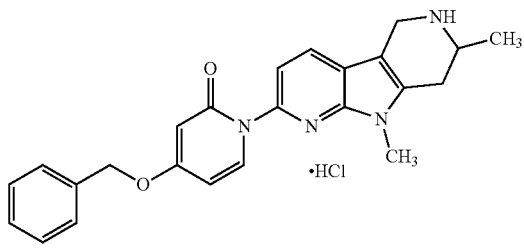

Chemical Formula: $C_{24}H_{25}ClN_4O_2$
Exact Mass: 436.17
Molecular Weight: 436.93 tert-Butyl 2-(4-(benzyloxy)-2-oxopyridin-1(2H)-yl)-7,9-dimethyl-5,7,8,9-tetrahydro-6H-pyrido[3',4':4,5]pyrrolo[2,3-b]pyridine-6-carboxylate (150 mg, 0.300 mmol) was reacted following the procedure for Example 2 (steps f and g) to provide the title compound (48 mg, 36%) as a white solid: mp 285-289° C.; $^1$H NMR (300 MHz, DMSO-d$_6$) δ 9.73-9.51 (m, 1H), 9.51-9.00 (m, 1H), 8.08 (d, J=8.3 Hz, 1H), 7.81 (d, J=7.7 Hz, 1H), 7.49-7.34 (m, 6H), 6.19-6.15 (dd, J=7.8, 2.7 Hz, 1H), 5.99 (d, J=2.7 Hz, 1H), 5.17 (s, 2H), 4.48-4.42 (m, 1H), 4.40-4.17 (m, 1H), 3.70-3.58 (m, 4H), 3.30-3.22 (m, 1H), 2.93-2.84 (m, 1H), 1.48 (d, J=6.5 Hz, 3H); ESI MS m/z 401 [M+H]+; HPLC (Method B)>99% (AUC), $t_R$=12.7 min.

Example 14

Preparation of 1-(7,9-Dimethyl-5,7,8,9-tetrahydro-6H-pyrido[3',4':4,5]pyrrolo[2,3-b]pyridin-2-yl)-4-((5-fluoropyridin-2-yl)methoxy)pyridin-2(1H)-one hydrochloride a) tert-Butyl 7,9-dimethyl-2-(4-((5-fluoropyridin-2-yl)methoxy)-2-oxopyridin-1(2H)-yl)-5,7,8,9-tetrahydro-6H-pyrido[3',4':4,5]pyrrolo[2,3-b]pyridine-6-carboxylate

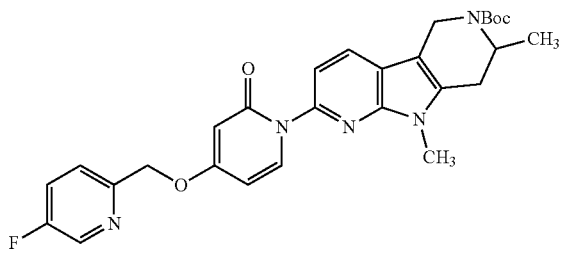

Chemical Formula: $C_{28}H_{30}FN_5O_4$
Exact Mass: 519.23
Molecular Weight: 519.57 tert-Butyl 2-bromo-7,9-dimethyl-5,7,8,9-tetrahydro-6H-pyrido[3',4':4,5]pyrrolo[2,3-b]pyridine-6-carboxylate (200 mg, 0.520 mmol) and 4-((5-fluoropyridin-2-yl)methoxy)pyridin-2(1H)-one (115 mg, 0.520 mmol) were reacted following the procedure for Example 2 (step e) to provide the title compound (198 mg, 73%) as a yellow oil: ESI MS m/z 520 [M+H]+.

b) 1-(7,9-Dimethyl-5,7,8,9-tetrahydro-6H-pyrido[3',4':4,5]pyrrolo[2,3-b]pyridin-2-yl)-4-((5-fluoropyridin-2-yl)methoxy)pyridin-2(1H)-one hydrochloride

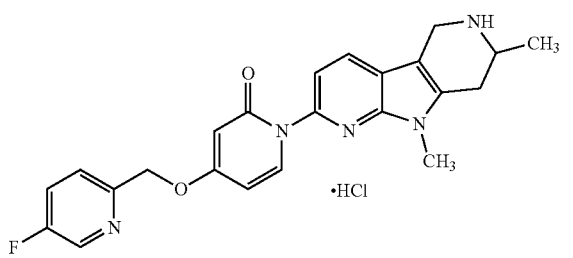

Chemical Formula: $C_{23}H_{23}ClFN_5O_2$
Exact Mass: 455.15
Molecular Weight: 455.91 tert-Butyl 7,9-dimethyl-2-(4-((5-fluoropyridin-2-yl)methoxy)-2-oxopyridin-1(2H)-yl)-5,7,8,9-tetrahydro-6H-pyrido[3',4':4,5]pyrrolo[2,3-b]pyridine-6-carboxylate (198 mg, 0.38 mmol) was reacted following the procedure for Example 2 (steps f and g) to provide the title compound (67 mg, 38%) as a white solid: mp 288-292° C.; 1H NMR (300 MHz, DMSO-d6) δ 9.77-9.62 (m, 1H), 9.50-9.20 (m, 1H), 8.63 (d, J=2.9 Hz, 1H), 8.08-8.06 (d, J=8.2 Hz, 1H), 7.88-7.79 (m, 2H), 7.68-7.63 (dd, J=8.7, 4.5 Hz, 1H), 7.35 (d, J=8.3 Hz, 1H), 6.26-6.25 (dd, J=7.8, 2.8 Hz, 1H), 6.00 (d, J=9.1 Hz, 1H), 5.23 (s, 2H), 4.47-4.28 (m, 1H), 4.35-4.28 (m, 1H), 3.75-3.65 (m, 4H), 3.24-3.13 (dd, J=7.3, 4.5 Hz, 1H), 2.93-2.84 (m, 1H), 1.48 (d, J=7.5 Hz, 3H); ESI MS m/z 420 [M+H]+; HPLC (Method B)>99% (AUC), $t_R$=11.3 min.

Example 15

Preparation of 4-((2,4-Dichlorophenyl)methoxy)-1-(9-methyl-5,7,8,9-tetrahydro-6H-pyrido[3',4':4,5]pyrrolo[2,3-b]pyridin-2-yl)pyridin-2(1H)-one hydrochloride a) 4-(2,4-Dichlorobenzyloxy)pyridin-2(1H)-one (CAS Registry Number 1182243-20-4) (WO 2007/043,835 to Kim et al., which is Hereby Incorporated by Reference in its Entirety)

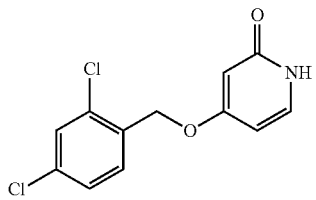

Chemical Formula: $C_{12}H_9Cl_2NO_2$
Exact Mass: 269.00
Molecular Weight: 270.11

A suspension of (2,4-dichlorophenyl)methanol (4.10 g, 23.2 mmol), 2-chloro-4-iodopyridine (5.05 g, 21.1 mmol), $Cs_2CO_3$ (8.94 g, 27.4 mmol), CuI (4.01 g, 21.1 mmol) and 1,10-phenanthroline (760 mg, 4.22 mmol) in toluene (20 mL) was degassed by bubbling $N_2$ through the suspension for 15 min. The suspension was put under $N_2$, and heated at 105° C. for 18 h. The suspension was cooled, EtOAc (50 mL) was added, and the resulting suspension was passed through a plug of $SiO_2$. The resulting solution was concentrated under reduced pressure. Flash chromatography on silica gel (hexanes/(1:1 EtOAc/hexanes), 100:0 to 0:100) afforded a white solid. A suspension of the white solid and $NH_4OAc$ (6.13 g, 79.5 mmol) in 1:1 $HCO_2H/H_2O$ (40 mL) was heated at reflux with stirring for 4 d. The solution was cooled and concentrated under reduced pressure. The resulting residue was made basic with saturated $NaHCO_3$ solution and the resulting suspension was filtered. The solid was washed with $H_2O$ and dried under reduced pressure. Flash chromatography on silica gel ((1:1 EtOAc/hexanes)/(9:0.9:0.1 $CH_2Cl_2$/MeOH/$NH_4OH$), 100:0 to 0:100) afforded 1.36 g (24%) of the title compound as a white solid: 1H NMR (300 MHz, DMSO-d6) δ 11.16 (br s, 1H), 7.71 (d, J=2.1 Hz, 1H), 7.61 (d, J=8.1 Hz, 1H), 7.50 (dd, J=8.4, 2.1 Hz, 1H), 7.26 (d, J=7.2 Hz, 1H), 5.91 (dd, J=7.5, 2.7 Hz, 1H), 5.81 (d, J=2.4 Hz, 1H), 5.10 (s, 2H).

b) 4-((2,4-Dichlorophenyl)methoxy)-1-(9-methyl-5,7,8,9-tetrahydro-6H-pyrido[3',4':4,5]pyrrolo[2,3-b]pyridin-2-yl)pyridin-2 (1H)-one hydrochloride

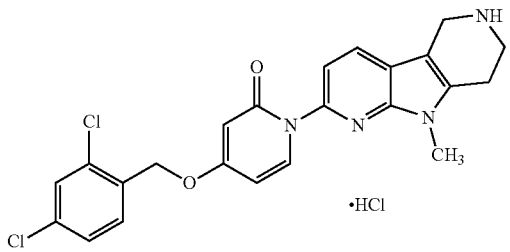

Chemical Formula: $C_{23}H_{21}Cl_3N_4O_2$
Exact Mass: 490.07
Molecular Weight: 491.80

A suspension of 4-(2,4-dichlorobenzyloxy)pyridin-2(1H)-one (104 mg, 0.386 mmol), tert-butyl 2-bromo-9-methyl-5,7,8,9-tetrahydro-6H-pyrido[3',4':4,5]pyrrolo[2,3-b]pyridine-6-carboxylate (155 mg, 0.425 mmol), CuI (88 mg, 0.463 mmol), 8-hydroxyquinoline (11 mg, 0.077 mmol) and $Cs_2CO_3$ (139 mg, 0.386 mmol) in DMSO (10 mL) was degassed under reduced pressure for 45 min. The suspension was put under $N_2$ and stirred at 135° C. for 16 h. The suspension was cooled, 9:0.9:0.1 $CH_2Cl_2$/MeOH/$NH_4OH$ was added and the resulting suspension was stirred at 25° C. for 30 min. The suspension was passed through a plug of silica gel, and the filtrate was washed with brine. Activated carbon was added to the solution, and the resulting suspension was filtered. The filtrate was dried over $Na_2SO_4$ and concentrated under reduced pressure. Flash chromatography on silica gel ((1:1 EtOAc/hexanes)/(9:0.9:0.1 $CH_2Cl_2$/MeOH/$NH_4OH$) afforded a clear residue. 2 N HCl in $Et_2O$ (100 mL) was added to a solution of the clear oil in $CH_2Cl_2$ (5 mL) under $N_2$, and the resulting suspension was stirred at 25° C. for 21 h. The suspension was filtered under $N_2$, and the solid was washed with $Et_2O$. The suspension was concentrated, and the residue was diluted with 1:1 $CH_2Cl_2$/MeOH (1 mL) and $Et_2O$ (10 mL). The resulting suspension was filtered, and the solid was diluted with $CH_2Cl_2$. The resulting solution was washed with aqueous saturated $NaHCO_3$ solution and concentrated under reduced pressure. Flash chromatography on silica gel ((1:1 EtOAc/hexanes)/(9:0.9:0.1 $CH_2Cl_2$/MeOH/$NH_4OH$)) afforded a white solid. 2 N HCl in $Et_2O$ (0.05 mL, 0.1 mmol) was added to a solution of the white solid in $CH_2Cl_2$ (5 mL) under $N_2$, and the resulting suspension was stirred at 25° C. for 15 min. The suspension was concentrated under reduced pressure, and the material was freeze dried to afford 44 mg (25%) of the title compound as a white solid: $^1$H NMR (500 MHz, DMSO-$d_6$) δ 9.22 (s, 2H), 8.07 (d, J=8.5 Hz, 1H), 7.84 (d, J=7.5 Hz, 1H), 7.74 (d, J=2.5 Hz, 1H), 7.67 (d, J=8.0 Hz, 1H), 7.53 (dd, J=8.0, 2.0 Hz, 1H), 7.38 (d, J=8.0 Hz, 1H), 6.19 (dd, J=8.0, 2.5 Hz, 1H), 6.04 (d, J=3.0 Hz, 1H), 5.21 (s, 2H), 4.38 (br s, 2H), 3.72 (s, 3H), 3.58-3.53 (m, 2H), 3.16-3.11 (m, 2H); ESI MS m/z 455 [M+H]$^+$.

Example 16

Preparation of 4-((2,4-Difluorophenyl)methoxy)-1-(9-methyl-5,7,8,9-tetrahydro-6H-pyrido[3',4':4,5]pyrrolo[2,3-b]pyridin-2-yl)pyridin-2(1H)-one hydrochloride a) 4-(2,4-Difluorobenzyloxy)pyridin-2(1H)-one (CAS Registry Number 586373-58-2) (WO 2003/068230 to Devadas et al., which is Hereby Incorporated by Reference in its Entirety)

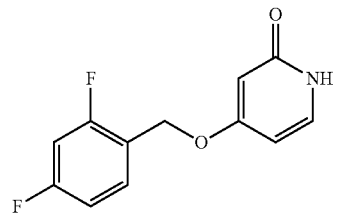

Chemical Formula: $C_{12}H_9F_2NO_2$
Exact Mass: 237.06
Molecular Weight: 237.20

A suspension of (2,4-difluorophenyl)methanol (4.86 g, 33.7 mmol), 2-chloro-4-iodopyridine (7.35 g, 30.7 mmol), $Cs_2CO_3$ (14.3 g, 43.8 mmol), CuI (5.83 g, 30.7 mmol) and 1,10-phenanthroline (1.11 g, 6.14 mmol) in toluene (20 mL) was degassed by bubbling $N_2$ through the suspension for 15 min. The suspension was put under $N_2$, and heated at 105° C. for 18 h. The suspension was cooled, EtOAc (50 mL) was added, and the resulting suspension was passed through a plug of $SiO_2$. The resulting solution was concentrated under reduced pressure. Flash chromatography on silica gel (hexanes/(1:1 EtOAc/hexanes), 100:0 to 0:100) afforded a white solid. A suspension of the white solid and $NH_4OAc$ (8.21 g, 107 mmol) in 1:1 $HCO_2H/H_2O$ (40 mL) was heated at reflux with stirring for 4 d. The solution was cooled and concentrated under reduced pressure. The resulting residue was made basic with saturated $NaHCO_3$ solution, and the resulting suspension was filtered. The solid was washed with $H_2O$ and dried under reduced pressure to afford 3.16 g (44%) of the title compound as a white solid: $^1$H NMR (300 MHz, DMSO-$d_6$) δ 11.14 (br s, 1H), 7.62 (br dd, J=15.3, 8.7 Hz, 1H), 7.33 (ddd, J=10.5, 10.5, 2.4 Hz, 1H), 7.25 (d, J=7.2 Hz, 1H), 7.12 (ddd, J=8.4, 8.4, 1.8 Hz, 1H), 5.91-5.82 (m, 2H), 5.06 (s, 2H).

b) 4-((2,4-Difluorophenyl)methoxy)-1-(9-methyl-5,7,8,9-tetrahydro-6H-pyrido[3',4':4,5]pyrrolo[2,3-b]pyridin-2-yl)pyridin-2(1H)-one hydrochloride

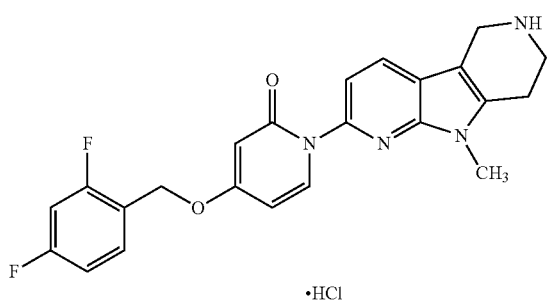

Chemical Formula: $C_{23}H_{21}ClF_2N_4O_2$
Exact Mass: 482.13
Molecular Weight: 458.89

A suspension of 4-(2,4-difluorobenzyloxy)pyridin-2(1H)-one (116 mg, 0.487 mmol), tert-butyl 2-bromo-9-methyl-5,7,8,9-tetrahydro-6H-pyrido[3',4':4,5]pyrrolo[2,3-b]pyridine-6-carboxylate (196 mg, 0.536 mmol), CuI (111 mg, 0.584 mmol), 8-hydroxyquinoline (14 mg, 0.097 mmol) and Cs$_2$CO$_3$ (175 mg, 0.536 mmol) in DMSO (10 mL) was degassed under reduced pressure for 45 min. The suspension was put under N$_2$ and stirred at 135° C. for 20 h. The suspension was cooled, 9:0.9:0.1 CH$_2$Cl$_2$/MeOH/NH$_4$OH was added, and the resulting suspension was stirred at 25° C. for 30 min. The suspension was passed through a plug of silica gel, and the filtrate was washed with brine. Activated carbon was added to the solution, and the resulting suspension was filtered. The filtrate was dried over Na$_2$SO$_4$ and concentrated under reduced pressure. Flash chromatography on silica gel (Et$_2$O/(8:1.9:0.1 Et$_2$O/MeOH/NH$_4$OH)) afforded a clear wax. 2 N HCl in Et$_2$O (100 mL) was added to a solution of the clear wax in CH$_2$Cl$_2$ (10 mL) under N$_2$, and the resulting suspension was stirred at 25° C. overnight. The suspension was filtered under N$_2$, and the solid was washed with Et$_2$O. The solid was put in a vacuum oven at 40° C. for 16 h to afford 119 mg (58%) of the title compound as a white solid: mp 206-210° C.; $^1$H NMR (500 MHz, DMSO-d$_6$) δ 9.28 (s, 2H), 8.07 (d, J=8.5 Hz, 1H), 7.82 (d, J=7.5 Hz, 1H), 7.67 (dd, J=15.0, 8.5 Hz, 1H), 7.40-7.33 (m, 2H), 7.18 (ddd, J=8.5, 8.5, 2.0 Hz, 1H), 6.15 (dd, J=8.5, 2.5 Hz, 1H), 6.07 (d, J=2.5 Hz, 1H), 5.17 (s, 2H), 4.37 (br s, 2H), 3.72 (s, 3H), 3.58-3.52 (m, 2H), 3.14 (t, J=5.5 Hz, 2H); ESI MS m/z 423 [M+H]$^+$.

Example 17

Preparation of (−)-4-(Benzyloxy)-1-(7,9-dimethyl-5,7,8,9-tetrahydro-6H-pyrido[3',4':4,5]pyrrolo[2,3-b]pyridin-2-yl)pyridin-2(1H)-one hydrochloride a) tert-Butyl 2-methyl-4-oxopiperidine-1-carboxylate (Enantiomer B) (CAS Registry Number 190906-92-4) (WO 2006/024517 to Bently et al., which is Hereby Incorporated by Reference in its Entirety)

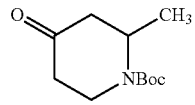

Chemical Formula: C$_{11}$H$_{19}$NO$_3$
Exact Mass: 213.14
Molecular Weight: 213.27

This compound was prepared in accordance with the procedure of Bently et al., WO 2006/024517 (Description 157), which is hereby incorporated by reference in its entirety.

b) tert-Butyl 2-bromo-7,9-dimethyl-5,7,8,9-tetrahydro-6H-pyrido[3',4':4,5]pyrrolo[2,3-b]pyridine-6-carboxylate (Enantiomer B)

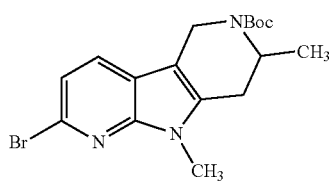

Chemical Formula: C$_{17}$H$_{22}$BrN$_3$O$_2$
Exact Mass: 379.09
Molecular Weight: 380.28

2-Bromo-6-(1-methylhydrazinyl)pyridine (1.60 g, 7.98 mmol) and tert-butyl 2-methyl-4-oxopiperidine-1-carboxylate (enantiomer B) (1.70 g, 7.98 mmol) were heated in EtOH (10 mL) at reflux for 16 h and then the mixture was concentrated to provide a white foam. This foam was combined with para-toluenesulphonic acid (3.18 g, 16.7 mmol) and heated to 160° C. for 10 minutes. The mixture was allowed to cool and isopropanol (20 mL), water (8 mL), potassium carbonate (5.00 g, 36.2 mmol), and di-tert-butyl dicarbonate (2.55 g, 11.7 mmol) were added. After stirring for 16 h, the mixture was partitioned between methylene chloride and water, and the organic layer was removed, dried, and concentrated. The residue was purified by column chromatography eluting with ethyl acetate/hexanes (1:4) to provide the title compound (360 mg, 11%) as a white solid: ESI MS m/z 380 [M+H]$^+$.

c) tert-Butyl 2-(4-(benzyloxy)-2-oxopyridin-1(2H)-yl)-7,9-dimethyl-5,7,8,9-tetrahydro-6H-pyrido[3',4':4,5]pyrrolo[2,3-b]pyridine-6-carboxylate (Enantiomer B)

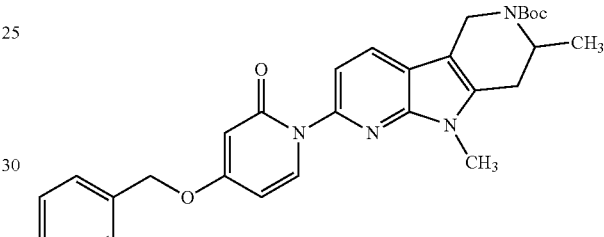

Chemical Formula: C$_{29}$H$_{32}$N$_4$O$_4$
Exact Mass: 500.24
Molecular Weight: 500.59 tert-Butyl 2-bromo-7,9-dimethyl-5,7,8,9-tetrahydro-6H-pyrido[3',4':4,5]pyrrolo[2,3-b]pyridine-6-carboxylate (enantiomer B) (100 mg, 0.263 mmol) and 4-(benzyloxy)pyridin-2(1H)-one (53 mg, 0.263 mmol) were reacted following the procedure for Example 2 (step e) to provide the title compound (39 mg, 30%) as a yellow oil: ESI MS m/z 501 [M+H]$^+$.

d) (−)-4-(Benzyloxy)-1-(7,9-dimethyl-5,7,8,9-tetrahydro-6H-pyrido[3',4':4,5]pyrrolo[2,3-b]pyridin-2-yl)pyridin-2(1H)-one hydrochloride

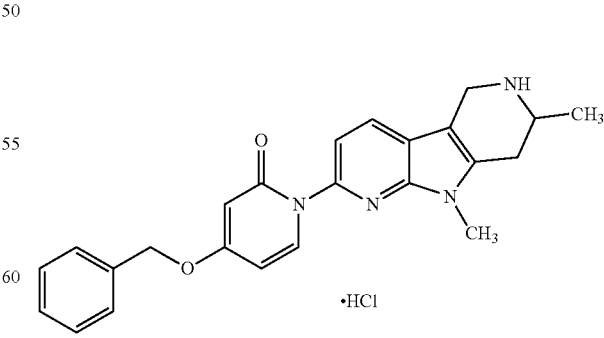

Chemical Formula: C$_{24}$H$_{25}$ClN$_4$O$_2$
Exact Mass: 436.17
Molecular Weight: 436.93 tert-Butyl 2-(4-(benzyloxy)-2-oxopyridin-1(2H)-yl)-7,9-dimethyl-5,7,8,9-tetrahydro-6H-pyrido[3',4':4,5]pyrrolo[2,3-b]pyridine-6-carboxylate (enantiomer B) (36 mg, 0.072 mmol) was reacted following the procedure for Example 2 (steps f and g) to provide the title compound (10 mg, 32%) as a yellow solid: $[\alpha]^{23}_D$ –10° (c 1.00, Methanol); $^1$H NMR (500 MHz, DMSO-$d_6$) δ 9.48-9.46 (m, 1H), 9.26-9.24 (m, 1H), 8.07 (d, J=8.2 Hz, 1H), 7.82 (d, J=7.7 Hz, 1H), 7.49-7.45 (m, 2H), 7.45-7.41 (m, 2H), 7.39-7.35 (m, 2H), 6.18-6.16 (dd, J=7.7, 2.5 Hz, 1H), 5.99 (d, J=2.7 Hz, 1H), 5.17 (s, 2H), 4.46 (d, J=15.0 Hz, 1H), 4.35-4.31 (m, 1H), 3.78-3.68 (m, 4H), 3.30-3.26 (dd, J=17.3, 4.6 Hz, 1H), 2.91-2.85 (dd, J=17.1, 9.8 Hz, 1H), 1.48 (d, J=6.5 Hz, 3H); ESI MS m/z 401 [M+H]$^+$; HPLC (Method B) 98.8% (AUC), $t_R$=14.1 min.

Example 18

Preparation of 4-(Benzyloxy)-1-(1,2,3,4-tetrahydropyrazino[1,2-a]benzimidazol-8-yl)pyridin-2(1H)-one hydrochloride a) 2-(2-Amino-4-bromophenylamino)ethanol

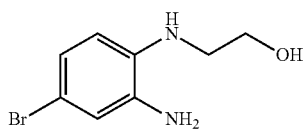

Chemical Formula: C$_8$H$_{11}$BrN$_2$O
Exact Mass: 230.01
Molecular Weight: 231.09

2-(4-Bromo-2-nitrophenylamino)ethanol (3.20 g, 12.3 mmol) was stirred in EtOH (100 mL) and water (50 mL), and iron powder (3.45 g, 61.6 mmol) and ammonium chloride (731 mg, 13.5 mmol) were added. The mixture was heated at 85° C. for 2 h, then filtered through a pad of celite and rinsed with EtOH (500 mL). The filtrate was concentrated and purified by column chromatography eluting with methylene chloride and a 9:1 methanol/ammonium hydroxide mixture; gradient 100% methylene chloride to 85% methylene chloride, to provide the title compound (2.58 g, 91%) as a yellow oil: ESI MS m/z 231 [M+H]$^+$.

b) tert-Butyl 2-(5-bromo-2-(2-hydroxyethylamino)phenylamino)-2-oxoethylcarbamate

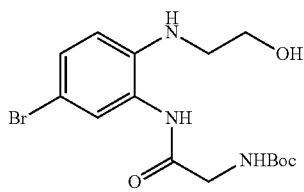

Chemical Formula: C$_{15}$H$_{22}$BrN$_3$O$_4$
Exact Mass: 387.08
Molecular Weight: 388.26

2-(2-Amino-4-bromophenylamino)ethanol (700 mg, 3.03 mmol), N-Boc-glycine (639 mg, 3.65 mmol), HATU (1.39 g, 3.66 mmol) and i-Pr$_2$NEt (785 mg, 1.0 mL, 6.09 mmol) were stirred in methylene chloride (20 mL) for 20 min. The mixture was purified by column chromatography eluting with methylene chloride and a 9:1 methanol/ammonium hydroxide mixture; gradient 100% methylene chloride to 85% methylene chloride, to provide the title compound (1.26 g, quant) as a yellow oil: ESI MS m/z 388 [M+H]$^+$.

c) 2-(2-(Aminomethyl)-5-bromo-1H-benzo[d]imidazol-1-yl)ethanol

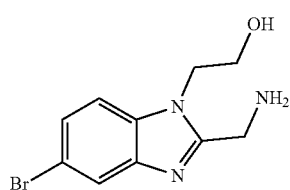

Chemical Formula: C$_{10}$H$_{12}$BrN$_3$O
Exact Mass: 269.02
Molecular Weight: 270.13 tert-Butyl 2-(5-bromo-2-(2-hydroxyethylamino)phenylamino)-2-oxoethylcarbamate (1.26 g, 3.24 mmol) was stirred in 6 N hydrochloric acid (15 mL) at 120° C. for 2 h and then concentrated. The residue was made basic with methanol/ammonium hydroxide (9:1), re-concentrated and purified by column chromatography eluting with methylene chloride and a 9:1 methanol/ammonium hydroxide mixture; gradient 100% methylene chloride to 85% methylene chloride, to provide the title compound (579 mg, 60%) as a yellow oil: ESI MS m/z 270 [M+H]$^+$.

d) tert-Butyl ((5-bromo-1-(2-hydroxyethyl)-1H-benzo[d]imidazol-2-yl)methyl)carbamate

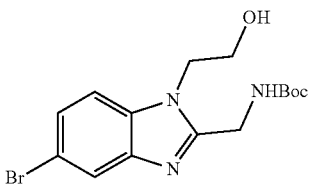

Chemical Formula: C$_{15}$H$_{20}$BrN$_3$O$_3$
Exact Mass: 369.07
Molecular Weight: 370.24

2-(2-(Aminomethyl)-5-bromo-1H-benzo[d]imidazol-1-yl)ethanol (529 mg, 1.96 mmol) was stirred in water/i-PrOH (12 mL/8 mL), and K$_2$CO$_3$ (306 mg, 2.22 mmol) and di-tert-butyl dicarbonate (484 mg, 2.22 mmol) were added. The mixture was stirred for 16 h, diluted with water, and the solid e) 2-(5-Bromo-2-((tert-butoxycarbonylamino)methyl)-1H-benzo[d]imidazol-1-yl)ethyl methanesulfonate

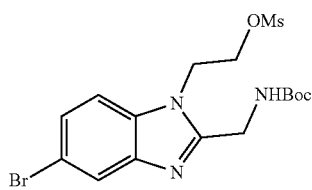

Chemical Formula: C$_{16}$H$_{22}$BrN$_3$O$_5$S
Exact Mass: 447.05
Molecular Weight: 448.33 tert-Butyl ((5-bromo-1-(2-hydroxyethyl)-1H-benzo[d]imidazol-2-yl)methyl)carbamate (648 mg, 1.75 mmol) was stirred in methylene chloride (25 mL), and triethylamine (530 mg, 0.74 mL, 5.3 mmol) and methanesulfonyl chloride (400 mg, 0.27 mL, 3.5 mmol) were added. The mixture was stirred for 2 h and then washed with water, dried over sodium sulfate and concentrated to provide the title compound (833 mg, quant) as a yellow solid: ESI MS m/z 448 [M+H]$^+$.

f) tert-Butyl 8-bromo-3,4-dihydropyrazino[1,2-a]benzimidazole-2(1H)-carboxylate

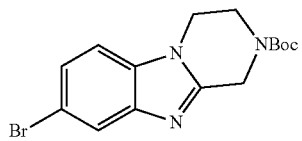

Chemical Formula: C$_{15}$H$_{18}$BrN$_3$O$_2$
Exact Mass: 351.06
Molecular Weight: 352.23

2-(5-Bromo-2-((tert-butoxycarbonylamino)methyl)-1H-benzo[d]imidazol-1-yl)ethyl methanesulfonate (883 mg, crude, 1.76 mmol estimated) was stirred in TFA (10 mL) for 1 h and then concentrated. Water/i-PrOH (32 mL/8 mL) and K$_2$CO$_3$ (2.31 g, 16.7 mmol) were added, and the mixture was heated at 105° C. for 2 h and then cooled to room temperature. Di-tert-butyl dicarbonate (812 mg, 3.73 mmol) was added, and the reaction mixture was stirred for 48 h and then diluted with water. The solid was filtered off and dried under vacuum to provide the title compound (549 mg, 89%) as a brown solid: ESI MS m/z 352 [M+H]$^+$.

g) tert-Butyl 8-(4-(benzyloxy)-2-oxopyridin-1(2H)-yl)-3,4-dihydropyrazino[1,2-a]benzimidazole-2(1H)-carboxylate

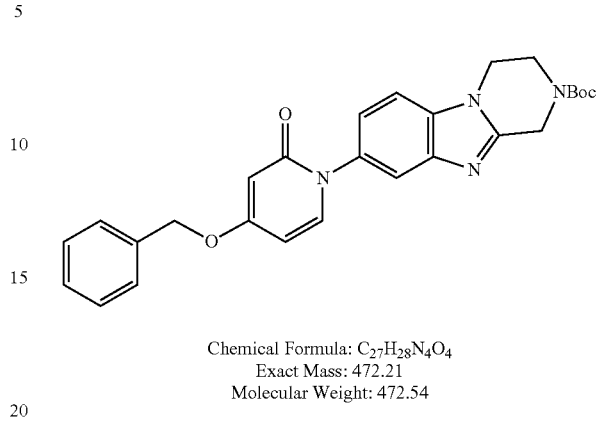

Chemical Formula: C$_{27}$H$_{28}$N$_4$O$_4$
Exact Mass: 472.21
Molecular Weight: 472.54 tert-Butyl 8-bromo-3,4-dihydropyrazino[1,2-a]benzimidazole-2(1H)-carboxylate (188 mg, 0.534 mmol), 4-(benzyloxy)pyridin-2(1H)-one (118 mg, 0.589 mmol), CuI (203 mg, 1.07 mmol), trans-N,N'dimethylcyclohexane-1,2-diamine (76 mg, 0.54 mmol) and Cs$_2$CO$_3$ (192 mg, 0.591 mmol) in 1,4-dioxane (15 mL) were sparged with a nitrogen stream for 45 min and then stirred at 110° C. for 16 h. The mixture was diluted with 90:9:1 CH$_2$Cl$_2$/MeOH/NH$_4$OH (50 mL) and washed with brine (3×50 mL). The resulting solution was dried over Na$_2$SO$_4$ and concentrated under reduced pressure to give a crude residue. The residue was purified by column chromatography eluting with methylene chloride and a 9:1 methanol/ammonium hydroxide mixture; gradient 100% methylene chloride to 85% methylene chloride, to provide the title compound (131 mg, 28%) as a brown solid: ESI MS m/z 473 [M+H]$^+$.

h) 4-(Benzyloxy)-1-(1,2,3,4-tetrahydropyrazino[1,2-a]benzimidazol-8-yl)pyridin-2(1H)-one hydrochloride

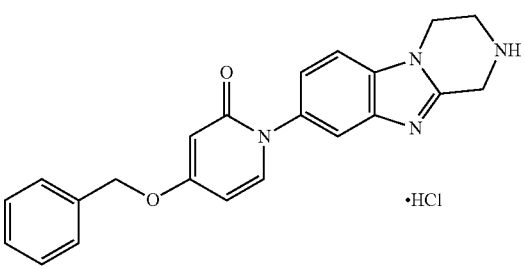

Chemical Formula: C$_{22}$H$_{21}$ClN$_4$O$_2$
Exact Mass: 408.14
Molecular Weight: 408.88 tert-Butyl 8-(4-(benzyloxy)-2-oxopyridin-1(2H)-yl)-3,4-dihydropyrazino[1,2-a]benzimidazole-2(1H)-carboxylate (130 mg, 0.275 mmol) was stirred in TFA (2 mL) for 1 h and diluted with CH$_2$Cl$_2$ (50 mL) and Na$_2$CO$_3$ solution (50 mL). The organic layer was removed, dried and concentrated, and the residue was purified by column chromatography eluting with methylene chloride and a 9:1 methanol/ammonium hydroxide mixture; gradient 100% methylene chloride to 85% methylene chloride, to provide the free base (46 mg). This was dissolved in MeOH (2 mL), treated with 2 N HCl in Et$_2$O (61 µL, 0.12 mmol) and concentrated to provide the title compound (47 mg, 42%) as a yellow solid: $^1$H NMR (500 MHz, DMSO-d$_6$) δ 10.04 (s, 2H), 7.68 (d, J=8.5 Hz, 1H), 7.60 (d, J=1.8 Hz, 1H), 7.59 (d, J=7.6 Hz, 1H), 7.49-7.45 (m, 2H), 7.45-7.40 (m, 2H), 7.39-7.35 (m, 1H), 7.27-7.25 (dd, J=8.5, 1.9 Hz, 1H), 6.12-6.02 (dd, J=7.6, 2.7 Hz, 1H), 5.98 (d, J=2.7 Hz, 1H), 5.15 (s, 2H), 4.65 (s, 2H), 4.44 (t, J=5.7 Hz, 2H), 3.77 (t, J=5.7 Hz, 2H); ESI MS m/z 373 [M+H]$^+$; HPLC (Method B)>99% (AUC), t$_R$=11.9 min.

Example 19

Preparation of 4-((5-Fluoropyridin-2-yl)methoxy)-1-(1,2,3,4-tetrahydropyrazino[1,2-a]benzimidazol-8-yl)pyridin-2(1H)-one hydrochloride a) tert-Butyl 8-(4-((5-fluoropyridin-2-yl)methoxy)-2-oxopyridin-1(2H)-yl)-3,4-dihydropyrazino[1,2-a]benzimidazole-2(1H)-carboxylate

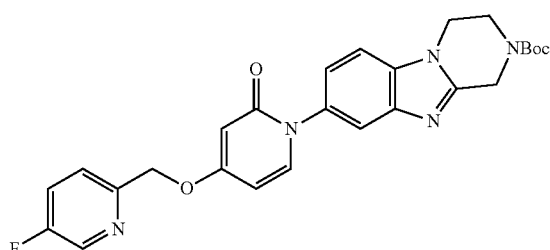

Chemical Formula: C$_{26}$H$_{26}$FN$_5$O$_4$
Exact Mass: 491.20
Molecular Weight: 491.51 tert-Butyl 8-bromo-3,4-dihydropyrazino[1,2-a]benzimidazole-2(1H)-carboxylate (150 mg, 0.426 mmol) and 4-((5-fluoropyridin-2-yl)methoxy)pyridin-2(1H)-one (103 mg, 0.468 mmol) were reacted according to Example 18 (step g) to provide the title compound (103 mg, 47%) as a white solid: ESI MS m/z 492 [M+H]$^+$.

b) 4-((5-Fluoropyridin-2-yl)methoxy)-1-(1,2,3,4-tetrahydropyrazino[1,2-a]benzimidazol-8-yl)pyridin-2(1H)-one hydrochloride

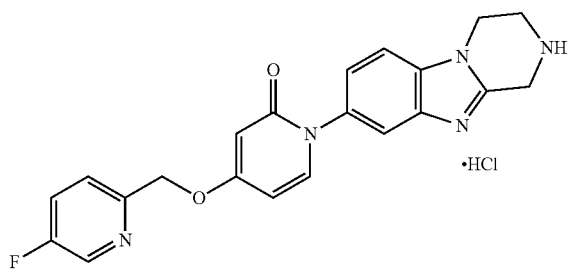

Chemical Formula: C$_{21}$H$_{19}$ClFN$_5$O$_2$
Exact Mass: 427.12
Molecular Weight: 427.86 tert-Butyl 8-(4-((5-fluoropyridin-2-yl)methoxy)-2-oxopyridin-1(2H)-yl)-3,4-dihydropyrazino[1,2-a]benzimidazole-2(1H)-carboxylate (103 mg, 0.210 mmol) was deprotected and converted to the hydrochloride salt according to Example 18 (step h) to provide the title compound (41 mg, 46%) as a white solid: mp 245-255° C.; $^1$H NMR (500 MHz, DMSO-d$_6$) δ 9.95 (s, 2H), 8.62 (d, J=2.9 Hz, 1H), 7.84-7.80 (overlapping ddd, J=8.7, 3.0 Hz, 1H), 7.68-7.64 (m, 2H), 7.61-7.59 (m, 2H), 7.26-7.24 (dd, J=8.5, 1.9 Hz, 1H), 6.14-6.12 (dd, J=7.7, 2.7 Hz, 1H), 5.98 (d, J=2.7 Hz, 1H), 5.24 (s, 2H), 4.64 (s, 2H), 4.43 (t, J=5.7 Hz, 2H), 3.77 (t, J=5.7 Hz, 2H); ESI MS m/z 392 [M+H]$^+$; HPLC (Method B)>99% (AUC), t$_R$=10.5 min.

Example 20

Preparation of 1-(1,2,3,4-Tetrahydropyrazino[1,2-a]benzimidazol-8-yl)-4-(4-(trifluoromethyl)phenyl)pyridin-2(1H)-one hydrochloride a) tert-Butyl 8-(2-oxo-4-(4-(trifluoromethyl)phenyl)pyridin-1(2H)-yl)-3,4-dihydropyrazino[1,2-a]benzimidazole-2(1H)-carboxylate

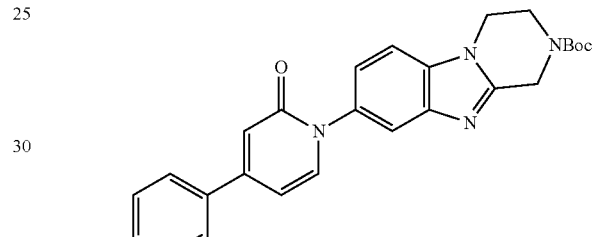

Chemical Formula: C$_{27}$H$_{25}$F$_3$N$_4$O$_3$
Exact Mass: 510.19
Molecular Weight: 510.51 tert-Butyl 8-bromo-3,4-dihydropyrazino[1,2-a]benzimidazole-2(1H)-carboxylate (150 mg, 0.426 mmol) and 4-(4-(trifluoromethyl)phenyl)pyridin-2(1H)-one (112 mg, 0.469 mmol) were reacted according to Example 18 (step g) to provide the title compound (15 mg, 7%) as a white solid: ESI MS m/z 511 [M+H]$^+$.

b) 1-(1,2,3,4-Tetrahydropyrazino[1,2-a]benzimidazol-8-yl)-4-[4-(trifluoromethyl)phenyl]pyridin-2(1H)-one

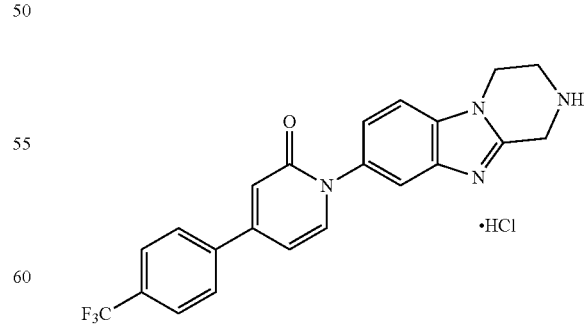

Chemical Formula: C$_{22}$H$_{18}$ClF$_3$N$_4$O
Exact Mass: 446.11
Molecular Weight: 446.85 tert-Butyl 8-(2-oxo-4-(4-(trifluoromethyl)phenyl)pyridin-1(2H)-yl)-3,4-dihydropyrazino[1,2-a]benzimidazole-2(1H)-carboxylate (15 mg, 0.023 mmol) was deprotected and converted to the hydrochloride according to Example 18 (step h) to provide the title compound (5 mg, 38%) as an orange solid: $^1$H NMR (500 MHz, DMSO-$d_6$) δ 9.71 (s, 2H), 8.01 (d, J=8.3 Hz, 2H), 7.88 (d, J=8.3 Hz, 2H), 7.82 (d, J=7.8 Hz, 1H), 7.75 (m, 2H), 7.37 (d, J=8.4 Hz, 1H), 6.88 (s, 1H), 7.73 (d, J=7.5 Hz, 1H), 4.67 (s, 2H), 4.47-4.41 (m, 2H), 3.83-3.77 (m, 2H); ESI MS m/z 411 [M+H]$^+$; HPLC (Method B) 91.3% (AUC), $t_R$=12.8 min.

Example 21

Preparation of 4-(Benzyloxy)-1-(2-(propan-2-yl)-1,2,3,4-tetrahydropyrazino[1,2-a]benzimidazol-8-yl)pyridin-2(1H)-one hydrochloride

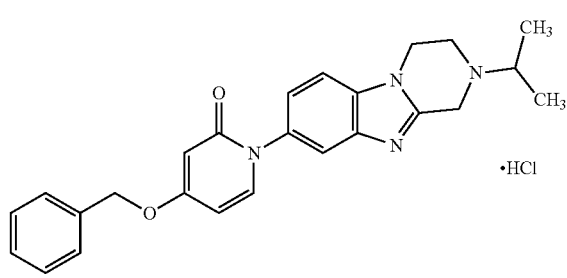

Chemical Formula: C$_{25}$H$_{27}$ClN$_4$O$_2$
Exact Mass: 450.18
Molecular Weight: 450.96

4-(Benzyloxy)-1-(1,2,3,4-tetrahydropyrazino[1,2-a]benzimidazol-8-yl)pyridin-2(1H)-one hydrochloride (16 mg, 0.043 mmol) was dissolved in a mixture of methylene chloride (2.8 mL) and AcOH (0.3 mL), and acetone (283 mg, 4.87 mmol) and 2-picoline borane (14 mg, 0.13 mmol) were added. The mixture was stirred at 50° C. for 48 h and then concentrated. The residue was purified by column chromatography eluting with methylene chloride and a 9:1 methanol/ammonium hydroxide mixture; gradient 100% methylene chloride to 85% methylene chloride, to provide the free base (18 mg). This was dissolved in MeOH (2 mL) and treated with 2 N HCl in Et$_2$O (21 μL, 0.043 mmol) and concentrated to provide the title compound as a yellow solid: $^1$H NMR (500 MHz, DMSO-$d_6$) δ 11.43 (s, 1H), 7.71 (d, J=8.6 Hz, 1H), 7.63 (s, 1H), 7.59 (d, J=7.6 Hz, 1H), 7.49-7.45 (m, 2H), 7.45-7.41 (m, 2H), 7.39-7.35 (m, 1H), 7.28 (d, J=8.6 Hz, 1H), 6.12-6.10 (dd, J=7.6, 2.7 Hz, 1H), 5.98 (d, J=2.7 Hz, 1H), 5.15 (s, 2H), 4.79-4.62 (br m, 3H), 4.49-4.35 (br m, 2H), 4.12-3.96 (br m, 2H), 1.41 (s, 3H), 1.39 (s, 3H); ESI MS m/z 415 [M+H]$^+$; HPLC (Method B) 97.7% (AUC), $t_R$=12.2 min.

Example 22

Preparation 4-(Benzyloxy)-1-(1,2,3,4-tetrahydropyrido[4',3':4,5]imidazo[1,2-a]pyridin-7-yl)pyridin-2(1H)-one hydrochloride a) tert-Butyl 7-bromo-3,4-dihydropyrido[4',3':4,5]imidazo[1,2-a]pyridine-2(1H)-carboxylate

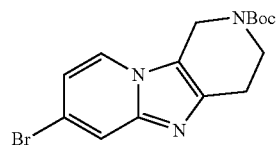

Chemical Formula: C$_{15}$H$_{18}$BrN$_3$O$_2$
Exact Mass: 351.06
Molecular Weight: 352.23

2-Amino-4-bromopyridine (786 mg, 4.55 mmol) and tert-butyl 3-bromo-4-oxopiperidine-1-carboxylate (1.39 g, 5.00 mmol) were combined in toluene (20 mL) and heated at 105° C. for 16 h. The mixture was concentrated and purified by flash column chromatography (40 g ISCO column eluting with methylene chloride and a methanol/ammonia mixture (10:1); gradient 100% methylene chloride to 80% methylene chloride over 30 min at 40 mL/min) to provide the title compound (512 mg, 32%) as a white solid: $^1$H NMR (500 MHz, CDCl$_3$) δ 7.93 (s, 1H), 7.46 (d, J=9.1 Hz, 1H), 7.22 (d, J=9.1 Hz, 1H), 4.69 (br s, 2H), 3.85 (br s, 2H), 2.93 (br s, 2H), 1.51 (s, 9H).

b) tert-Butyl 7-(4-(benzyloxy)-2-oxopyridin-1(2H)-yl)-3,4-dihydropyrido[4',3':4,5]imidazo[1,2-a]pyridine-2(1H)-carboxylate

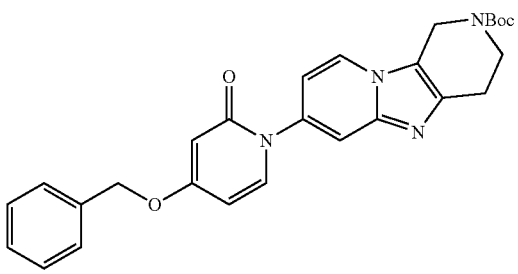

Chemical Formula: C$_{27}$H$_{28}$N$_4$O$_4$
Exact Mass: 472.21
Molecular Weight: 472.54 tert-Butyl 7-bromo-3,4-dihydropyrido[4',3':4,5]imidazo[1,2-a]pyridine-2(1H)-carboxylate (591 mg, 1.68 mmol) and 4-(benzyloxy)pyridin-2(1H)-one (338 mg, 1.68 mmol) were reacted according to Example 18 (step g) to provide the title compound (482 mg, 61%) as a brown solid: ESI MS m/z 473 [M+H]$^+$.

c) 4-(Benzyloxy)-1-(1,2,3,4-tetrahydropyrido[4',3':4,5]imidazo[1,2-a]pyridin-7-yl)pyridin-2(1H)-one hydrochloride

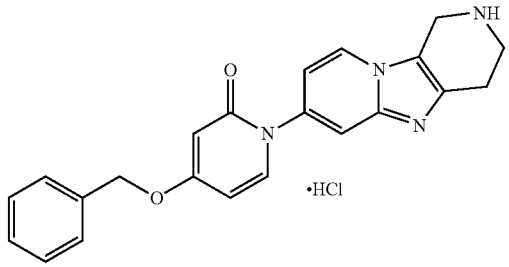

Chemical Formula: C$_{22}$H$_{21}$ClN$_4$O$_2$
Exact Mass: 408.14
Molecular Weight: 408.88 tert-Butyl 7-(4-(benzyloxy)-2-oxopyridin-1(2H)-yl)-3,4-dihydropyrido[4',3':4,5]imidazo[1,2-a]pyridine-2(1H)-carboxylate (482 mg, 1.02 mmol) was deprotected and converted to the hydrochloride according to Example 18 (step h) to provide the title compound (340 mg, 82%) as a white solid: mp 280° C. dec; $^1$H NMR (500 MHz, DMSO-d$_6$) δ 9.93 (s, 2H), 8.54 (d, J=7.2 Hz, 1H), 7.77 (s, 1H), 7.69 (d, J=7.6 Hz, 1H), 7.47-7.34 (m, 5H), 7.23 (d, J=6.6 Hz, 1H), 6.19 (dd, J=7.6, 2.5 Hz, 1H), 6.02 (d, J=2.5 Hz, 1H), 5.16 (s, 2H), 4.57 (s, 2H), 3.51 (s, 2H), 3.08 (t, J=5.4 Hz, 2H); ESI MS m/z 373 [M+H]; HPLC (Method B) 98.8% (AUC), t$_R$=10.6 min.

Example 23

Preparation of 4-((5-Fluoropyridin-2-yl)methoxy)-1-(1,2,3,4-tetrahydropyrido[4',3':4,5]imidazo[1,2-a]pyridin-7-yl)pyridin-2(1H)-one hydrochloride a) tert-Butyl 7-(4-((5-fluoropyridin-2-yl)methoxy)-2-oxopyridin-1(2H)-yl)-3,4-dihydropyrido[4',3':4,5]imidazo[1,2-a]pyridine-2 (1H)-carboxylate

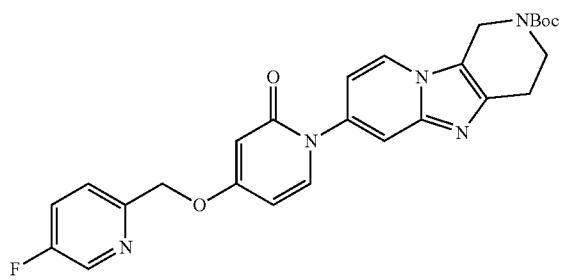

Chemical Formula: C$_{26}$H$_{26}$FN$_5$O$_4$
Exact Mass: 491.20
Molecular Weight: 491.51 tert-Butyl 7-bromo-3,4-dihydropyrido[4',3':4,5]imidazo[1,2-c]pyridine-2(1H)-carboxylate (160 mg, 0.454 mmol) and 4-((5-fluoropyridin-2-yl)methoxy)pyridin-2(1H)-one (100 mg, 0.454 mmol) were reacted according to Example 18 (step g) to provide the title compound (67 mg, 30%) as a brown solid: ESI MS m/z 492 [M+H]$^+$.

b) 4-((5-fluoropyridin-2-yl)methoxy)-1-(1,2,3,4-tetrahydropyrido[4',3':4,5]imidazo[1,2-a]pyridin-7-yl)pyridin-2(1H)-one hydrochloride

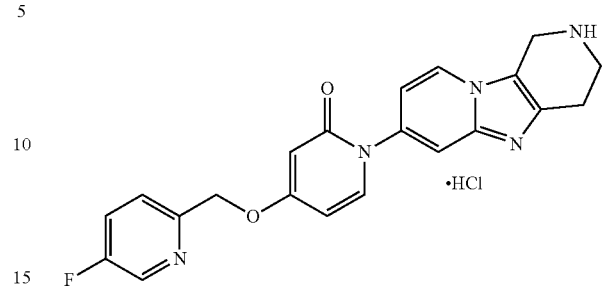

Chemical Formula: C$_{21}$H$_{19}$ClFN$_5$O$_2$
Exact Mass: 427.12
Molecular Weight: 427.86 tert-Butyl 7-(4-((5-fluoropyridin-2-yl)methoxy)-2-oxopyridin-1(2H)-yl)-3,4-dihydropyrido[4',3':4,5]imidazo[1,2-a]pyridine-2(1H)-carboxylate (67 mg, 0.14 mmol) was deprotected and converted to the hydrochloride salt according to Example 18 (step h) to provide title compound (25 mg, 42%) as a white solid: $^1$H NMR (500 MHz, DMSO-d$_6$) δ 9.71 (s, 2H), 8.62 (d, J=2.9 Hz, 1H), 8.47 (d, J=7.2 Hz, 1H), 7.85-7.80 (overlapping ddd, J=8.7, 2.3 Hz, 1H), 7.71-7.68 (m, 2H), 7.76-7.64 (dd, J=8.6, 4.4 Hz, 1H), 7.14-7.12 (dd, J=7.1, 1.4 Hz, 1H), 6.21-6.19 (dd, J=7.7, 2.7 Hz, 1H), 6.02 (d, J=2.7 Hz, 1H), 5.23 (s, 2H), 4.56 (s, 2H), 3.53-3.48 (m, 2H), 3.06 (t, J=5.8 Hz, 2H); ESI MS m/z 392 [M+H]$^+$; HPLC (Method B)>99% (AUC), t$_R$=9.2 min.

Example 24

Preparation of 1-(1,2,3,4-Tetrahydropyrido[4',3':4,5]imidazo[1,2-a]pyridin-7-yl)-4-(6-(trifluoromethyl)pyridin-3-yl)pyridin-2(1H)-one hydrochloride a) tert-Butyl 7-(2-oxo-4-(6-(trifluoromethyl)pyridin-3-yl)pyridin-1(2H)-yl)-3,4-dihydropyrido[4',3':4,5]imidazo[1,2-a]pyridine-2 (1H)-carboxylate

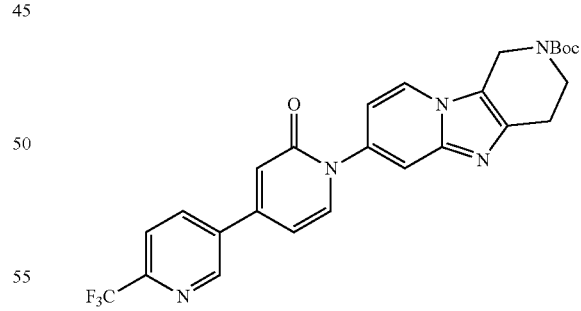

Chemical Formula: C$_{26}$H$_{24}$F$_3$N$_5$O$_3$
Exact Mass: 511.18
Molecular Weight: 511.50 tert-Butyl 7-bromo-3,4-dihydropyrido[4',3':4,5]imidazo[1,2-a]pyridine-2(1H)-carboxylate (212 mg, 0.602 mmol) and 4-(6-(trifluoromethyl)pyridin-3-yl)pyridin-2(1H)-one (145 mg, 0.604 mmol) were reacted according to Example 18 (step g) to provide the title compound (170 mg, 55%) as a white solid: ESI MS m/z 512 [M+H]$^+$.

b) 1-(1,2,3,4-Tetrahydropyrido[4',3':4,5]imidazo[1,2-a]pyridin-7-yl)-4-(6-(trifluoromethyl)pyridin-3-yl)pyridin-2(1H)-one hydrochloride

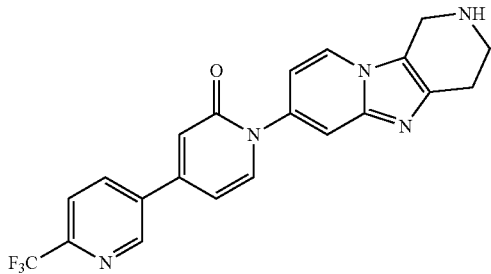

Chemical Formula: C<sub>21</sub>H<sub>17</sub>ClF<sub>3</sub>N<sub>5</sub>O
Exact Mass: 447.11
Molecular Weight: 447.84 tert-Butyl 7-(2-oxo-4-(6-(trifluoromethyl)pyridin-3-yl)pyridin-1(2H)-yl)-3,4-dihydropyrido[4',3':4,5]imidazo[1,2-a]pyridine-2(1H)-carboxylate (170 mg, 0.332 mmol) was deprotected and converted to the hydrochloride salt according to Example 18 (step h) to provide the title compound (65 mg, 41%) as a yellow solid: mp 265° C. dec; $^1$H NMR (500 MHz, CD$_3$OD) δ 9.10 (d, J=1.9 Hz, 1H), 8.48 (d, J=7.2 Hz, 1H), 8.42-8.40 (dd, J=8.1, 2.1 Hz, 1H), 7.98 (d, J=8.1 Hz, 1H), 7.91 (d, J=7.2 Hz, 1H), 7.84 (d, J=1.6 Hz, 1H), 7.32-7.30 (dd, J=7.2, 2.0 Hz, 1H), 7.04 (d, J=1.7 Hz, 1H), 6.94-6.92 (dd, J=7.2, 2.0 Hz, 1H), 4.71 (s, 2H), 3.72 (t, J=6.1 Hz, 2H), 3.24 (t, J=6.1 Hz, 2H); ESI MS m/z 412 [M+H]; HPLC (Method B) 95.7% (AUC), t$_R$=10.5 min.

Example 25

Preparation of 1-(1,2,3,4-Tetrahydropyrido[4',3':4,5]imidazo[1,2-a]pyridin-7-yl)-4-((6-(trifluoromethyl)pyridin-3-yl)methoxy)pyridin-2(1H)-one hydrochloride a) tert-Butyl 7-(2-oxo-4-((6-(trifluoromethyl)pyridin-3-yl)methoxy)pyridin-1(2H)-yl)-3,4-dihydropyrido[4',3':4,5]imidazo[1,2-a]pyridine-2(1H)-carboxylate

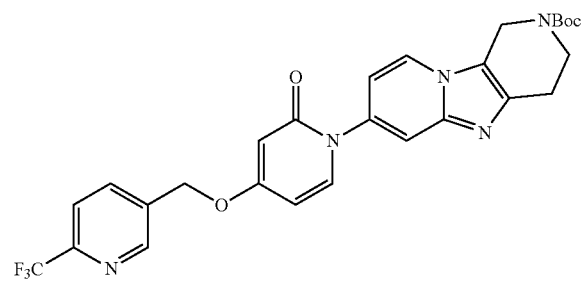

Chemical Formula: C<sub>27</sub>H<sub>26</sub>F<sub>3</sub>N<sub>5</sub>O<sub>4</sub>
Exact Mass: 541.19
Molecular Weight: 541.52 tert-Butyl 7-bromo-3,4-dihydropyrido[4',3':4,5]imidazo[1,2-a]pyridine-2(1H)-carboxylate (175 mg, 0.498 mmol) and 4-((6-(trifluoromethyl)pyridin-3-yl)methoxy)pyridin-2(1H)-one (134 mg, 0.498 mmol) were reacted according to Example 18 (step g) to provide the title compound (104 mg, 44%) as a yellow solid: ESI MS m/z 542 [M+H]<sup>+</sup>.

b) 1-(1,2,3,4-Tetrahydropyrido[4',3':4,5]imidazo[1,2-a]pyridin-7-yl)-4-((6-(trifluoromethyl)pyridin-3-yl)methoxy)pyridin-2(1H)-one hydrochloride

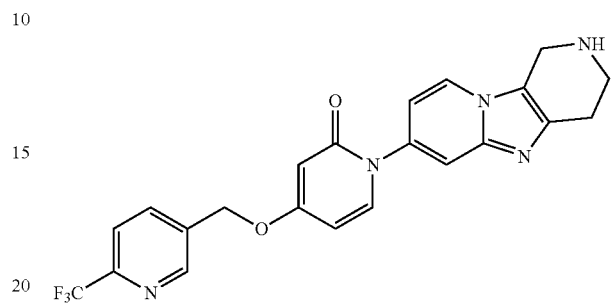

Chemical Formula: C<sub>22</sub>H<sub>19</sub>ClF<sub>3</sub>N<sub>5</sub>O<sub>2</sub>
Exact Mass: 477.12
Molecular Weight: 477.87 tert-Butyl 7-(2-oxo-4-((6-(trifluoromethyl)pyridin-3-yl)methoxy)pyridin-1(2H)-yl)-3,4-dihydropyrido[4',3':4,5]imidazo[1,2-a]pyridine-2(1H)-carboxylate (104 mg, 0.192 mmol) was deprotected and converted to the hydrochloride salt according to Example 18 (step h) to provide title compound (60 mg, 65%) as a white solid: mp 265° C. dec; $^1$H NMR (500 MHz, CD$_3$OD) δ 8.85 (s, 1H), 8.37 (d, J=7.2 Hz, 1H), 8.16 (d, J=8.2 Hz, 1H), 7.88 (d, J=7.8 Hz, 1H), 7.69 (s, 1H), 7.67 (d, J=7.5 Hz, 1H), 7.17-7.16 (dd, J=7.3, 1.9 Hz, 1H), 6.38-6.36 (dd, J=7.7, 2.7 Hz, 1H), 6.17 (d, J=2.5 Hz, 1H), 5.35 (s, 2H), 4.67 (s, 2H), 3.70 (t, J=6.1 Hz, 2H), 3.26 (t, J=6.1 Hz, 2H); ESI MS m/z 442 [M+H]<sup>+</sup>; HPLC (Method B) 98.0% (AUC), t$_R$=10.6 min.

Example 26

Preparation of 1-(1,2,3,4-Tetrahydropyrido[4',3':4,5]imidazo[1,2-a]pyridin-7-yl)-4-(4-(trifluoromethyl)phenyl)pyridin-2(1H)-one hydrochloride a) tert-Butyl 7-(2-oxo-4-(4-(trifluoromethyl)phenyl)pyridin-1(2H)-yl)-3,4-dihydropyrido[4',3':4,5]imidazo[1,2-a]pyridine-2 (1H)-carboxylate

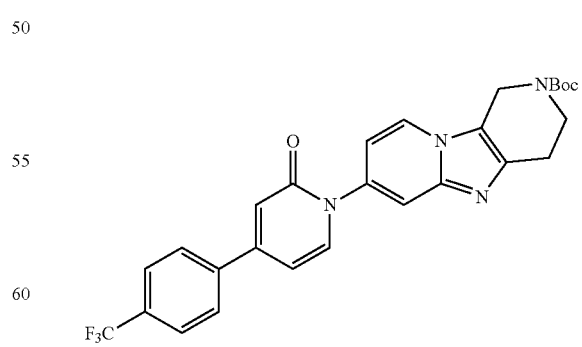

Chemical Formula: C<sub>27</sub>H<sub>25</sub>F<sub>3</sub>N<sub>4</sub>O<sub>3</sub>
Exact Mass: 510.19
Molecular Weight: 510.51 tert-Butyl 7-bromo-3,4-dihydropyrido[4',3':4,5]imidazo[1,2-a]pyridine-2(1H)-carboxylate (150 mg, 0.426 mmol) and 4-(4-(trifluoromethyl)phenyl)pyridin-2(1H)-one (103 mg, 0.426 mmol) were reacted according to Example 18 (step g) to provide the title compound (138 mg, 64%) as a yellow solid: ESI MS m/z 511 [M+H]+.

b) 1-(1,2,3,4-Tetrahydropyrido[4',3':4,5]imidazo[1,2-a]pyridin-7-yl)-4-(4-(trifluoromethyl)phenyl)pyridin-2(1H)-one hydrochloride

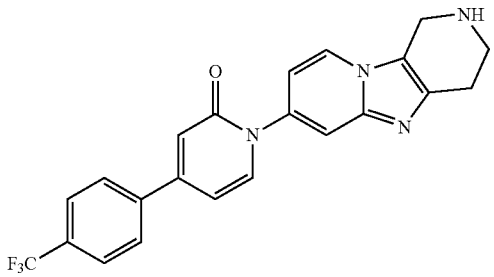

Chemical Formula: C22H18ClF3N4O
Exact Mass: 446.11
Molecular Weight: 446.85 tert-Butyl 7-(2-oxo-4-(4-(trifluoromethyl)phenyl)pyridin-1(2H)-yl)-3,4-dihydropyrido[4',3':4,5]imidazo[1,2-a]pyridine-2(1H)-carboxylate (138 mg, 0.270 mmol) was deprotected and converted to the hydrochloride salt according to Example 18 (step h) to provide the title compound (58 mg, 48%) as a yellow solid: 1H NMR (500 MHz, CD3OD) δ 8.74 (d, J=6.9 Hz, 1H), 7.95 (d, J=8.2 Hz, 2H), 7.91 (d, J=1.6 Hz, 1H), 7.87 (d, J=7.2 Hz, 1H), 7.84 (d, J=8.2 Hz, 2H), 7.40-7.38 (dd, J=7.2, 1.8 Hz, 1H), 6.97 (d, J=1.6 Hz, 1H), 6.92-6.90 (dd, J=7.2, 1.8 Hz, 1H), 4.72 (s, 2H), 3.73 (t, J=6.2 Hz, 2H), 3.28 (t, J=6.2 Hz, 2H); ESI MS m/z 411 [M+H]+; HPLC (Method B) 98.2% (AUC), $t_R$=11.5 min.

Example 27

Preparation of 4-(Benzyloxy)-1-(2-(propan-2-yl)-1,2,3,4-tetrahydropyrido[4',3':4,5]imidazo[1,2-a]pyridin-7-yl)pyridin-2(1H)-one hydrochloride

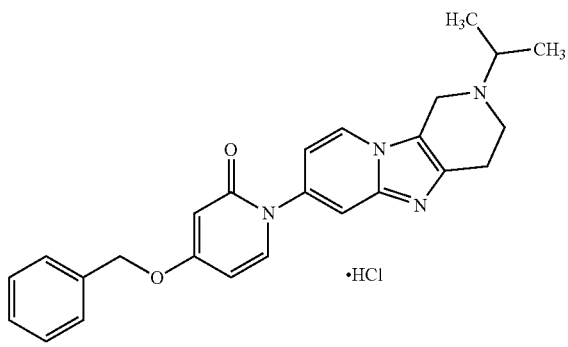

Chemical Formula: C25H27ClN4O2
Exact Mass: 450.18
Molecular Weight: 450.96

4-(Benzyloxy)-1-(1,2,3,4-tetrahydropyrido[4',3':4,5]imidazo[1,2-a]pyridin-7-yl)pyridin-2(1H)-one hydrochloride (126 mg, 0.308 mmol) was dissolved in a mixture of methylene chloride (2.8 mL) and AcOH (0.3 mL), and acetone (3 mL) and 2-picoline borane (100 mg, 0.934 mmol) were added. The mixture was stirred at 50° C. for 48 h and then concentrated. The residue was purified by column chromatography eluting with methylene chloride and a 9:1 methanol/ammonium hydroxide mixture; gradient 100% methylene chloride to 85% methylene chloride, to provide the free base (74 mg). This was dissolved in MeOH (2 mL) and treated with 2 N HCl in Et2O (89 µL, 0.018 mmol) and concentrated to provide the title compound (96 mg, 69%) as a yellow solid: 275-283° C.; 1H NMR (500 MHz, DMSO-d6) δ 11.25 (s, 1H), 8.16 (d, J=7.2 Hz, 1H), 7.77 (s, 1H), 7.70 (d, J=7.7 Hz, 1H), 7.48-7.39 (m, 5H), 7.24 (d, J=6.8 Hz, 1H), 6.20-6.18 (dd, J=7.8, 2.6 Hz, 1H), 6.02 (d, J=2.8 Hz, 1H), 5.17 (s, 2H), 4.78 (d, J=14.0 Hz, 1H), 4.60-4.52 (m, 1H), 3.83-3.61 (m, 2H), 3.51-3.41 (m, 1H), 3.37-3.26 (m, 1H), 3.07 (d, J=15.0 Hz, 1H), 1.44 (d, J=6.3 Hz, 3H), 1.41 (d, J=6.3 Hz, 3H); ESI MS m/z 415 [M+H]+; HPLC (Method B) 99.0% (AUC), $t_R$=10.9 min.

Example 28

Preparation of 4-(Benzyloxy)-1-(9-methyl-5-oxo-5,7,8,9-tetrahydro-6H-pyrido[3',4':4,5]pyrrolo[2,3-b]pyridin-2-yl)pyridin-2(1H)-one a) tert-Butyl 2-bromo-9-methyl-5-oxo-5,7,8,9-tetrahydro-6H-pyrido[3',4':4,5]pyrrolo[2,3-b]pyridine-6-carboxylate

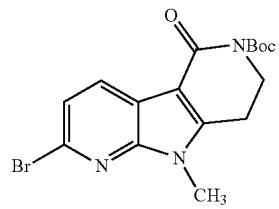

Chemical Formula: C16H18BrN3O3
Exact Mass: 379.05
Molecular Weight: 380.24

To a stirred solution of tert-butyl 2-bromo-9-methyl-5,7,8,9-tetrahydro-6H-pyrido[3',4':4,5]pyrrolo[2,3-b]pyridine-6-carboxylate (732 mg, 2.0 mmol) in CH2Cl2 (20 mL) at room temperature was added 18-crown-6 (53 mg, 0.20 mmol) followed by addition of KMnO4 (474 mg, 3.0 mmol) in small portions over 20 min. The reaction mixture was stirred at room temperature for 17 h, quenched with saturated sodium metabisulfite solution (20 ml) and extracted with CH2Cl2 (3×20 mL). The combined extracts were dried over sodium sulfate, filtered, and concentrated. Flash chromatography (40 g ISCO column, 100:0 to 65:35 hexanes/EtOAc gradient) gave the title compound (134 mg, 18%) as an orange solid: 1H NMR (500 MHz, DMSO-d6) δ 8.30 (d, J=8.1 Hz, 1H), 7.36

(d, J=8.1 Hz, 1H), 4.22 (t, J=6.4 Hz, 2H), 3.80 (s, 3H), 3.05 (t, J=6.4 Hz, 2H), 1.59 (s, 9H); ESI MS m/z 380 [M+H]$^+$.

b) tert-Butyl 2-(4-(benzyloxy)-2-oxopyridin-1(2H)-yl)-9-methyl-5-oxo-5,7,8,9-tetrahydro-6H-pyrido[3',4':4,5]pyrrolo[2,3-b]pyridine-6-carboxylate

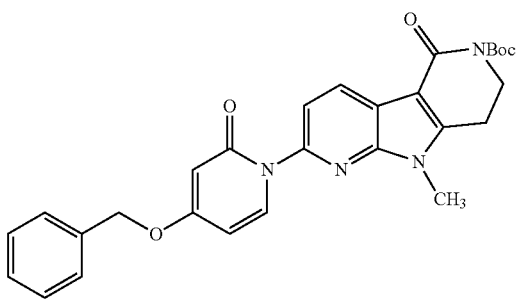

Chemical Formula: C$_{28}$H$_{28}$N$_4$O$_5$
Exact Mass: 500.21
Molecular Weight: 500.55 tert-Butyl 2-bromo-9-methyl-5-oxo-5,7,8,9-tetrahydro-6H-pyrido[3',4':4,5]pyrrolo[2,3-b]pyridine-6-carboxylate (140 mg, 0.37 mmol), 4-benzyloxy pyridinone (74 mg, 0.37 mmol), and Cs$_2$CO$_3$ (132 mg, 0.41 mmol) were suspended in toluene (2 mL), and the air was removed under vacuum at −70° C. for 15 min. The system was flushed with N$_2$, and trans-N,N'-dimethylcyclohexane-1,2-diamine (0.12 mL, 0.74 mmol) and copper iodide (140 mg, 0.74 mmol) were added to the suspension. The evacuation/N$_2$ flushing process was repeated twice more, and the reaction mixture was heated at 105° C. for 18 h under N$_2$. The mixture was cooled, diluted with 95:5 CH$_2$Cl$_2$/MeOH (12 mL), and washed with 2:1 brine/NH$_4$OH (3×12 mL). The resulting organic solution was dried over Na$_2$SO$_4$, filtered, and concentrated to dryness under reduced pressure. The crude title compound was used in the next step without purification.

c) 4-(Benzyloxy)-1-(9-methyl-5-oxo-5,7,8,9-tetrahydro-6H-pyrido[3',4':4,5]pyrrolo[2,3-b]pyridin-2-yl)pyridin-2(1H)-one

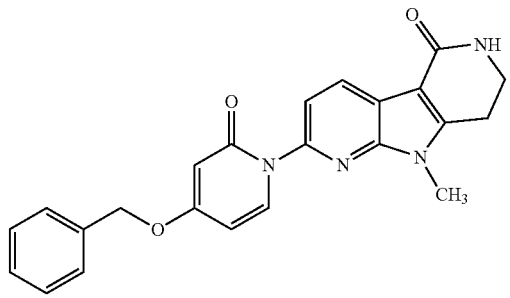

Chemical Formula: C$_{23}$H$_{20}$N$_4$O$_3$
Exact Mass: 400.15
Molecular Weight: 400.43

To a stirred solution of tert-butyl 2-(4-(benzyloxy)-2-oxopyridin-1(2H)-yl)-9-methyl-5-oxo-5,7,8,9-tetrahydro-6H-pyrido[3',4':4,5]pyrrolo[2,3-b]pyridine-6-carboxylate (crude, ca. 0.37 mmol) in CH$_2$Cl$_2$ (4 mL) at 0° C. was added TFA (0.4 mL). The resulting solution was stirred at 0° C. for 1 h, quenched with saturated NaHCO$_3$ solution (10 mL), and extracted with CH$_2$Cl$_2$ (3×10 mL). The combined organic extractions were dried over Na$_2$SO$_4$ and concentrated under reduced pressure to dryness. Preparative thin layer chromatography (200:10:1 CH$_2$Cl$_2$/MeOH/NH$_4$OH) provided the title compound (49 mg, 33% over 2 steps) as an off-white solid: $^1$H NMR (300 MHz, DMSO-d$_6$) δ 8.28 (d, J=8.2 Hz, 1H), 7.84 (d, J=7.7 Hz, 1H), 7.49-7.34 (m, 6H), 7.25 (br t, 1H), 6.18 (dd, J=7.8, 2.7 Hz, 1H), 6.01 (d, J=2.7 Hz, 1H), 5.17 (s, 2H), 3.76 (s, 3H), 3.53 (td, J=6.9, 2.4 Hz, 2H), 3.09 (t, J=6.9 Hz, 2H); ESI MS m/z 401 [M+H]$^+$; HPLC (Method B) 99.0% (AUC), t$_R$=14.6 min.

Example 29

Preparation of 1-(6-Acetyl-7,9-dimethyl-5,7,8,9-tetrahydro-6H-pyrido[3',4':4,5]pyrrolo[2,3-b]pyridin-2-yl)-4-(benzyloxy)pyridin-2(1H)-one
(Enantiomer A)

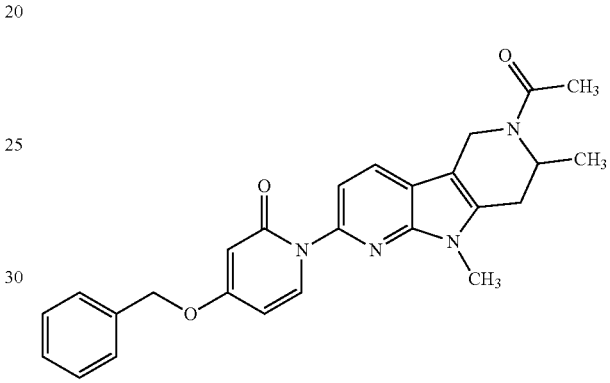

Chemical Formula: C$_{26}$H$_{26}$N$_4$O$_3$
Exact Mass: 442.20
Molecular Weight: 442.51

(−)-4-(Benzyloxy)-1-(7,9-dimethyl-5,7,8,9-tetrahydro-6H-pyrido[3',4':4,5]pyrrolo[2,3-b]pyridin-2-yl)pyridin-2(1H)-one hydrochloride (67 mg, 0.15 mmol) was reacted following the procedure for Example 11 to provide the title compound (31 mg, 42%) as an off-white solid and a mixture of rotomers: $^1$H NMR (500 MHz, CDCl$_3$) δ 7.87 (m, 1H), 7.68 (m, 1H), 7.42-7.26 (m, 6H), 6.06 (m, 2H), 5.54 (m, 1H), 5.06 (s, 2H), 4.78 (m, 0.5H), 4.63 (m, 1H), 4.10 (m, 0.5H), 3.72 (s, 3H), 3.19 (m, 1H), 2.71 (m, 0.5H), 2.65 (m, 0.5H), 2.24 (m, 3H), 1.20 (m, 1.5H), 1.21 (m, 1.5H); ESI MS m/z 443 [M+H]$^+$; HPLC (Method B) 98.2% (AUC), t$_R$=17.5 min.

Example 30

Binding Assay for Human Melanin-Concentrating Hormone (MCH-1) Receptor

Evaluation of the affinity of compounds for the human MCH-1 receptor was accomplished using 4-(3,4,5-trititriumbenzyloxy)-1-(1-(2-(pyrrolidin-1-yl)ethyl)-1H-indazol-5-yl)pyridin-2(1H)-one and membranes prepared from stable CHO-K1 cells expressing the human MCH-1 receptor obtained from Euroscreen (Batch 1138). Cell membrane homogenates (8.92 μg protein) were incubated for 60 min at 25° C. with 1.4 μM of the [$^3$H]-labeled compound in the absence or presence of the test compound in 50 mM Tris-HCl buffer, pH 7.4. Nonspecific binding was determined in the presence of 50 μM 1-(5-(4-cyanophenyl)bicyclo[3.1.0]hexan-2-yl)-3-(4-fluoro-3-(trifluoromethyl)phenyl)-1-(3-(4- methylpiperazin-1-yl)propyl)urea. Following incubation, the samples were filtered rapidly under vacuum through Skatron 11731 filters, pre-soaked in 0.5% polyethylenimine, and washed with ice-cold 50 mM Tris-HCl buffer, pH 7.4, (wash setting 9,9,0) using a Skatron cell harvester. The filters were counted for radioactivity in a liquid scintillation counter (Tri-Carb 2100TR, Packard) using a scintillation cocktail (Ultima Gold MV, Perkin Elmer).

The results are expressed as a percent inhibition of the control radioligand specific binding. The $IC_{50}$ value (concentration causing a half-maximal inhibition of control specific binding) and Hill coefficient ($n_H$) were determined by non-linear regression analysis of the competition curve using Hill equation curve fitting. The inhibition constant ($K_i$) was calculated from the Cheng Prusoff equation: ($K_i=IC_{50}/(1+(L/K_D))$), where L=concentration of radioligand in the assay, and $K_D$=affinity of the radioligand for the receptor.

By methods as described above, the compounds listed in Table 1 were synthesized and tested for biological activity.

TABLE 1

Compounds Tested for Biological Activity

| Ex, No. | Structure | MCH₁ $K_i$ (nM) | Mass Spec | ¹H NMR Data |
|---|---|---|---|---|
| 2 | 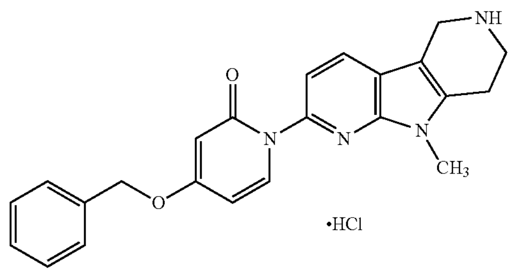 [SMILES: Cn1c2c(c3ccc(-n4ccc(OCc5ccccc5)cc4=O)nc31)CNCC2 ; Cl] | 7.1 | 387 | ¹H NMR (500 MHz, DMSO-d₆) δ 8.53 (br s, 1H), 8.02 (d, J = 8.0 Hz, 1H), 7.81 (d, J = 7.5 Hz, 1H), 7.49-7.41 (m, 4H), 7.40-7.32 (m, 2H), 6.17 (dd, J = 7.5, 2.5 Hz, 1H), 5.99 (d, J = 2.5 Hz, 1H), 5.17 (s, 2H), 4.27 (s, 2H), 3.70 (s, 3H), 3.46 (t, J = 5.5 Hz, 2H), 3.05 (t, J = 5.5 Hz, 2H) |
| 3 | 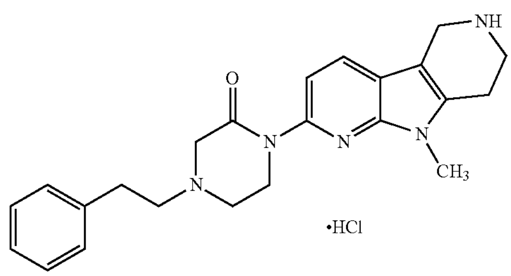 [SMILES: Cn1c2c(c3ccc(N4CCN(CCc5ccccc5)CC4=O)nc31)CNCC2 ; Cl] | 47 | 390 | ¹H NMR (500 MHz, DMSO-d₆) δ 9.47 (br s, 2H), 8.01 (d, J = 8.4 Hz, 1H), 7.53 (d, J = 8.4 Hz, 1H), 7.40-7.25 (m, 5H), 4.38-4.24 (m, 3H), 4.24-4.07 (m, 2H), 4.06-3.89 (m, 2H), 3.70 (s, 3H), 3.60-3.38 (m, 6H), 3.19-3.07 (m, 4H) |
| 4 | 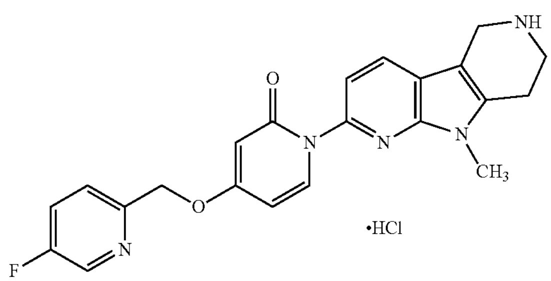 [SMILES: Cn1c2c(c3ccc(-n4ccc(OCc5ccc(F)cn5)cc4=O)nc31)CNCC2 ; Cl] | 15 | 406 | ¹H NMR (500 MHz, DMSO-d₆) δ 8.62 (d, J = 3.0 Hz, 1H), 7.97 (s, J = 8.0 Hz, 1H), 7.87-7.78 (m, 2H), 7.69-7.64 (m, 1H), 7.30 (s, J = 8.0 Hz, 1H), 7.09 (br s, 1H), 6.19 (dd, J = 7.5, 2.5 Hz, 1H), 5.99 (d, J = 3.0 Hz, 1H), 5.23 (s, 2H), 4.12 (s, 2H), 3.68 (s, 3H), 3.36-3.21 (m, 2H, overlap with H₂O), 2.94 (t, J = 5.5 Hz, 2H) |
| 5 | 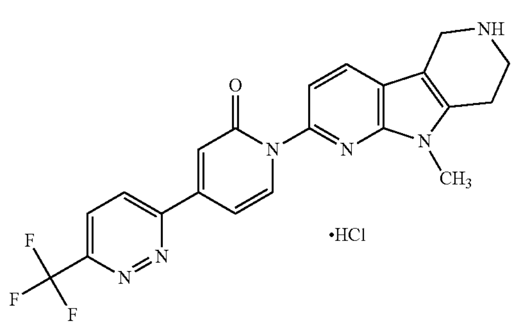 [SMILES: Cn1c2c(c3ccc(-n4ccc(-c5ccc(C(F)(F)F)nn5)cc4=O)nc31)CNCC2 ; Cl] | 105 | 427 | ¹H NMR (500 MHz, DMSO-d₆) δ 8.72 (d, J = 9.0 Hz, 1H), 8.47 (d, J = 8.5 Hz, 1H), 8.14 (d, J = 7.5 Hz, 1H), 8.06 (d, J = 8.5 Hz, 1H), 7.45 (d, J = 8.0 Hz, 1H), 7.41 (d, J = 2.0 Hz, 1H), 7.23 (dd, J = 7.5, 2.0 Hz, 1H), 4.19 (s, 2H), 3.72 (s, 3H), 3.38 (t, J = 5.5 Hz, 2H), 3.00 (t, J = 5.5 Hz, 2H) |

TABLE 1-continued

Compounds Tested for Biological Activity

| Ex, No. | Structure | MCH$_1$ K$_i$ (nM) | Mass Spec | $^1$H NMR Data |
|---|---|---|---|---|
| 6 | 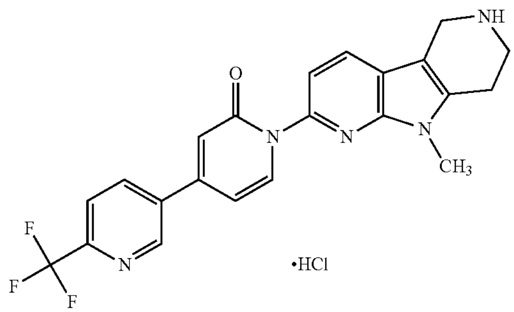 [SMILES: Cn1c2c(c3ccc(-n4ccc(-c5ccc(C(F)(F)F)nc5)cc4=O)nc31)CNCC2 ; Cl] | 15 | 426 | $^1$H NMR (500 MHz, DMSO-d$_6$) δ 9.38 (s, 2H), 9.21 (d, J = 2.5 Hz, 1H), 8.51 (dd, J = 8.0, 2.0 Hz, 1H), 8.12 (d, J = 8.5 Hz, 1H), 8.09-8.04 (m, 2H), 7.46 (d, J = 8.0 Hz, 1H), 7.04 (d, J = 2.0 Hz, 1H), 6.86 (dd, J = 7.5, 2.0 Hz, 1H), 4.37 (s, 2H), 3.74 (s, 3H), 3.55 (t, J = 6.5 Hz, 2H), 3.15 (t, J = 6.0 Hz, 2H) |
| 7 | 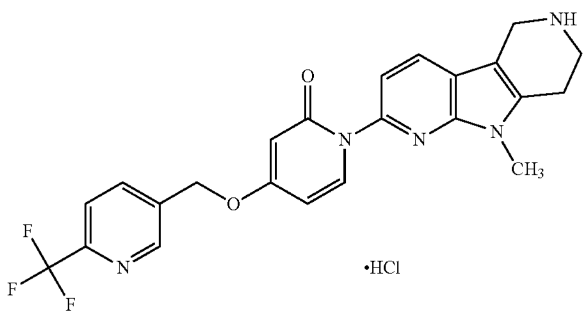 [SMILES: Cn1c2c(c3ccc(-n4ccc(OCc5ccc(C(F)(F)F)nc5)cc4=O)nc31)CNCC2 ; Cl] | 71 | 456 | $^1$H NMR (500 MHz, DMSO-d$_6$) δ 8.89 (d, J = 1.0 Hz, 1H), 8.19 (d, J = 8.0, 1.5 Hz, 1H), 8.17-7.80 (m, 4H), 7.33 (d, J = 8.5 Hz, 1H), 6.21 (dd, J = 7.5, 2.5 Hz, 1H), 6.04 (d, J = 2.5 Hz, 1H), 5.36 (s, 2H), 4.22 (s, 2H), 3.69 (s, 3H), 3.41 (t, J = 6.0 Hz, 2H), 3.01 (t, J = 5.5 Hz, 2H) |
| 8 | 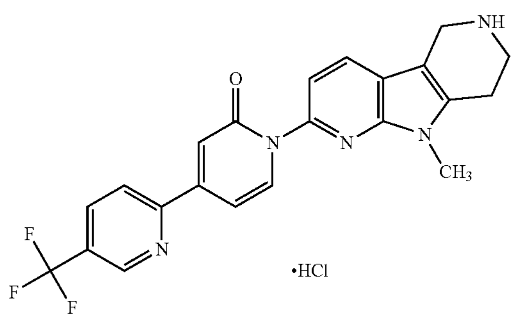 [SMILES: Cn1c2c(c3ccc(-n4ccc(-c5ccc(C(F)(F)F)cn5)cc4=O)nc31)CNCC2 ; Cl] | 33 | 426 | $^1$H NMR (500 MHz, DMSO-d$_6$) δ 9.30 (br s, 1H), 9.15 (t, J = 1.0 Hz, 1H), 8.42-8.34 (m, 2H), 8.13 (d, J = 8.0 Hz, 1H), 8.08 (d, J = 7.0 Hz, 1H), 7.49 (d, J = 8.5 Hz, 1H), 7.32 (d, J = 2.0 Hz, 1H), 7.13 (dd, J = 7.0, 2.0 Hz, 1H), 4.39 (s, 2H), 3.74 (s, 3H), 3.60-3.51 (m, 2H), 3.15 (t, J = 6.0 Hz, 2H) |
| 9 | 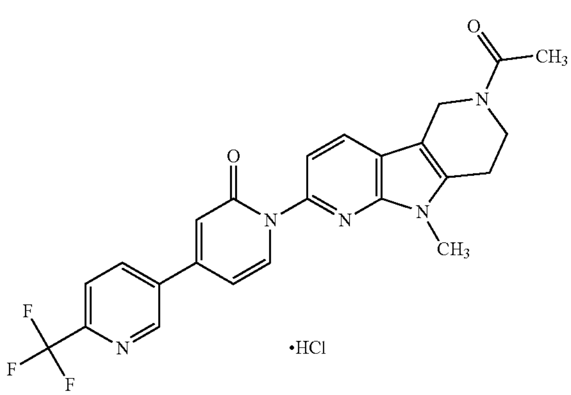 [SMILES: CC(=O)N1CCc2c(c3ccc(-n4ccc(-c5ccc(C(F)(F)F)nc5)cc4=O)nc3n2C)C1 ; Cl] | 78 | 468 | $^1$H NMR (500 MHz, DMSO-d$_6$) δ 9.20 (d, J = 2.0 Hz, 1H), 8.50 (dd, J = 8.0, 2.0 Hz, 1H), 8.11-8.04 (m, 3H), 7.44-7.37 (m, 1H), 7.03 (d, J = 1.5 Hz, 1H), 6.86-6.83 (m, 1H), 4.73-4.68 (m, 2H), 3.90-3.83 (m, 2H), 3.71-3.69 (m, 3H), 3.01-2.86 (m, 2H), 2.16-2.12 (m, 3H) |

TABLE 1-continued

Compounds Tested for Biological Activity

| Ex. No. | Structure | MCH₁ $K_i$ (nM) | Mass Spec | $^1$H NMR Data |
|---|---|---|---|---|
| 10 | 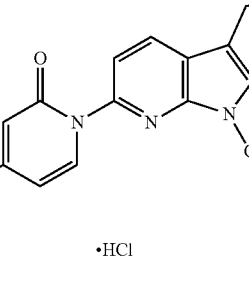 | 4.7 | 425 | $^1$H NMR (500 MHz, DMSO-d₆) δ 8.06-8.00 (m, 4H), 7.88 (d, J = 8.0 Hz, 2H), 7.42 (d, J = 3.0 Hz, 1H), 6.90 (d, J = 2.0 Hz, 1H), 6.78 (dd, J = 7.0, 2.0 Hz, 1H), 4.19 (s, 2H), 3.71 (s, 3H), 3.37 (t, J = 5.5 Hz, 2H), 2.99 (t, J = 5.5 Hz, 2H) |
| 11 | 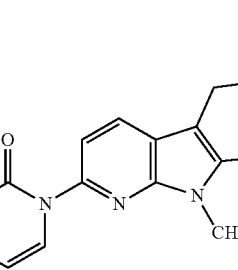 | 71 | 429 | $^1$H NMR (500 MHz, DMSO-d⁶) δ 8.01 (t, J = 8.5 Hz, 1H), 7.80 (dd, J = 7.5, 2.5 Hz, 1H), 7.49-7.36 (m, 5H), 7.33-7.26 (m, 1H), 6.15 (dd, J = 8.0, 3.0 Hz, 1H), 5.98 (d, J = 2.5 Hz, 1H), 5.16 (s, 2H), 4.71-4.66 (m, 2H), 3.90-3.81 (m, 2H), 3.67 (m, 3H), 3.00-2.86 (m, 2H), 2.16-2.10 (m, 3H) |
| 12 | 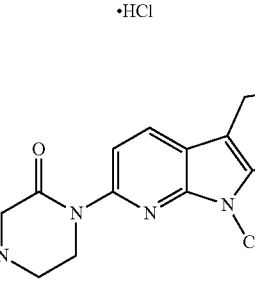 | 58 | 422 | $^1$H NMR (300 MHz, CD₃OD) δ 7.94 (d, J = 8.3 Hz, 1H), 7.43 (d, J = 8.3 Hz, 1H), 7.33-7.28 (m, 2H), 7.06-7.00 (m, 2H), 4.53 (d, J = 14.7 Hz, 1H), 4.42 (d, J = 14.7 Hz, 1H), 4.11-4.07 (m, 2H), 3.84-3.79 (m, 1H), 3.75 (s, 3H), 3.69-3.51 (m, 2H), 3.37-3.33 (m, 1H), 3.26-3.07 (m, 2H), 2.98-2.89 (m, 5H), 1.59 (d, J = 6.5 Hz, 3H) |
| 13 | 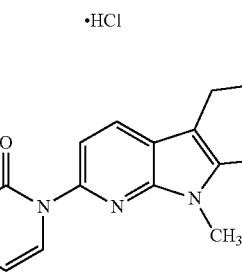 | 9.3 | 401 | $^1$H NMR (300 MHz, DMSO-d₆) δ 9.73-9.51 (m, 1H), 9.51-9.00 (m, 1H), 8.08 (d, J = 8.3 Hz, 1H), 7.81 (d, J = 7.7 Hz, 1H), 7.49-7.34 (m, 6H), 6.19-6.15 (dd, J = 7.8, 2.7 Hz, 1H), 5.99 (d, J = 2.7 Hz, 1H), 5.17 (s, 2H), 4.48-4.42 (m, 1H), 4.40-4.17 (m, 1H), 3.70-3.58 (m, 4H), 3.30-3.22 (m, 1H), 2.93-2.84 (m, 1H), 1.48 (d, J = 6.5 Hz, 3H) |
| 14 | 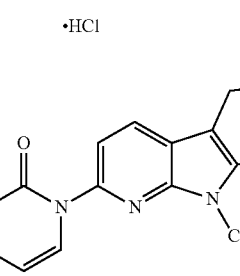 | 25 | 420 | $^1$H NMR (300 MHz, DMSO-d₆) δ 9.77-9.62 (m, 1H), 9.50-9.20 (m, 1H), 8.63 (d, J = 2.9 Hz, 1H), 8.08-8.06 (d, J = 8.2 Hz, 1H), 7.88-7.79 (m, 2H), 7.68-7.63 (dd, J = 8.7, 4.5 Hz, 1H), 7.35 (d, J = 8.3 Hz, 1H), 6.26-6.25 (dd, J = 7.8, 2.8 Hz, 1H), 6.00 (d, J = 9.1 Hz, 1H), 5.23 (s, 2H), 4.47-4.28 (m, 1H), 4.35-4.28 (m, 1H), 3.75-3.65 (m, 4H), 3.24-3.13 (dd, J = 7.3, 4.5 Hz, 1H), 2.93-2.84 (m, 1H), 1.48 (d, J = 7.5 Hz, 3H) |

TABLE 1-continued

Compounds Tested for Biological Activity

| Ex, No. | Structure | MCH₁ $K_i$ (nM) | Mass Spec | ¹H NMR Data |
|---|---|---|---|---|
| 15 | (2,4-dichlorobenzyloxy pyridinone linked to methyl-tetrahydropyrrolopyridine) ·HCl | 17 | 455 | ¹H NMR (500 MHz, DMSO-d₆) δ 9.22 (s, 2H), 8.07 (d, J = 8.5 Hz, 1H), 7.84 (d, J = 7.5 Hz, 1H), 7.74 (d, J = 2.5 Hz, 1H), 7.67 (d, J = 8.0 Hz, 1H), 7.53 (dd, J = 8.0, 2.0 Hz, 1H), 7.38 (d, J = 8.0 Hz, 1H), 6.19 (dd, J = 8.0, 2.5 Hz, 1H), 6.04 (d, J = 3.0 Hz, 1H), 5.21 (s, 2H), 4.38 (br s, 2H), 3.72 (s, 3H), 3.58-3.53 (m, 2H), 3.16-3.11 (m, 2H) |
| 16 | (2,4-difluorobenzyloxy pyridinone linked to methyl-tetrahydropyrrolopyridine) ·HCl | 8.3 | 423 | ¹H NMR (500 MHz, DMSO-d₆) δ 9.28 (s, 2H), 8.07 (d, J = 8.5 Hz, 1H), 7.82 (d, J = 7.5 Hz, 1H), 7.67 (dd, J = 15.0, 8.5 Hz, 1H), 7.40-7.33 (m, 2H), 7.18 (ddd, J = 8.5, 8.5, 2.0 Hz, 1H), 6.15 (dd, J = 8.5, 2.5 Hz, 1H), 6.07 (d, J = 2.5 Hz, 1H), 5.17 (s, 2H), 4.37 (br s, 2H), 3.72 (s, 3H), 3.58-3.52 (m, 2H), 3.14 (t, J = 5.5 Hz, 2H) |
| 17 | (benzyloxy pyridinone linked to dimethyl-tetrahydropyrrolopyridine) ·HCl (−)-Enantiomer | 9.1 | 401 | ¹H NMR (500 MHz, DMSO-d₆) δ 9.48-9.46 (m, 1H), 9.26-9.24 (m, 1H), 8.07 (d, J = 8.2 Hz, 1H), 7.82 (d, J = 7.7 Hz, 1H), 7.49-7.45 (m, 2H), 7.45-7.41 (m, 2H), 7.39-7.35 (m, 2H), 6.18-6.16 (dd, J = 7.7, 2.5 Hz, 1H), 5.99 (d, J = 2.7 Hz, 1H), 5.17 (s, 2H), 4.46 (d, J = 15.0 Hz, 1H), 4.35-4.31 (m, 1H), 3.78-3.68 (m, 4H), 3.30-3.26 (dd, J = 17.3, 4.6 Hz, 1H), 2.91-2.85 (dd, J = 17.1, 9.8 Hz, 1H), 1.48 (d, J = 6.5 Hz, 3H) |
| 18 | (benzyloxy pyridinone linked to tetrahydrobenzimidazopyrazine) ·HCl | 62 | 373 | ¹H NMR (500 MHz, DMSO-d₆) δ 10.04 (s, 2H), 7.68 (d, J = 8.5 Hz, 1H), 7.60 (d, J = 1.8 Hz, 1H), 7.59 (d, J = 7.6 Hz, 1H), 7.49-7.45 (m, 2H), 7.45-7.40 (m, 2H), 7.39-7.35 (m, 1H), 7.27-7.25 (dd, J = 8.5, 1.9 Hz, 1H), 6.12-6.02 (dd, J = 7.6, 2.7 Hz, 1H), 5.98 (d, J = 2.7 Hz, 1H), 5.15 (s, 2H), 4.65 (s, 2H), 4.44 (t, J = 5.7 Hz, 2H), 3.77 (t, J = 5.7 Hz, 2H) |
| 19 | (5-fluoropyridinylmethoxy pyridinone linked to tetrahydrobenzimidazopyrazine) ·HCl | 72% @ 1 uM | 392 | ¹H NMR (500 MHz, DMSO-d₆) δ 9.95 (s, 2H), 8.62 (d, J = 2.9 Hz, 1H), 7.84-7.80 (overlapping ddd, J = 8.7, 3.0 Hz, 1H), 7.68-7.64 (m, 2H), 7.61-7.59 (m, 2H), 7.26-7.24 (dd, J = 8.5, 1.9 Hz, 1H), 6.14-6.12 (dd, J = 7.7, 2.7 Hz, 1H), 5.98 (d, J = 2.7 Hz, 1H), 5.24 (s, 2H), 4.64 (s, 2H), 4.43 (t, J = 5.7 Hz, 2H), 3.77 (t, J = 5.7 Hz, 2H) |

TABLE 1-continued

Compounds Tested for Biological Activity

| Ex. No. | Structure | MCH$_1$ K$_i$ (nM) | Mass Spec | $^1$H NMR Data |
|---|---|---|---|---|
| 20 | (structure) ·HCl | 61% @ 1 uM | 411 | $^1$H NMR (500 MHz, DMSO-d$_6$) δ 9.71 (s, 2H), 8.01 (d, J = 8.3 Hz, 2H), 7.88 (d, J = 8.3 Hz, 2H), 7.82 (d, J = 7.8 Hz, 1H), 7.75 (m, 2H), 7.37 (d, J = 8.4 Hz, 1H), 6.88 (s, 1H), 7.73 (d, J = 7.5 Hz, 1H), 4.67 (s, 2H), 4.47-4.41 (m, 2H), 3.83-3.77 (m, 2H) |
| 21 | (structure) ·HCl | 94 | 415 | $^1$H NMR (500 MHz, DMSO-d$_6$) δ 11.43 (s, 1H), 7.71 (d, J = 8.6 Hz, 1H), 7.63 (s, 1H), 7.59 (d, J = 7.6 Hz, 1H), 7.49-7.45 (m, 2H), 7.45-7.41 (m, 2H), 7.39-7.35 (m, 1H), 7.28 (d, J = 8.6 Hz, 1H), 6.12-6.10 (dd, J = 7.6, 2.7 Hz, 1H), 5.98 (d, J = 2.7 Hz, 1H), 5.15 (s, 2H), 4.79-4.62 (br m, 3H), 4.49-4.35 (br m, 2H), 4.12-3.96 (br m, 2H), 1.41 (s, 3H), 1.39 (s, 3H) |
| 22 | (structure) ·HCl | 21 | 373 | $^1$H NMR (500 MHz, DMSO-d$_6$) δ 9.93 (s, 2H), 8.54 (d, J = 7.2 Hz, 1H), 7.77 (s, 1H), 7.69 (d, J = 7.6 Hz, 1H), 7.47-7.34 (m, 5H), 7.23 (d, J = 6.6 Hz, 1H), 6.19 (dd, J = 7.6, 2.5 Hz, 1H), 6.02 (d, J = 2.5 Hz, 1H), 5.16 (s, 2H), 4.57 (s, 2H), 3.51 (s, 2H), 3.08 (t, J = 5.4 Hz, 2H) |
| 23 | (structure) ·HCl | 30 | 392 | $^1$H NMR (500 MHz, DMSO-d$_6$) δ 9.71 (s, 2H), 8.62 (d, J = 2.9 Hz, 1H), 8.47 (d, J = 7.2 Hz, 1H), 7.85-7.80 (overlapping ddd, J = 8.7, 2.3 Hz, 1H), 7.71-7.68 (m, 2H), 7.76-7.64 (dd, J = 8.6, 4.4 Hz, 1H), 7.14-7.12 (dd, J = 7.1, 1.4 Hz, 1H), 6.21-6.19 (dd, J = 7.7, 2.7 Hz, 1H), 6.02 (d, J = 2.7 Hz, 1H), 5.23 (s, 2H), 4.56 (s, 2H), 3.53-3.48 (m, 2H), 3.06 (t, J = 5.8 Hz, 2H) |
| 24 | (structure) ·HCl | 616 | 412 | $^1$H NMR (500 MHz, CD$_3$OD) δ 9.10 (d, J = 1.9 Hz, 1H), 8.48 (d, J = 7.2 Hz, 1H), 8.42-8.40 (dd, J = 8.1, 2.1 Hz, 1H), 7.98 (d, J = 8.1 Hz, 1H), 7.91 (d, J = 7.2 Hz, 1H), 7.84 (d, J = 1.6 Hz, 1H), 7.32-7.30 (dd, J = 7.2, 2.0 Hz, 1H), 7.04 (d, J = 1.7 Hz, 1H), 6.94-6.92 (dd, J = 7.2, 2.0 Hz, 1H), 4.71 (s, 2H), 3.72 (t, J = 6.1 Hz, 2H), 3.24 (t, J = 6.1 Hz, 2H) |

TABLE 1-continued

Compounds Tested for Biological Activity

| Ex, No. | Structure | MCH₁ K$_i$ (nM) | Mass Spec | ¹H NMR Data |
|---|---|---|---|---|
| 25 | (structure) ·HCl | 3323 | 442 | ¹H NMR (500 MHz, CD₃OD) δ 8.85 (s, 1H), 8.37 (d, J = 7.2 Hz, 1H), 8.16 (d, J = 8.2 Hz, 1H), 7.88 (d, J = 7.8 Hz, 1H), 7.69 (s, 1H), 7.67 (d, J = 7.5 Hz, 1H), 7.17-7.16 (dd, J = 7.3, 1.9 Hz, 1H), 6.38-6.36 (dd, J = 7.7, 2.7 Hz, 1H), 6.17 (d, J = 2.5 Hz, 1H), 5.35 (s, 2H), 4.67 (s, 2H), 3.70 (t, J = 6.1 Hz, 2H), 3.26 (t, J = 6.1 Hz, 2H) |
| 26 | (structure) ·HCl | 23 | 411 | ¹H NMR (500 MHz, CD₃OD) δ 8.74 (d, J = 6.9 Hz, 1H), 7.95 (d, J = 8.2 Hz, 2H), 7.91 (d, J = 1.6 Hz, 1H), 7.87 (d, J = 7.2 Hz, 1H), 7.84 (d, J = 8.2 Hz, 2H), 7.40-7.38 (dd, J = 7.2, 1.8 Hz, 1H), 6.97 (d, J = 1.6 Hz, 1H), 6.92-6.90 (dd, J = 7.2, 1.8 Hz, 1H), 4.72 (s, 2H), 3.73 (t, J = 6.2 Hz, 2H), 3.28 (t, J = 6.2 Hz, 2H) |
| 27 | (structure) ·HCl | 19 | 415 | ¹H NMR (500 MHz, DMSO-d₆) δ 11.25 (s, 1H), 8.16 (d, J = 7.2 Hz, 1H), 7.77 (s, 1H), 7.70 (d, J = 7.7 Hz, 1H), 7.48-7.39 (m, 5H), 7.24 (d, J = 6.8 Hz, 1H), 6.20-6.18 (dd, J = 7.8, 2.6 Hz, 1H), 6.02 (d, J = 2.8 Hz, 1H), 5.17 (s, 2H), 4.78 (d, J = 14.0 Hz, 1H), 4.60-4.52 (m, 1H), 3.83-3.61 (m, 2H), 3.51-3.41 (m, 1H), 3.37-3.26 (m, 1H), 3.07 (d, J = 15.0 Hz, 1H), 1.44 (d, J = 6.3 Hz, 3H), 1.41 (d, J = 6.3 Hz, 3H) |
| 28 | (structure) | 103 | 401 | ¹H NMR (300 MHz, DMSO-d₆) δ 8.28 (d, J = 8.2 Hz, 1H), 7.84 (d, J = 7.7 Hz, 1H), 7.49-7.34 (m, 6H), 7.25 (br t, 1H), 6.18 (dd, J = 7.8, 2.7 Hz, 1H), 6.01 (d, J = 2.7 Hz, 1H), 5.17 (s, 2H), 3.76 (s, 3H), 3.53 (td, J = 6.9, 2.4 Hz, 2H), 3.09 (t, J = 6.9 Hz, 2H) |

TABLE 1-continued

Compounds Tested for Biological Activity

| Ex, No. | Structure | MCH$_1$ K$_i$ (nM) | Mass Spec | $^1$H NMR Data |
|---|---|---|---|---|
| 29 | Enantiomer A 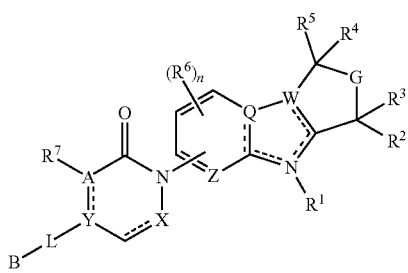 | 81 | 443 | $^1$H NMR (500 MHz, CDCl$_3$) δ 7.87 (m, 1H), 7.68 (m, 1H), 7.42-7.26 (m, 6H), 6.06 (m, 2H), 5.54 (m, 1H), 5.06 (s, 2H), 4.78 (m, 0.5H), 4.63 (m, 1H), 4.10 (m, 0.5H), 3.72 (s, 3H), 3.19 (m, 1H), 2.71 (m, 0.5H), 2.65 (m, 0.5H), 2.24 (m, 3H), 1.20 (m, 1.5H), 1.21 (m, 1.5H) |

As compounds that bind strongly to MCH-1, compounds of formula I are expected to be effective in reducing obesity.

The present invention is not limited to the compounds found in the above examples, and many other compounds falling within the scope of the invention may also be prepared using the procedures set forth in the above synthetic schemes. The preparation of additional compounds of formula (I) using these methods will be apparent to one of ordinary skill in the chemical arts.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound of formula (I):

(I)

wherein
G is —NR$^8$—CR$^9$R$^{10}$— or —CR$^9$R$^{10}$—NR$^8$—;
X is CR$^{16}$;
Y is C;
W is C;
Q is C;
Z is N;
L is —(CH$_2$)$_p$—O—, —(CH$_2$)$_p$—, —CH=CH—, or a bond;
A is C or CH;
B is aryl, heteroaryl, heterocyclyl, or cycloalkyl, wherein each of the aryl, heteroaryl, heterocyclyl, or cycloalkyl is optionally substituted with from 1 to 3 substituents selected from the group consisting of H, alkoxy, —S-alkyl, optionally substituted C$_1$-C$_6$ alkyl, halogen, —CF$_3$, and —CN;

R$^1$ is optionally present and, if present, is selected from the group consisting of H, —S(O)$_q$R$^{12}$, —C(O)$_R$$^{12}$, —C(O)NR$_{11}$R$^{12}$, C$_6$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, and heteroaryl is optionally substituted with from 1 to 3 substituents independently selected at each occurrence thereof from C$_1$-C$_3$ alkyl, halogen, —CN, —OR$^{14}$, —NR$^{14}$R$_{15}$, and phenyl which is optionally substituted 1-3 times with halogen, C$_1$-C$_4$ alkyl, C$_1$-C$_4$ haloalkyl, alkoxy, —CN, —OR$^{14}$, or —NR$^{14}$R$^{15}$;

R$^2$, R$^3$, R$^4$, R$^5$, R$^9$, and R$^{10}$ are each, independently, selected from the group consisting of H, halogen, —OR$^{11}$, —NR$^{11}$R$^{12}$, —NR$^{11}$C(O)R$^{12}$, —NR$^{11}$C(O)$_2$R$^{12}$, —NR$^{13}$C(O)NR$^{12}$R$^{13}$, —S(O)$_q$R$^{12}$, —CN, —C(O)R$^{12}$, —C(O)NR$^{11}$ $^{R12}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^{14}$, —NR$^{14}$R$^{15}$ and phenyl which is optionally substituted 1-3 times with halogen, C$_1$-C$_4$ alkyl, C$_1$-C$_4$ haloalkyl, C$_1$-C$_4$ alkoxy, —CN, —OR$^{14}$, or —NR$^{14}$R$^{15}$; or R$^2$ and R$^3$ or R$^4$ and R$^5$ can combine to form an oxo, thio, imine, cycloalkyl, or heterocycle group containing from 1 to 5 heteroatoms selected from the group consisting of oxygen, nitrogen, and sulfur;

R$^6$ is independently selected at each location from the group consisting of H, halogen, —OR$^{11}$, —$^{NR11}$C(O)R$^{12}$, —NR$^{11}$C(O)$_2$R$^{12}$, —NR$^{13}$C(O)NR$^{12}$R$^{13}$, —S(O)$_q$R$^{12}$, —CN, —C(O)R$^{12}$, —C(O)NR$^{11}$R$^{12}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{14}$, —$NR^{14}R^{15}$ and phenyl which is optionally substituted 1-3 times with halogen, $C_1$-$C_4$ alkyl, $C_1$-$C_4$ haloalkyl, $C_1$-$C_4$ alkoxy, —CN, —$OR^{14}$, or —$NR^{14}R^{15}$;

$R^7$ is optionally present and, if present, is selected from the group consisting of H, halogen, —$OR^{11}$, —$NR^{11}R^{12}$, —$NR^{11}C(O)R_{12}$, —$NR^{11}C(O)_2 NR^{12}$, —$NR^{13}C(O)NR^{12}R^{13}$, —$S(O)_qR'^2$, —CN, —$C(O)R^{12}$, —$C(O)NR^{11}R^{12}$, $C_{1-C6}$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{14}$, —$NR^{14}R^{15}$, and phenyl which is optionally substituted 1-3 times with halogen, $C_1$-$C_4$ alkyl, $C_1$-$C_4$ haloalkyl, $C_1$-$C_4$ alkoxy, —CN, —$OR^{14}$, or —$NR^{14}R^{15}$;

$R^8$ is selected from the group consisting of H, —$S(O)_qR^{12}$, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, and heteroaryl is optionally substituted with from 1 to 3 substituents independently selected at each occurrence thereof from $C_1$-$C_3$ alkyl, halogen, —CN, —$OR^{14}$, —$NR^{14}R^{15}$, and phenyl which is optionally substituted 1-3 times with halogen, $C_1$-$C_4$ alkyl, $C_1$-$C_4$ haloalkyl, $C_1$-$C_4$ alkoxy, —CN, —$OR^{14}$, or —$NR^{14}R^{15}$;

$R^{11}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{12}$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^{13}$ is $C_1$-$C_4$ alkyl, $C_1$-$C_4$ haloalkyl, or phenyl;

$R^{14}$ and $R^{15}$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^{13}$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

$R^{16}$ is selected from the group consisting of H, halogen, —$OR^{11}$, —$NR^{11}R^{12}$—$NR^{11}C(O)R^{12}$, —$NR^{11}C(O)_2R^{12}$, —$NR^{12}C(O)NR^{12}R^{13}$,—$S(O)_qR^{12}$, —CN, —$C(O)R^{12}$, —$C(O)NR^{11}R^{12}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{14}$, —$NR^{14}R^{15}$, and phenyl which is optionally substituted 1-3 times with halogen, $C_1$-$C_4$ alkyl, $C_1$-$C_4$ haloalkyl, $C_1$-$C_4$ alkoxy, —CN, —$OR^{14}$, or —$NR^{14}R^{15}$;

n is 0, 1, 2, or 3;
p is from 1 to 4;
q is 0, 1, or 2; and
═══ represents an optional double bond, or a pharmaceutically acceptable salt thereof or a solvate thereof.

2. The compound according to claim 1, wherein $R^1$ is H or $C_1$-$C_6$ alkyl.

3. The compound according to claim 2, wherein $R^1$ is H.

4. The compound according to claim 2, wherein $R^1$ is $C_1$-$C_6$ alkyl.

5. The compound according to claim 1, wherein X is CH.

6. The compound according to claim 1, wherein L is a bond.

7. The compound according to claim 1, wherein L is —$CH_2$—O—.

8. The compound according to claim 1, wherein L is —$CH_2$-$CH_2$-.

9. The compound according to claim 1, wherein B is phenyl, pyridinyl, pyridazinyl, or pyrimidinyl.

10. The compound according to claim 1, wherein B is unsubstituted.

11. The compound according to claim 1, wherein B is substituted with at least one substituent selected from trifluoromethyl, chloro, fluoro, methyl, and methanethio.

12. The compound according to claim 1, wherein B is selected from the group consisting of phenyl, 4-(trifluoromethyl)phenyl, 4-(methylthio)-phenyl, 5-(trifluoromethyl)pyridin-2-yl, 2-(trifluoromethyl)-pyrimidin-5-yl, 6-(trifluoromethyl)pyridazin-3-yl, 5-fluoro-pyridin-2-yl, 6-methylpyridin-3-yl, 6-(trifluoromethyl)pyridin-3-yl, 5-chloro-pyridin-2-yl, 2,4-dichloro-phenyl, 2,4-difluoro-phenyl, 4-chloro-phenyl, 4-chloro-2-fluoro-phenyl, 3,5-dichloro-pyridin-2-yl, 4-fluoro-phenyl, pyridin-2-yl, and 3,5-difluoro-pyridin-2-yl.

13. The compound according to claim 1, wherein n is 1.

14. The compound according to claim 1, wherein n is 2.

15. The compound according to claim 1, wherein the compound has the structure (IV):

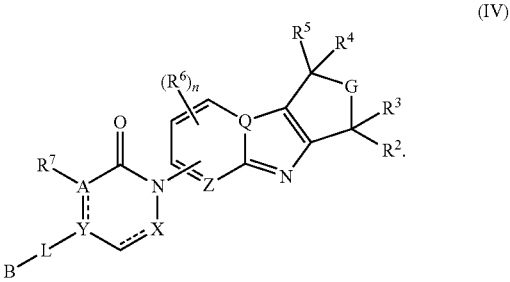

(IV)

16. The compound according to claim 1, wherein the compound has the formula:

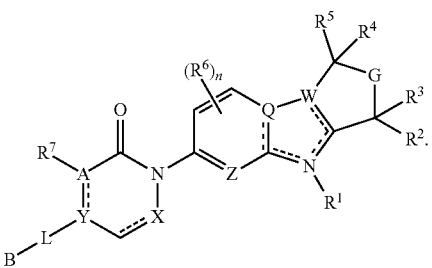

17. The compound according to claim 1, wherein the compound is selected from the group consisting of:
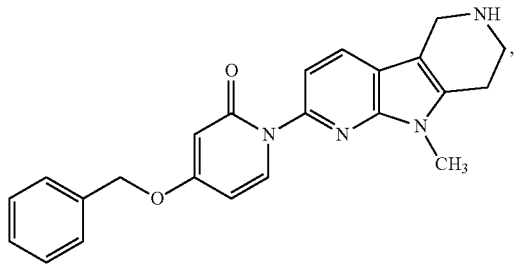
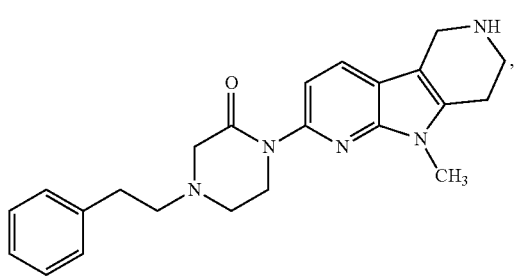
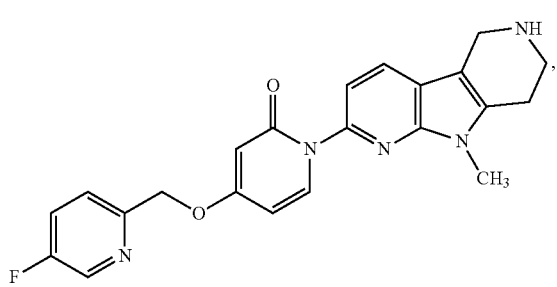
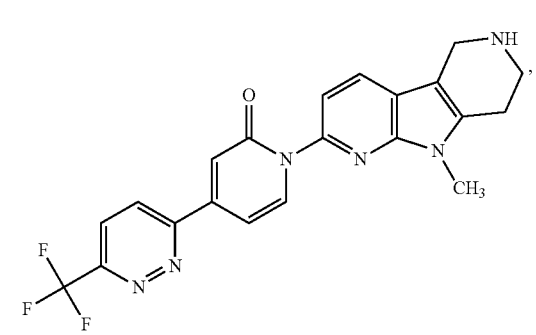
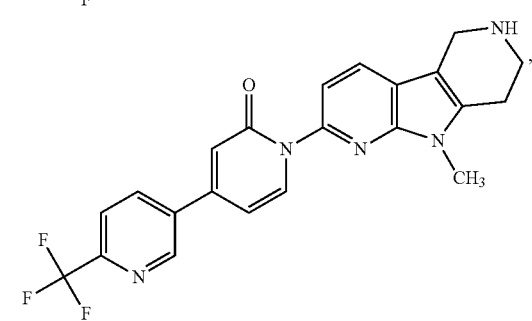
-continued
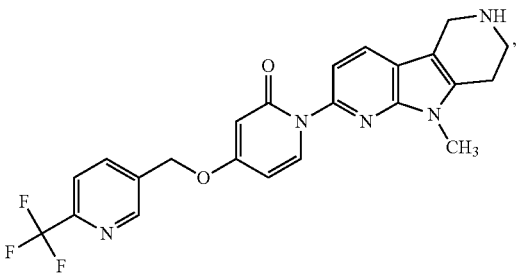
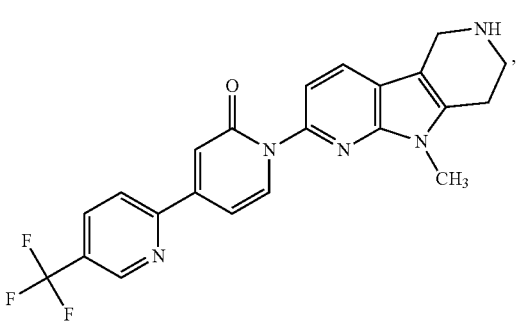
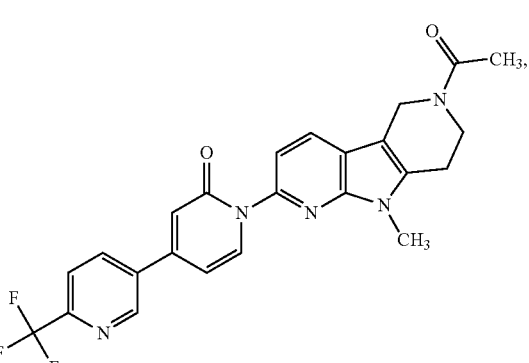
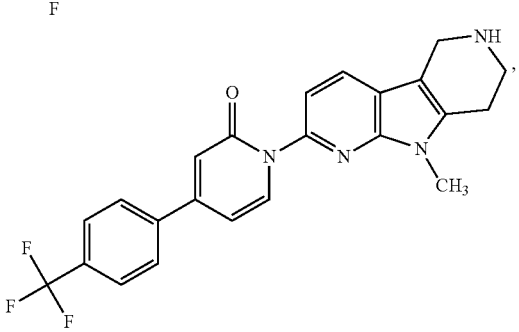
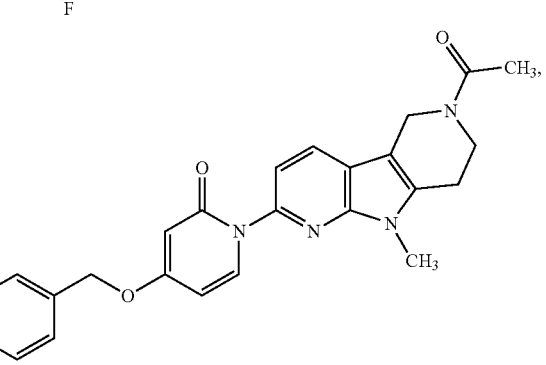

-continued

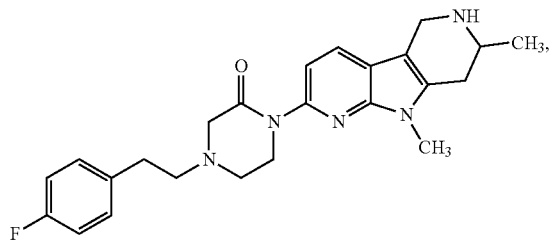

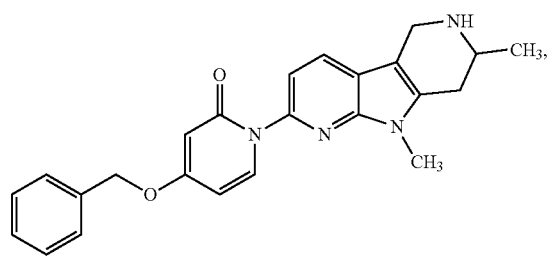

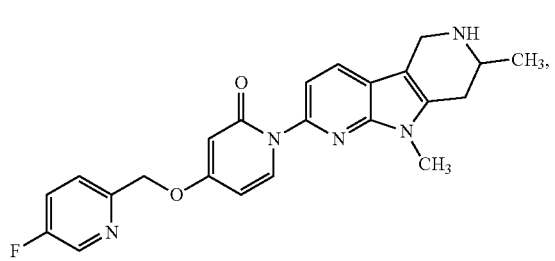

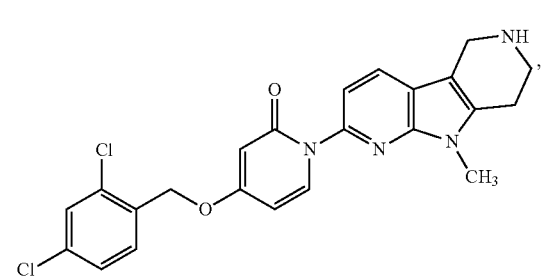

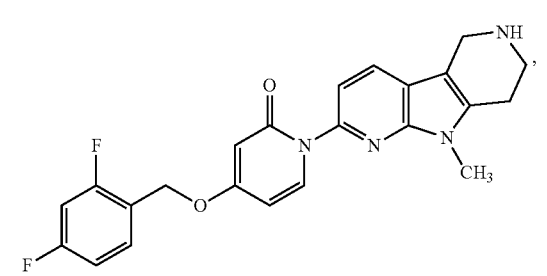

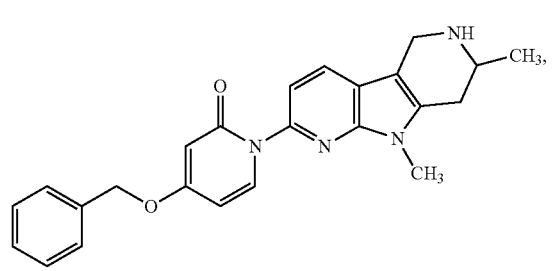

-continued

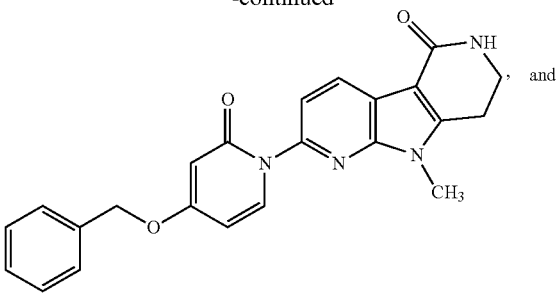

, and

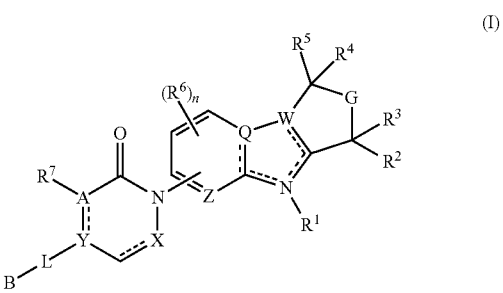

18. The compound according to claim 1, wherein the compound is an HC1 salt.

19. A pharmaceutical composition comprising a therapeutically effective amount of the compound according to claim 1 and a pharmaceutically acceptable carrier.

20. A method of treating obesity in a subject in need of weight loss comprising:
    selecting a patient in need of weight loss, and
    administering to the patient a therapeutically effective amount of a compound of claim 1 or a pharmaceutically acceptable salt thereof.

21. The method according to claim 20 further comprising:
    administering to the patient a therapeutically effective amount of an anti-obesity adjunct selected from the group consisting of phenylpropanolamine, ephedrine, pseudoephedrine, phentermine, leptin, amylin peptide, dehydroepiandrosterone, and combinations thereof.

22. A process for preparation of a product compound of formula (I):

(I)

wherein
G is —$NR^8$—$CR^9R^{10}$— or —$CR^9R^{10}$—$NR^8$—;
X is $CR^{16}$;
Y is C;
W is C;
Q is C;
Z is N;
L is —$(CH_2)_p$—O—, —$(CH_2)_p$—, —CH=CH—, or a bond;

A is C or CH;

B is aryl, heteroaryl, heterocyclyl, or cycloalkyl, wherein each of the aryl, heteroaryl, heterocyclyl, or cycloalkyl is optionally substituted with from 1 to 3 substituents selected from the group consisting of H, alkoxy, —S—alkyl, optionally substituted $C_1$—$C_6$ alkyl, halogen, —$CF_3$, and —CN;

$R^1$ is optionally present and, if present, is selected from the group consisting of H, $C_1$-$C_6$ alkyl, $C_3$-$C_6$ cycloalkyl, and $C_4$-$C_7$ cycloalkylalkyl;

$R^2$, $R^3$, $R^4$, $R^5$, $R^9$, and $R^{19}$ are each, independently, selected from the group consisting of H, $C_1$-$C_6$ alkyl, $C_3$-$C_6$ cycloalkyl, $C_4$-$C_7$ cycloalkylalkyl, and aryl;

$R^6$ is independently selected at each location from the group consisting of H, $C_1$-$C_6$ alkyl, $C_3$-$C_6$ cycloalkyl, $C_4$-$C_7$ cycloalkylalkyl, and aryl;

$R^7$ is optionally present and, if present, is selected from the group consisting of H, $C_1$-$C_6$ alkyl, $C_3$-$C_6$ cycloalkyl, $C_4$-$C_7$ cycloalkylalkyl, and aryl;

$R^8$ is selected from the group consisting of H, —$C(O)R^{12}$, $C_1$-$C_6$ alkyl, $C_3$-$C_6$ cycloalkyl, and $C_4$-$C_7$ cycloalkylalkyl;

$R^{11}$ is H, $C_1$-$C_4$ alkyl, $C_3$-$C_6$ cycloalkyl, $C_4$-$C_7$ cycloalkylalkyl, and phenyl;

R is H, $C_1$-$C_4$ alkyl, $C_3$-$C_6$ cycloalkyl, $C_4$-$C_7$ cycloalkylalkyl, and phenyl;

$R^{13}$ is $C_1$-$C_4$ alkyl or phenyl;

$R^{14}$ and $R^{15}$ are each independently H, $C_1$-$C_4$ alkyl, $C_3$-$C_6$ cycloalkyl, $C_4$-$C_7$ cycloalkylalkyl, and phenyl;

$R^{16}$ is selected from the group consisting of H, $C_1$-$C_6$ alkyl, $C_3$-$C_6$ cycloalkyl, $C_4$-$C_7$ cycloalkylalkyl, and aryl;

n is 0, 1, 2, or 3;

p is from 1 to 4; and

═ represents an optional double bond, said process comprising:
treating a first intermediate compound of formula V:

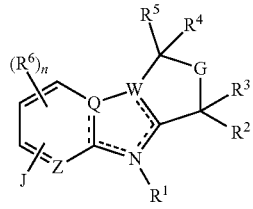

(V)

wherein J is a halogen, under conditions effective to form the product compound,
wherein treating comprises:
reacting the first intermediate with a second intermediate having the structure:

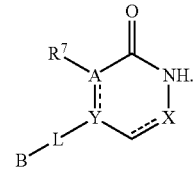

* * * * *